(12) United States Patent
Franzke et al.

(10) Patent No.: US 9,782,609 B2
(45) Date of Patent: Oct. 10, 2017

(54) DIHYDROXYALKYL SUBSTITUTED POLYGALACTOMANNAN, AND METHODS FOR PRODUCING AND USING THE SAME

(71) Applicant: HERCULES INCORPORATED, Wilmington (DE)

(72) Inventors: Michael Albert Hermann Franzke, Barendrecht (NL); Xiaochun Zhang, Barendrecht (NL); Gijsbert Kroon, Glessendam (NL)

(73) Assignee: HERCULES LLC, Wilmington, DE (US)

( * ) Notice: Subject to any disclaimer, the term of this patent is extended or adjusted under 35 U.S.C. 154(b) by 177 days.

(21) Appl. No.: 14/505,244

(22) Filed: Oct. 2, 2014

(65) Prior Publication Data

US 2015/0098921 A1  Apr. 9, 2015

Related U.S. Application Data

(60) Provisional application No. 61/887,679, filed on Oct. 7, 2013.

(51) Int. Cl.

| | | |
|---|---|---|
| *C08B 37/00* | (2006.01) | |
| *A61Q 5/06* | (2006.01) | |
| *A61Q 5/02* | (2006.01) | |
| *A61K 8/60* | (2006.01) | |
| *A61K 8/73* | (2006.01) | |

(52) U.S. Cl.
CPC .............. *A61Q 5/06* (2013.01); *A61K 8/60* (2013.01); *A61K 8/737* (2013.01); *A61Q 5/02* (2013.01); *C08B 37/009* (2013.01); *C08B 37/0087* (2013.01); *C08B 37/0093* (2013.01); *C08B 37/0096* (2013.01); *A61K 2800/54* (2013.01); *A61K 2800/5426* (2013.01)

(58) Field of Classification Search
None
See application file for complete search history.

(56) References Cited

U.S. PATENT DOCUMENTS

| | | |
|---|---|---|
| 2,496,670 A | 2/1950 | Moe |
| 2,523,708 A | 9/1950 | Moe |
| 4,661,475 A | 4/1987 | Bayerlein et al. |
| 7,262,157 B2 | 8/2007 | Utz et al. |
| 2011/0123563 A1* | 5/2011 | Langella ............ A61K 8/737 424/195.18 |
| 2011/0189248 A1 | 8/2011 | Baldaro et al. |
| 2013/0034505 A1 | 2/2013 | Lepilleur et al. |
| 2013/0129639 A1 | 5/2013 | Anderson et al. |

FOREIGN PATENT DOCUMENTS

| | | | | |
|---|---|---|---|---|
| WO | WO2011/137218 | * | 11/2011 | ............ C08B 37/00 |
| WO | WO2012170171 A1 | | 12/2012 | |

OTHER PUBLICATIONS

Kawamura, Y., "Carob bean gum Chemical and Technical Assessment (CTA)" (2008) pp. 1-6.*
Cassia Gum—Chemical and Technical Assessment (CTA) Prepared by Professor Symon M. Mahungu and Mrs Inge Meyland.

* cited by examiner

*Primary Examiner* — Eric Olson
(74) *Attorney, Agent, or Firm* — Dunlap Codding P.C.; Shaorong Chen

(57) ABSTRACT

Disclosed are compositions including dihydroxyalkyl substituted polygalactomannan, and the optional further substitution of such with cationic and/or hydrophobic moieties. Method of making such compositions is also disclosed as well as the use of such compositions in industrial applications, fabric laundering, and personal and household care.

18 Claims, 9 Drawing Sheets

DIHYDROXYALKYL SUBSTITUTED POLYGALACTOMANNAN, AND METHODS FOR PRODUCING AND USING THE SAME

CROSS REFERENCE TO RELATED APPLICATIONS

The present application claims the benefit under 35 U.S.C. 119(e) of U.S. Provisional Patent Application Ser. No. 61/887,679, filed on Oct. 7, 2013, the entire contents of which are hereby expressly incorporated herein by reference.

BACKGROUND

1. Field of the Invention

The presently disclosed and/or claimed inventive process(es), procedure(s), method(s), product(s), result(s), and/or concept(s) (collectively hereinafter referred to as the "presently disclosed and/or claimed inventive concept(s)") relates generally to dihydroxyalkyl substituted galactomannan polymers. More particularly, but not by way of limitation, the presently disclosed and/or claimed inventive concept(s) further relates to optionally modifying the substituted galactomannan polymers with cationic and/or hydrophobic moieties.

2. Background of the Invention

Galactomannan polymers (also called polygalactomanns) are generally obtained from the endosperm of seeds from leguminous plants such as *Cyamopsis tetragonoloba* (guar gum, mannose:galactose~2:1), *Trigonella foenum-graecum* (fenugreek gum, mannose:galactose~1:1), *Cesalpinia spinosa* (tara gum, mannose:galactose~3:1), *Ceratonia siliqua* (locust bean gum or carob gum, mannose:galactose~4:1), and *Cassia tora* and *Cassia obtusifolia* (cassia gum, mannose:galactose at least ~5:1). The formula below shows a segment of a galactomannan polymer.

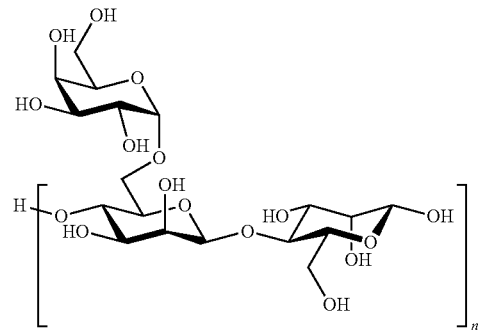

For illustrative purposes polygalactomannans obtained from the endosperm of *cassia* seed can be schematically represented by the structure:

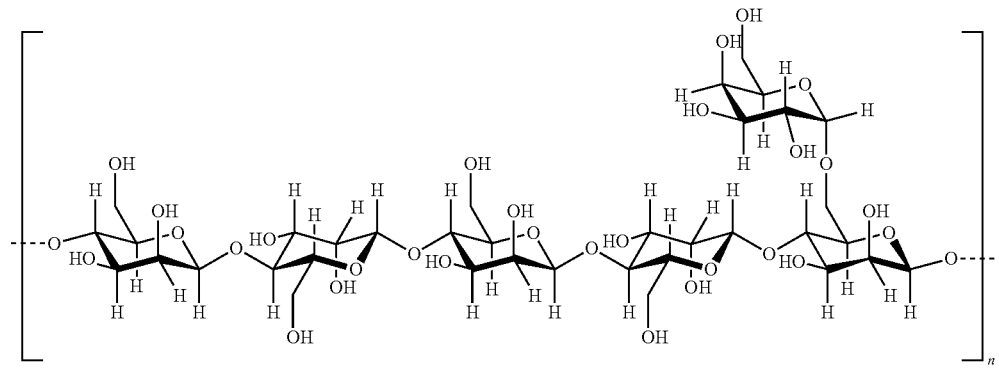

wherein n is an integer representing the number of repeating units in the polymer.

Galactomannan polymers are typically used in personal care, health care, household care, and industrial care compositions and the like. Such galactomannan polymers are also useful as deposition aids, stabilizers, emulsifiers, spreading aids and carriers for enhancing the efficacy, deposition and delivery of chemically and physiologically active ingredients. In addition, such polymers are useful as an active component in personal care compositions such as film formers, hair fixatives, hair conditioners, deposition aids, and skin conditioners. These polymers are also useful for improving the psychosensory and aesthetic properties of personal care formulations in which they are included. These polymers can also be used in fracturing fluid compositions in the oil and gas industry.

The galactomannan polymers of the different leguminosae species differ from one another in the frequency of the occurrence of the galactoside side units branching from the polymannoside backbone.

It is well recognized by those skilled in the art that natural polygalactomannans, even when obtained from a single source, will contain varying ranges of mannose to galactose ratios. Accordingly, these mannose to galactose ratios are reported as average ratios. The monosaccharide content of *Cassia* gum can be determined using a method adapted from Englyst et al. ("Determination of Dietary Fibre as Non-Starch Polysaccharides by Gas-Liquid Chromatography." Analyst (117), November 1992, pp. 1707-1714).

Polygalactomannans are hydrocolloids that have a high affinity for water. Although such natural polymers have been successfully used in various aqueous based formulations, they have suffered some drawbacks from a water solubility standpoint, especially at ambient temperature. It is known that the degree of water-solubility of polygalactomannans improves with increasing galactose to mannose ratio. For example, the polygalactomannan contained in guar gum (average mannose to galactose ratio 2:1) is mostly soluble in water at ambient temperature, while the polygalactomannan obtained from *cassia* gum (average mannose to galactose ratio 5:1) is only sparingly soluble in water at ambient temperature and very slightly soluble at elevated temperature. To expand the utility of such polygalactomannans in various aqueous based systems, it is important to chemically functionalize them to enhance their water-solubility and functional properties.

There is a need to develop novel functionalized polygalactomannans having excellent water-solubility and functional groups in order to improve their performance properties in various aqueous based systems.

DETAILED DESCRIPTION OF THE INVENTIVE CONCEPT(S)

Figure 1:
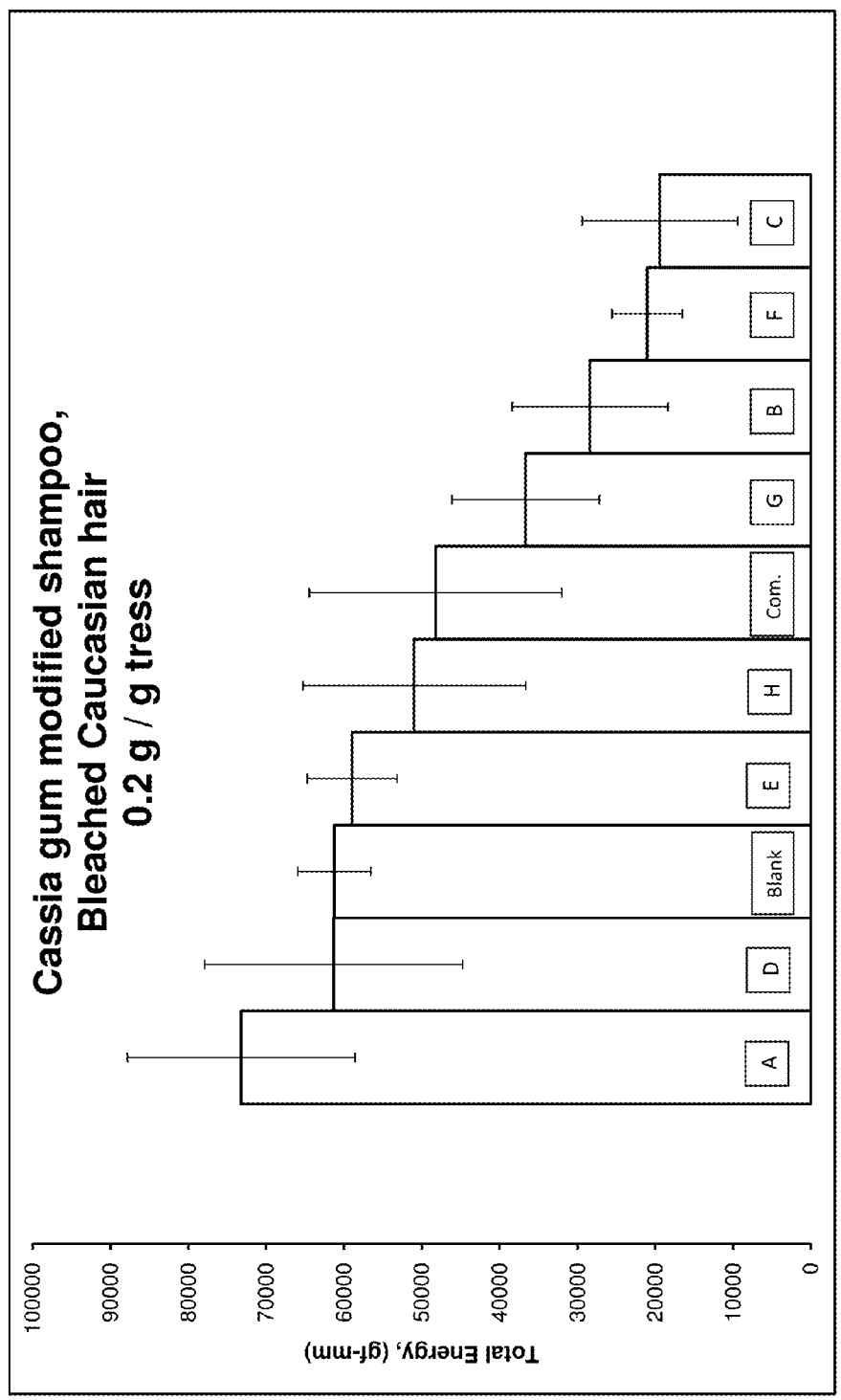
FIG. 1 is a plot showing Instron Wet Comb total energy test results for hair tresses treated with aqueous formulations A-H, Comparison and Blank.

Before explaining at least one embodiment of the presently disclosed and/or claimed inventive concept(s) in detail, it is to be understood that the presently disclosed and/or claimed inventive concept(s) is not limited in its application to the details of construction and the arrangement of the components or steps or methodologies set forth in the following description or illustrated in the drawings. The presently disclosed and/or claimed inventive concept(s) is capable of other embodiments or of being practiced or carried out in various ways. Also, it is to be understood that the phraseology and terminology employed herein is for the purpose of description and should not be regarded as limiting.

Unless otherwise defined herein, technical terms used in connection with the presently disclosed and/or claimed inventive concept(s) shall have the meanings that are commonly understood by those of ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the presently disclosed and/or claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed herein can be made and executed without undue experimentation in light of the present disclosure. While the compositions and methods of the presently disclosed and/or claimed inventive concept(s) have been described in terms of preferred embodiments, it will be apparent to those of ordinary skill in the art that variations may be applied to the compositions and/or methods and in the steps or in the sequence of steps of the method described herein without departing from the concept, spirit and scope of the presently disclosed and/or claimed inventive concept(s). All such similar substitutes and modifications apparent to those skilled in the art are deemed to be within the spirit, scope and concept of the presently disclosed and/or claimed inventive concept(s).

As utilized in accordance with the present disclosure, the following terms, unless otherwise indicated, shall be understood to have the following meanings.

The use of the word "a" or "an" when used in conjunction with the term "comprising" may mean "one," but it is also consistent with the meaning of "one or more," "at least one," and "one or more than one." The use of the term "or" is used to mean "and/or" unless explicitly indicated to refer to alternatives only if the alternatives are mutually exclusive, although the disclosure supports a definition that refers to only alternatives and "and/or." Throughout this application, the term "about" is used to indicate that a value includes the inherent variation of error for the quantifying device, the method being employed to determine the value, or the variation that exists among the study subjects. For example, but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one, including but not limited to, 1, 2, 3, 4, 5, 10, 15, 20, 30, 40, 50, 100, etc. The term "at least one" may extend up to 100 or 1000 or more depending on the term to which it is attached. In addition, the quantities of 100/1000 are not to be considered limiting as lower or higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first", "second", "third", "fourth", etc.) is solely for the purpose of differentiating between two or more items and, unless otherwise stated, is not meant to imply any sequence or order or importance to one item over another or any order of addition.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "or combinations thereof" as used herein refers to all permutations and combinations of the listed items preceding the term. For example, "A, B, C, or combinations thereof" is intended to include at least one of: A, B, C, AB, AC, BC, or ABC and, if order is important in a particular context, also BA, CA, CB, CBA, BCA, ACB, BAC, or CAB. Continuing with this example, expressly included are combinations that contain repeats of one or more item or term, such as BB, AAA, MB, BBC, AAAB-CCCC, CBBAAA, CABABB, and so forth. The skilled artisan will understand that typically there is no limit on the number of items or terms in any combination, unless otherwise apparent from the context.

As used herein, the terms "galactomannan", "galactomannan polymer", and "polygalactomannan" are used interchangeably and include any galactomannan and/or any polygalactomannan that swells upon contact with water, including all polysaccharides that are constructed of mannose and galactose building blocks and also have other sugar building blocks to a subordinate extent.

In accordance with an embodiment of the presently disclosed and/or claimed inventive concept(s) a composition is provided comprising a polygalactomannan substituted with at least one dihydroxyalkyl moiety wherein the composition comprises unsubstituted mannose, substituted mannose, unsubstituted galactose and substituted galactose, and wherein the molar ratio of the combined unsubstituted mannose and substituted mannose to the combined unsubstituted galactose and substituted galactose is at least about 2.0:1.

The dihydroxyalkyl moiety comprises $C_2$ to $C_{12}$ alkyl group. The dihydroxyalkyl moiety is selected from the group consisting of dihydroxyethyl, dihydroxypropyl, dihydroxybutyl, dihydroxypentyl, and dihyroxyhexy. In one non-limiting embodiment, the dihydroxyalkyl moiety is dihydroxypropyl.

In accordance with an embodiment of the presently disclosed and/or claimed inventive concept(s) the substituted galactomannan polymer is further substituted with at least one cationic moiety.

In accordance with an embodiment of the presently disclosed and/or claimed inventive concept(s) the substituted galactomannan polymer is further substituted with at least one hydrophobic moiety.

In accordance with an embodiment of the presently disclosed and/or claimed inventive concept(s) the polygalactomannan is isolated from the endosperm of the seeds of Cassia tora, Cassia obtusifolia, and combinations thereof.

The polygalactomannan can have a weight average molecular weight (Mw) which is within the range of 200,000 to 5,000,000 Daltons. In many cases, the polygalactomannan can have a weight average molecular weight, which is within the range of 300,000 to 2,000,000 Daltons. It is common for the polygalactomannan to have a weight average molecular weight, which is within the range of 400,000 to 1,500,000 Daltons. The molecular weight of the polygalactomannan can be varied through controlled degradation procedures known in the art.

Additionally, the polygalactomannan can have a number average molecular weight (Mn) which is within the range of 100,000 to 1,500,000 Daltons. In many cases, the polygalactomannan can have a number average molecular weight, which is within the range of 200,000 to 1,000,000 Daltons. It is common for the polygalactomannan to have a number average molecular weight, which is within the range of 300,000 to 900,000 Daltons. The weight average molecular weights and number average molecular weights referenced herein can be determined by gel permeation chromatography (GPC) or size exclusion chromatography (SEC) with refractive index and low angle light scattering detectors or other available detectors.

In accordance with an embodiment of the presently disclosed and/or claimed inventive concept(s), a composition comprises, consists of, or consists essentially of a polygalactomannan substituted with at least one dihydroxyalkyl moiety. Such composition comprises, consists of or consists essentially of unsubstituted mannose, substituted mannose, unsubstituted galactose and substituted galactose. Also, the molar ratio of the combined unsubstituted mannose and substituted mannose to the combined unsubstituted galactose and substituted galactose can be at least about 2.0:1, or at least about 4.0:1 or at least about 7.0:1. The molar ratio of the unsubstituted mannose to the unsubstituted galactose polymer can be from about 2.0 to about 7.0, or from about 3.0 to about 5.0. In addition, the polygalactomannan can be isolated from the endosperm of the seeds of Cassia tora, Cassia obtusifolia, and combinations thereof.

The at least one dihydroxyalkyl moiety can be substituted on the polygalactomannan in the form of an ether, and the average degree of molar substitution of the polygalactomannan by the at least one dihydroxyalkyl moiety can be in the range of from about 0.05 to about 5.0 or from about 0.1 to about 4.0. The composition can have a number average molecular weight (MO in the range of from about 50,000 to about 1,000,000, or from about 100,000 to about 700,000; and a weight average molecular weight ($M_w$) in the range of from about 70,000 to about 1,200,000 or from about 100,000 to about 1,000,000. Also, the ratio of $M_w/M_n$ can be in the range of from about 1.2 to about 5.0 or from about 1.5 to about 3.0.

In accordance with another embodiment, the polygalactomannan of the composition substituted with the at least one dihydroxyalkyl moiety can be further substituted with at least one hydrophobic moiety. The at least one hydrophobic moiety can be substituted on a terminal hydroxy group of the at least one dihydroxyalkyl moiety or on a hydroxy group of the polygalactomannan or on a terminal hydroxy group of the at least one dihydroxyalkyl moiety and on a hydroxy group of the polygalactomannan. The at least one hydrophobic moiety can be selected from a $C_4$-$C_{22}$ alkyl radical. The hydrophobic moiety can be an alkyl radical selected from the group consisting of linear or branched dodecyl radicals, linear or branched hexadecyl radicals, and linear or branched docosyl radicals. More particularly, such alkyl radicals can be selected from the group consisting of linear or branched dodecylhalide, linear or branched dodecyl glycidylether, linear or branched hexadecylhalide, linear or branched hexadocyl glycidylether, linear or branched docosylhalide, and linear or branched docosyl glycidylether.

In accordance with another embodiment, the polygalactomannan of the composition substituted with the at least one dihydroxyalkyl moiety can be further substituted with at least one cationic moiety. The at least one cationic moiety can be substituted on a terminal hydroxy group of the at least one dihydroxyalkyl moiety or on a hydroxy group of the polygalactomannan, or on a terminal hydroxy group of the at least one dihydroxyalkyl moiety and on a hydroxy group of the polygalactomannan.

The at least one cationic moiety can be any cationic moiety suitable for substitution on a hydroxy group. More particularly, the at least one cationic moiety can be selected from compounds having the formula: AB;

wherein A, independently, is selected from a linear or branched, substituted or unsubstituted $C_1$-$C_6$ alkyl radical;

wherein B, independently, is selected from $S^+R_1R_2X^-$, $N^+R_1R_2R_3X^-$, $P^+R_1R_2R_3X^-$, wherein $R_1$, $R_2$, and $R_3$, independently, are selected from the group consisting of hydrogen and linear and branched $C_1$-$C_{24}$ alkyl, and $X^-$ is an anion.

Further, A can comprise a compound selected from the group consisting of a 3-halo-2-hydroxypropyl group; a 2,3-epoxy propyl group; and combinations thereof.

In accordance with another embodiment, the polygalactomannan of the composition substituted with the at least one dihydroxyalkyl moiety and the cationic moiety can be further substituted with at least one hydrophobic moiety. The at least one hydrophobic moiety can be substituted on at least one of: a terminal hydroxy group of the at least one dihydroxyalkyl moiety, a hydroxy group of the polygalactomannan, and at least one cationic moiety. The hydrophobic moiety is the same as those described previously.

In accordance with another embodiment, the composition can comprise, consist of, or consist essentially of the polygalactomannan substituted as variously described above and at least one component selected from surfactants, fatty acid soap, hair and skin conditioning agents, suspending aids, emollients, emulsifiers, rheology modifiers, thickening agents, vitamins, hair growth promoters, self-tanning agents, sunscreens, skin lighteners, anti-aging compounds, anti-wrinkle compounds, anti-cellulite compounds, anti-acne compounds, anti-dandruff agents, anti-inflammatory compounds, analgesics, antiperspirant agents, deodorant agents, hair fixatives, particulates, abrasives, moisturizers, antioxidants, keratolytic agents, anti-static agents, foam boosters, hydrotropes, solublizing agents, chelating agents, antimicrobial agents, antifungal agents, pH adjusting agents, chelating agents, buffering agents, botanicals, hair colorants, hair dye, oxidizing agents, reducing agents, hair and skin bleaching agents, pigments, anticaries, anti-tartar agents, anti-plaque agents, solvents, a rheology modifier, and combinations thereof.

The surfactant can be selected from an anionic surfactant, a cationic surfactant, an amphoteric surfactant, a nonionic surfactant, and combinations thereof. The conditioning agent can be selected from silicones, organic conditioning oils, natural and synthetic waxes, cationic polymers, fatty alcohols, cationic surfactants, and combinations thereof. The silicone can be selected from silicone fluids, silicone oils, cationic silicones, silicone gums, high refractive silicones, silicone resins, emulsified silicones, dimethicone copolyols, amodimethicones; and combinations thereof; and the cationic modified polymer can be selected from a polyquaternium, a cationically modified polygalactomannan, and combinations thereof.

In accordance with another embodiment, a hair fixative composition can comprise, consist of, or consist essentially of: a) the polygalactomannan substituted as variously described above; and b) a component selected from a rheology modifier, a surfactant, an auxiliary fixative, a solvent, water, a conditioner, a propellant, neutralizing agent, fragrance, fragrance solubilizer, thickener, preservative, emulsifier, emollient, humectant, colorant, wax, and mixtures thereof.

The conditioner can be selected from silicones, organic conditioning oils, natural and synthetic waxes, cationic polymers, and combinations thereof; and the propellant can be selected from propane, butane, isobutene, dimethyl ether, 1,1-difluoroethane, carbon dioxide, and mixtures thereof.

In accordance with another embodiment, a skin care composition can comprise, consist of, or consist essentially of: a) the polygalactomannan substituted as variously described above; and b) a component selected from a rheology modifier, a surfactant, a solvent, water, a conditioner, a propellant, neutralizing agent, fragrance, fragrance solubilizer, thickener, preservative, emulsifier, emollient, humectant, a sunscreen agent, UV blocking agent, colorant, wax, and mixtures thereof.

The conditioner can be selected from a silicone, a cationic polymer, natural and synthetic oils, natural and synthetic waxes, and combinations thereof; and the solvent can be selected from a $C_1$-$C_6$ alcohol, a ketone, an ether, and combinations thereof. The cationic polymer can be selected from a polyquaternium compound, a cationically modified polygalactomannan, and combinations thereof.

The polygalactomannan substituted compositions as variously described above are suitable for the preparation of personal care (cosmetics, toiletries, cosmeceuticals) and topical health care products, including without limitation, hair care products, such as shampoos (including combination shampoos, such as "two-in-one" conditioning shampoos); post-shampoo rinses; setting and style maintenance agents including setting aids, such as gels and sprays, grooming aids, such as pomades, conditioners, perms, relaxers, hair smoothing products, and the like; skin care products (facial, body, hands, scalp and feet), such as creams, lotions, conditioners, and cleansing products; antiacne products; antiaging products (exfoliant, keratolytic, anticellulite, anti-wrinkle, and the like); skin protectants such as sunscreens, sunblock, barrier creams, oils, silicones, and the like; skin color products (whiteners, lighteners, sunless tanning accelerators, and the like); hair colorants (hair dyes, hair color rinses, highlighters, bleaches and the like); pigmented skin colorants (face and body makeups, foundation creams, mascara, rouge, lip products, and the like); bath and shower products (body cleansers, body wash, shower gel, liquid soap, soap bars, syndet bars, conditioning liquid bath oil, bubble bath, bath powders, and the like); nail care products (polishes, polish removers, strengtheners, lengtheners, hardeners, cuticle removers, softeners, and the like); and any aqueous acidic to substantially neutral to basic composition to which an effective amount of the polygalactomannan substituted compositions as variously described above can be incorporated for achieving a beneficial or desirable, physical or chemical, effect therein during storage and/or usage.

Toiletries and health and beauty aids, commonly referred to as HBAs, comprising polygalactomannan substituted compositions as variously described above, can include, without limitation, hair-removal products (shaving creams and lotions, depilatories, after-shave skin conditioners, and the like); deodorants and antiperspirants; oral care products (mouth, teeth and gums), such as mouthwash, dentifrice, such as toothpaste, tooth powder, tooth polishes, tooth whiteners, breath fresheners, denture adhesives, and the like; facial and body hair bleach; and the like. Other health and beauty aids that can contain the polygalactomannan substituted compositions as variously described above, include, without limitation, sunless tanning applications containing artificial tanning accelerators, such as dihydroxyacetone (DHA), tyrosine, tyrosine esters, and the like; skin depigmenting, whitening, and lightening formulations containing such active ingredients as kojic acid, hydroquinone, arbutin, fruital, vegetal or plant extracts, (lemon peel extract, chamomile, green tea, paper mulberry extract, and the like), ascorbyl acid derivatives (ascorbyl palmitate, ascorbyl stearate, magnesium ascorbyl phosphate, and the like); foot care products, such as keratolytic corn and callous removers, foot soaks, foot powders (medicated, such as antifungal athlete's foot powder, ointments, sprays, and the like, and antiperspirant powders, or non-medicated moisture absorbent powder), liquid foot sprays (non-medicated, such as cooling, and deodorant sprays, and medicated antifungal sprays, antiperspirant sprays, and the like), and foot and toenail conditioners (lotions and creams, nail softeners, and the like).

Topical health and beauty aids that can include the polygalactomannan substituted compositions as variously described above (e.g., as spreading aids and film formers) include, without being limited thereto, skin protective spray, cream, lotion, gel, stick and powder products, such as insect repellants, itch relief, antiseptics, disinfectants, sun blocks, sun screens, skin tightening and toning milks, and lotions, wart removal compositions, and the like.

In a given composition or application, the polygalactomannan substituted compositions as variously described above can, but need not, serve more than one function, such as a fixative, thickener, skin and hair conditioner, film former and carrier or deposition aid. In a personal care composition, the amount of polygalactomannan substituted compositions as variously described above that can be employed depends upon the purpose for which they are included in the formulation and can be determined by person skilled in the formulation art. Thus, as long as the desired physicochemical and functional properties are achieved, a useful amount of polygalactomannan substituted compositions as variously described above on a total composition weight basis, typically can vary in the range of from about 0.01% to about 30% in one aspect of the presently disclosed and/or claimed inventive concept(s), from about 0.05 wt. % to about 20 wt. % in another aspect, from about 0.1 wt. % to about 15 wt. % in a further aspect, and from 1 to about 10 wt. % in a still further aspect of the invention, based on the total weight of the composition, but is not limited thereto.

The polygalactomannan substituted compositions as variously described above can be employed as conditioners and/or deposition aids in hair fixative and styling shampoo compositions. In addition, they can be employed as a fixative agent in a hair fixative composition. The polygalactomannan substituted compositions as variously described above can be used in shampoos and conditioners to facilitate combability. Positively charged atom(s) can interact with the negatively charged hair fibers to form films. They also make the hair feel softer and smoother to the touch without creating excessive residual build-up. The polygalactomannan substituted compositions as variously described above can be used as part of a conditioner package in a conditioning detersive formulation that not only imparts cleansing, wet detangling, dry detangling and manageability attributes to the hair, but also is relatively non-irritating. This composition is thus suitable for use by young children and adults having sensitive skin and eyes. In addition, polygalactomannan substituted compositions as variously described above can be used as a deposition aid in the deposition of conditioning and therapeutic agents to the hair.

As is discussed herein, the polygalactomannan substituted compositions as variously described above permit, facilitate and/or enhance the delivery, deposition and/or activity of one or more active ingredients utilized in a personal care, home care, health care, and institutional care formulations, and for improving the psychosensory and aesthetic properties of a topical formulation in which they are included. Examples of such active ingredients include, but are not limited to, caffeine, vitamin C, vitamin D, vitamin E, anti-stretch mark compounds, astringents (e.g., alum, oatmeal, yarrow, witch hazel, bayberry, and isopropyl alcohol), draining compounds, hair growth promoting compounds (e.g., monoxidil), skin and hair nourishing compounds, skin and hair protecting compounds, self-tanning compounds (e.g., mono- or polycarbonyl compounds such as, for example, isatin, alloxan, ninhydrin, glyceraldehyde, mesotartaric aldehyde, glutaraldehyde, erythrulose, tyrosine, tyrosine esters, and dihydroxyacetone), sunscreens (e.g., ethylhexyl methoxy cinnamate, octinoxate, octisalate, oxybenzone), skin lighteners (e.g., kojic acid, hydroquinone, arbutin, fruital, vegetal or plant extracts, such as lemon peel extract, chamomile, green tea, paper mulberry extract, and the like, ascorbyl acid derivatives, such as ascorbyl palmitate, ascorbyl stearate, magnesium ascorbyl phosphate, and the like), lip plumping compounds, anti-aging, anti-cellulite, and anti-acne compounds (e.g., acidic agents such as alpha-hydroxy acids (AHAs), beta-hydroxy acids (BHAs), alpha amino-acids, alpha-keto acids (AKAs), acetic acid, azelaic acid, and mixtures thereof), anti-dandruff compounds (e.g., zinc pyrithione, zinc omadine, miconazole nitrate, selenium sulfide, piroctone olamine, climbazol) anti-inflammatory compounds (e.g., aspirin, ibuprofen, and naproxen), analgesics (e.g., acetaminophen), antioxidant compounds, antiperspirant compounds (e.g., aluminum halides, aluminum hydroxyhalides, aluminum sulfate, zirconium (zirconyl) oxyhalides, zirconium (zirconyl)hydroxyhalides, and mixtures or complexes thereof), deodorant compounds (e.g., 2-amino-2-methyl-1-propanol (AMP), ammonium phenolsulfonate; benzalkonium chloride; benzethonium chloride, bromochlorophene, cetyltrimethylammonium bromide, cetyl pyridinium chloride, chlorophyllin-copper complex, chlorothymol, chloroxylenol, cloflucarban, dequalinium chloride, dichlorophene, dichloro-m-xylenol, disodium dihydroxyethyl sulfosuccinylundecylenate, domiphen bromide, hexachlorophene, lauryl pyridinium chloride, methylbenzethonium chloride, phenol, sodium bicarbonate, sodium phenolsulfonate, triclocarban, triclosan, zinc phenolsulfonate, zinc ricinoleate, and mixtures thereof), hair fixative polymers (e.g., natural and synthetic polymers such as, for example, polyacrylates, polyvinyls, polyesters, polyurethanes, polyamides, modified cellulose, starches, and mixtures thereof), hair and skin conditioners (e.g., synthetic oils, natural oils, such as vegetable, plant and animal oils, mineral oils, natural and synthetic waxes, cationic polymers, monomeric and polymeric quaternized ammonium salt compounds, silicones such as silicone oils, resins and gums, proteins, hydrolyzed proteins, fatty acids, fatty amines; and mixtures thereof); and suitable mixtures of two or more of the above.

The polygalactomannan substituted compositions as variously described above are particularly useful as deposition aids for particulates, such as mica, pearlizing agents, beads, and the like, making them suitable for dermal products containing particulates, microabrasives, and abrasives, such as shower gels, masks and skin cleansers containing exfoliating agents. Numerous cosmetically useful particulate exfoliating agents are known in the art, and the selection and amount is determined by the exfoliating effect desired from the use of the composition, as recognized by those skilled in the cosmetic arts. Useful exfoliating agents include, but are not limited to, biological abrasives, inorganic abrasives, synthetic polymers, and the like, and mixtures thereof. Biological abrasives include, without limitation, shell, seed, and kernel or stone granules or powders, obtained from nuts, such as from walnut (*Juglans regia*) shells, almonds, pecans, and the like; fruit sources, such as apricots, avocados, coconuts, olives, peaches, and the like; vegetal sources, such as corn cob, oat bran, rice, rose hip seed, jojoba (wax, seed powder), microcrystalline cellulose, ground loofa, ground seaweed, and the like; animal sources, such as oyster shell, silk, microcrystalline collagen, and the like. Inorganic abrasives include, without limitation, stannic oxide, talc, silica (hydrated, colloidal and the like), kaolin, precipitated chalk, salts (sodium chloride, dead sea salt, and the like), ground pumice, and the like. Synthetic polymers include, without limitation, microcrystalline polyamides (nylons), microcrystalline polyesters (polycarbonates), and the like.

The polygalactomannan substituted compositions as variously described above are useful as thickeners and film-formers in a variety of dermatological, cosmeceutical compositions employed for topically ameliorating skin conditions caused by drying, photo-damage, aging, acne, and the like, containing conditioners, moisturizers, antioxidants, keratolytic agents, vitamins, and the like, typically containing an active acidic ingredient and having a pH in the range of about 0.5 to about 5.

In one cosmeceutical aspect, the polygalactomannan substituted compositions as variously described above can be employed as a thickener or deposition aid for active skin treatment lotions and creams containing, as active ingredients, acidic anti-aging, anti-cellulite, and anti-acne agents, hydroxy carboxylic acids, such as alpha-hydroxy acid (AHA), beta-hydroxy acid (BHA), alpha-amino acid, alpha-keto acids (AKAs), and mixtures thereof. In such cosmeceuticals, AHAs can include, but are not limited to, lactic acid, glycolic acid, fruit acids, such as malic acid, citric acid, tartaric acid, extracts of natural compounds containing AHA, such as apple extract, apricot extract, and the like, honey extract, 2-hydroxyoctanoic acid, glyceric acid (dihydroxypropionic acid), tartronic acid (hydroxypropanedioic acid), gluconic acid, mandelic acid, benzilic acid, azelaic acid, alpha-lipoic acid, salicylic acid, AHA salts and derivatives, such as arginine glycolate, ammonium glycolate, sodium glycolate, arginine lactate, ammonium lactate, sodium lactate, alpha-hydroxybutyric acid, alpha-hydroxyisobutyric acid, alpha-hydroxyisocaproic acid, alpha-hydroxyisovaleric acid, atrolactic acid, and the like. BHAs can include, but are not limited to, 3-hydroxy propanoic acid, beta-hydroxybutyric acid, beta-phenyl lactic acid, beta-phenylpyruvic acid, and the like. Alpha-amino acids include, without being limited thereto, alpha-amino dicarboxylic acids, such as aspartic acid, glutamic acid, and mixtures thereof, sometimes employed in combination with fruit acid. AKAs include pyruvic acid. In some antiaging compositions, the acidic active agent may be retinoic acid, a halocarboxylic acid, such as trichloroacetic acid, an acidic antioxidant, such as ascorbic acid (vitamin C), a mineral acid, phytic acid, lysophosphatidic acid, and the like. Some acidic anti-acne actives, for example, can include salicylic acid, derivatives of salicylic acid, such as 5-octanoylsalicylic acid, retinoic acid, and its derivatives.

$S^+R_1R_2X^-$, $N^+R_1R_2R_3X^-$, $P^+R_1R_2R_3X$

A discussion of the use and formulation of active skin treatment compositions is in Cosmetics & Toiletries®, C&T Ingredient Resource Series, "AHAs & Cellulite Products How They Work", published 1995, and "Cosmeceuticals", published 1998, both available from Allured Publishing Corporation, incorporated herein by reference. Compositions containing alpha-amino acids acidified with ascorbic acid are described in U.S. Pat. No. 6,197,317 B1, and a commercial cosmeceutical preparation utilizing these acids in an anti-aging, skin care regimen is sold under the trade name, AFAs, by exCel Cosmeceuticals (Bloomfield Hills, Mich.). The term "AFA", as described in the supplier's trade literature, was coined by the developer to describe the amino acid/vitamin C combination as Amino Fruit Acids and as the acronym for "Amino acid Filaggrin based Antioxidants."

Other health care products in which polygalactomannan substituted compositions as variously described above can be included are medical products, such as topical and non-topical pharmaceuticals, and devices. In the formulation of pharmaceuticals, the polygalactomannan substituted compositions as variously described above can be employed as a thickener and/or lubricant in such products as creams, pomades, gels, pastes, ointments, tablets, gel capsules, purgative fluids (enemas, emetics, colonics, and the like), suppositories, anti-fungal foams, eye products (ophthalmic products, such as eye drops, artificial tears, glaucoma drug delivery drops, contact lens cleaner, and the like), ear products (wax softeners, wax removers, otitis drug delivery drops, and the like), nasal products (drops, ointments, sprays, and the like), and wound care (liquid bandages, wound dressings, antibiotic creams, ointments, and the like), without limitation thereto.

The film-forming polygalactomannan substituted compositions as variously described above make them particularly suitable as a vehicle for topical medical compositions for promoting and enhancing the transdermal delivery of active ingredients to or through the skin, for enhancing the efficacy of anti-acne agents formulations and topical analgesics, and for controlling release of drugs, such as antacids from tablets, or syrups, at low pH, such as in the stomach; controlling drug release from tablets, lozenges, chewables, and the like in the mildly acidic environment of the mouth; or from suppositories, ointments, creams, and the like in the mildly acidic environment of the vagina; to promote deposition of dandruff control agents from shampoos, salves, and the like; to enhance the deposition of colorants on skin from pigmented cosmetics (makeups, lipsticks, rouges, and the like) and on hair from hair dyes, and the like.

In addition to the foregoing, the cationic character of the polygalactomannan substituted compositions as variously described above, which have been cationically modified, and its cationic compatibility, makes the polymer useful as a thickener or deposition aid for antistatic, biocidal, antimicrobial, and other preservative compositions, in a variety of personal care, health care, I&I, and medical applications. For example, the polymer can be employed as a thickener in over-the-counter (OTC) health care and pharmaceutical products where cationic biocides are typically employed, such as in oral care compositions for plaque and tartar control, and liquid vehicles containing therapeutic agents, such as syrups, gels, and the like. Under certain controlled pH conditions, the cationic character of the polygalactomannan substituted compositions as variously described above, which have been cationically modified, itself, may also provide antistatic activity or biocidal, antimicrobial, or like preservative activity.

The polygalactomannan substituted compositions as variously described above can be employed, without limitation, as a lubricant coating for medical devices, such as soft tissue implants, surgical gloves, catheters, cannulae, and the like, as removable protective film coatings for medical instruments, wound dressings, and the like, as a muco-adhesive, especially in the acid environment of the stomach, as a carrier and thickener in formulated products for medical applications, such as disinfectant hand creams, antiviral products (for anionic viruses), antibiotic ointments, sprays and creams, non-drip, sprayable disinfectant in hospitals, hard surface antimicrobial finish applied during routine maintenance, and the like.

The polygalactomannan substituted compositions as variously described above can be used in home care, and I&I applications, for example, as a rheology modifier, fabric conditioning agent, antistatic agent, especially to improve formulation efficiency through "cling-on-surface" or improving efficacy of disinfectants, and biocidal formulations, and to synergistically improve fabric softening efficacy in combination with traditional fabric softeners. Typical household and I&I products that may contain polymers of the invention, include, without being limited thereto, laundry and fabric care products, such as detergents, fabric softeners (liquids or sheets), ironing sprays, dry cleaning aids, anti-wrinkle sprays, spot removers and the like; hard surface cleansers for the kitchen and bathroom and utilities and appliances employed or located therein, such as toilet bowl gels, tub and shower cleaners, hard water deposit removers, floor and tile cleansers, wall cleansers, floor and chrome fixture polishes, alkali-strippable vinyl floor cleaners, marble and ceramic cleaners, air freshener gels, liquid cleansers for dishes, and the like; disinfectant cleaners, such as toilet bowl and bidet cleaners, disinfectant hand soaps, room deodorizers, and the like.

The polygalactomannan substituted compositions as variously described above can be utilized as rheology modifiers, dispersants, stabilizers, promoters, or antimicrobials, and the like, in industrial product applications, such as, without being limited thereto, textiles (processing, finishing, printing, and dyeing aids, protective washable surface coatings, manufacture of synthetic leather by saturation of non-woven fabrics, and the like, manufacturing of woven fabrics, non-woven fabrics, natural and synthetic fibers and the like); water treatments (waste water, cooling water, potable water purification, and the like); chemical spill containments (acid-spill absorbent, and the like); leather and hide processing (processing aids, finishing, coating, embossing, and the like); paper and papermaking (surface coatings, such as pigmented coatings, antistatic coatings, and the like, pulp binders, surface sizings, dry and wet strength enhancers, manufacture of wet-laid felts, and the like); printing (inks, anti-wicking ink-jet printer inks, thickeners for ink formulations containing cationic dyes for printing acrylic fabrics, and the like); paints (pigment and grinding additive); industrial plant effluent treatment (flocculents for phenolics in paper mill effluent, and the like); metal working (acid etch cleaners, low pH metal coatings, pickling agents in cold rolled steel processing, and the like); adhesives (clear adhesives, adhesion promoters for metal, plastic, wood, and the like, non-woven floc adhesive tie coatings, bonding, and the like); wood preservation; and industrial construction products for buildings and roads (cement plasticizers, asphalt emulsion stabilizers at low pH, acid etch for cement, consistency modifiers of concrete, mortar, putty, and the like). The polygalactomannan substituted compositions as variously described above are particularly useful as thickeners for rust removers, acid truck cleaners, scale removers, and the like, and as dispersion stabilizers of products containing particulates, such as clay, pigments (titanium dioxide, calcium carbonate, and other minerals), abrasives, and the like, employed in a variety of the foregoing industrial applications, and in drilling muds.

Products containing polygalactomannan substituted compositions as variously described above can contain various conventional additives and adjuvants known in the art, some of which can serve more than one function. The amounts employed will vary with the purpose and character of the product and can be readily determined by one skilled in the formulation arts and from the literature. The term "cosmetic adjuvant" includes cosmetically and pharmaceutically acceptable product stabilizing and product finishing agents that maintain the physical stability of the composition and its visible aesthetic appearance and market appeal during the useful shelf life of the composition.

The term "fixative" as applied to polymers encompasses the properties of film-formation, adhesion, or coating deposited on a surface on which the polymer is applied. The terms "hair styling and hair fixative" as commonly understood in the hair care arts, and as used herein, refer collectively to hair setting agents that are hair fixatives and film formers and which are topically applied to the hair to actively contribute to the ease of styling and/or holding of a hair set, and to maintain the restylability of the hair set. Hence, hair setting compositions include hair styling, hair fixative, and hair grooming products that conventionally are applied to the hair (wet or dry) in the form of gels, rinses, emulsions (oil-in-water, water-in-oil or multiphase), such as lotions and creams, pomades, sprays (pressurized or non-pressurized), spritzes, foams, such as mousses, shampoos, solids, such as sticks, semisolids and the like, or are applied from a hair setting aid having the hair setting composition impregnated therein or coated thereon, to leave the hair setting agent in contact on the hair for some period until removed, as by washing.

The term "conditioning agents", and grammatical variations thereof, as it relates to compositions for skin care and hair care includes cosmetically and pharmaceutically useful materials that can function as humectants, moisturizers, and emollients. It is recognized that some conditioning agents can serve more than one function in a composition, such as an emulsifying agent, a lubricant, and/or a solvent. Conditioning agents include any material which is used to give a particular conditioning benefit to hair and/or skin. In hair treatment compositions, suitable conditioning agents are those which deliver one or more benefits relating to shine, softness, combability, antistatic properties, wet-handling, damage repair, manageability, detangling, body, and lubricity. Suitable conditioning agents for use in personal cleansing compositions are those conditioning agents characterized generally as silicones (e.g. silicone fluids, silicone oils, cationic silicones, silicone gums, high refractive silicones, silicone resins, emulsified silicones, and dimethicone copolyols), organic conditioning oils (e.g. hydrocarbon oils, natural oils, polyolefins, and fatty esters), natural and synthetic waxes, fatty esters, cationic polymers (including polyquaternium polymers), monomeric quaternary ammonium compounds, and combinations thereof.

A preferred hair care composition embodiment comprises the polygalactomannan substituted compositions as variously described above in an amount effective to provide to the hair care composition a property, such as a hair fixative property, a hair conditioning property, a viscid property (thickening, rheology modifying), or a combination thereof. Optionally, the hair care composition can include one or more auxiliary film-forming agent, auxiliary hair-fixative agent, auxiliary hair conditioning agent, auxiliary rheology modifying agent, propellants, and a combination thereof.

A preferred skin care composition embodiment comprises the polygalactomannan substituted compositions as variously described above in an amount effective to provide to the skin care composition a property, such as a skin conditioning property, a viscid property (thickening, rheology modifying), or a combination thereof. Optionally, the skin care composition can include one or more auxiliary skin conditioning agent, auxiliary rheology modifying agent, or a mixture thereof.

Product formulations comprising the polygalactomannan substituted compositions as variously described above can contain various additives and cosmetic adjuvants, conventionally or popularly included in personal care, household care, institutional care, and industrial care products, and in industrial processes, including, without being limited thereto, acidifying or alkalizing pH adjusting agents (neutralizing agents) and buffering agents; auxiliary fixatives and film formers, such as nonionic, anionic, cationic, or amphoteric polymers of synthetic or natural origin, and the like; auxiliary rheology modifiers, such as viscosity-increasing polymeric, gum, or resin thickeners or gellants; additives, such as emulsifiers, emulsion stabilizers, waxes, dispersants, and the like, and viscosity control agents, such as solvents, electrolytes, and the like; auxiliary conditioning agents, such as antistatic agents, synthetic oils, vegetable or animal oils, silicone oils, monomeric or polymeric quaternized ammonium compounds and derivatives thereof, sheen enhancers, moisturizers, emollients, humectants, lubricants, sunscreen agents, and the like; oxidizing agents; reducing agents; surfactants, such as anionic, cationic, nonionic, amphoteric, zwitterionic surfactants, and silicone derivatives thereof; polymer film modifying agents, such as plasticizers, tackifiers, detackifiers, wetting agents, and the like; product stabilizing and finishing agents, such as chelating agents, opacifiers, pearlescing agents, proteinaceous materials and derivatives thereof, vitamins and derivatives thereof, preservatives, fragrances, solubilizers, colorants (temporary or permanent), such as pigments and dyes, UV absorbers, and the like; propellants (water-miscible or water-immiscible), such as fluorinated hydrocarbons, liquid volatile hydrocarbons, compressed gases, and the like; and mixtures thereof.

Additives and adjuvant ingredients, products, or materials, which may be employed with the polygalactomannan substituted compositions as variously described above will be referred to by the international nomenclature commonly referred to as INCI name given them in the International Cosmetic Ingredient Dictionary, published by the Personal Care Products Council (formally the Cosmetic, Toiletry, and Fragrance Association), Washington D.C. (hereafter INCI Dictionary), such as can be found in any edition thereof, for example, Volumes 1 and 2, Sixth Edition, (1995) or Volumes 1-3, Seventh and Eighth Editions, (1997, 2000), or by their commonly used chemical names. Numerous commercial suppliers of materials listed by INCI name, trade name or both can be found in the INCI Dictionary and in numerous commercial trade publications, including but not limited to the 2001 McCutcheon's Directories, Volume 1: Emulsifiers & Detergents and Volume 2: Functional Materials, published by McCutcheon's Division, The Manufacturing Confectioner Publishing Co., Glen Rock, N.J. (2001); and 2001 Cosmetic Bench Reference, edition of Cosmetics & Toiletries®, 115 (13), published by Allured Publishing Corporation, Carol Stream, Ill. (2001); the relevant disclosures of each are incorporated herein by reference. Such components and the formulation of compositions are also described in detail in well known references, such as Cosmetics Science and Technology, First Edition (Sagarin (ed)), published 1957, and Second Edition (Balsam, et al. (eds)), published 1972-74; and The Chemistry and Manufacture of Cosmetics, Second Edition (deNavarre (ed)), published 1975, and Third Edition (Schlossman (ed)), published 2000, both available from Allured Publishing Corporation; Rieger (ed), Harry's Cosmeticology, 8th Edition, Chemical Publishing, Co., Inc., New York, N.Y. (2000); and various formularies available to those skilled in the pharmaceutical arts, such as Remington's Pharmaceutical Sciences, Fourteenth Edition, Mack Publishing Company, Easton, Pa. (1970); the relevant disclosures of each are incorporated herein by reference.

It is known that formulated compositions for personal care and topical, dermatological, health care, which are applied to the skin and mucous membranes for cleansing or soothing, are compounded with many of the same or similar physiologically tolerable ingredients and formulated in the same or similar product forms, differing primarily in the purity grade of ingredient selected, by the presence of medicaments or pharmaceutically accepted compounds, and by the controlled conditions under which products may be manufactured. Likewise, many of the ingredients employed in products for households, and I&I are the same or similar to the foregoing, differing primarily in the amounts and material grade employed. It is also known that the selection and permitted amount of ingredients also may be subject to governmental regulations, on a national, regional, local, and international level. Thus, discussion herein of various useful ingredients for personal care and health care products may apply to household and I&I products and industrial applications.

The choice and amount of ingredients in formulated compositions containing the polygalactomannan substituted compositions as variously described above will vary depending on the product and its function, as is well known to those skilled in the formulation arts. Formulation ingredients for personal care and topical health care products typically can include, but are not limited to, solvents, surfactants (as cleansing agents, emulsifying agents, foam boosters, hydrotropes, solubilizing agents, and suspending agents), non-surfactant suspending agents, emulsifiers, skin conditioning agents (emollients, humectants, moisturizers, and the like), hair conditioning agents, hair fixatives, film-formers, skin protectants, binders, chelating agents, antimicrobial agents, antifungal agents, antidandruff agents, abrasives, adhesives, absorbents, dyes, deodorant agents, antiperspirant agents, opacifying and pearlescing agents, antioxidants, preservatives, propellants, spreading aids, sunscreen agents, sunless skin tanning accelerators, ultraviolet light absorbers, pH adjusting agents, botanicals, hair colorants, oxidizing agents, reducing agents, hair and skin bleaching agents, pigments, physiologically active agents, anti-inflammatory agents, topical anesthetics, fragrance and fragrance solubilizers, and the like, in addition to ingredients previously discussed that may not appear herein. Oral care products, for example, can contain anticaries, anti-tartar and/or anti-plaque agents in addition to surfactants, abrasives, humectants, and flavorants. An extensive listing of substances and their conventional functions and product categories appears in the INCI Dictionary, generally, and in Vol. 2, Sections 4 and 5 of the Seventh Edition, in particular, incorporated herein by reference.

The polygalactomannan substituted compositions as variously described above are particularly useful for water-based, solvent based, hydroalcoholic based, and mixed solvent formulations, and for formulations containing water-miscible auxiliary solvents, but are not limited thereto. Useful solvents commonly employed are typically liquids, such as water (deionized, distilled or purified), polyols, and the like, and mixtures thereof. Non-aqueous or hydrophobic auxiliary solvents are commonly employed in substantially water-free products, such as nail lacquers, aerosol propellant sprays, or for specific functions, such as removal of oily soils, sebum, make-up, or for dissolving dyes, fragrances, and the like, or are incorporated in the oily phase of an emulsion. Non-limiting examples of auxiliary solvents, other than water, include linear and branched $C_1$-$C_6$ alcohols, such as ethanol, propanol, isopropanol, butanol, hexanol, and mixtures thereof; aromatic alcohols, such as benzyl alcohol, cycloaliphatic alcohols, such as cyclohexanol, and the like; saturated $C_{12}$-$C_{30}$ fatty alcohol, such as lauryl alcohol, myristyl alcohol, cetyl alcohol, stearyl alcohol, behenyl alcohol, and the like. Non-limiting examples of polyols include polyhydroxy alcohols, such as glycerin, propylene glycol, butylene glycol, hexylene glycol, $C_2$-$C_4$ alkoxylated alcohols and $C_2$-$C_4$ alkoxylated polyols, such as ethoxylated, propoxylated, and butoxylated ethers of alcohols, diols, and polyols having about 2 to about 30 carbon atoms and 1 to about 40 alkoxy units, polypropylene glycol, polybutylene glycol, and the like. Non-limiting examples of non-aqueous auxiliary solvents include silicones, and silicone derivatives, such as cyclomethicone, and the like, aliphatic solvents such as cyclohexane and heptane, ketones such as acetone and methyl ethyl ketone, and mixtures thereof; ethers such as diethyl ether, dimethoxymethane, and mixtures thereof, natural and synthetic oils and waxes, such as vegetable oils, plant oils, animal oils, essential oils, mineral oils, $C_7$-$C_{40}$ isoparaffins, alkyl carboxylic esters, such as ethyl acetate, amyl acetate, ethyl lactate, and the like, jojoba oil, shark liver oil, and the like. Mixtures of the foregoing solvents can also be utilized in combination with the polygalactomannan substituted compositions as variously described above. Some of the foregoing non-aqueous auxiliary solvents may also function as conditioners and emulsifiers.

Surfactants are generally employed as cleansing agents, emulsifying agents, foam boosters, hydrotropes and suspending agents. The polygalactomannan substituted compositions as variously described above may be employed in formulations containing all classes of surfactants, i.e., anionic surfactants, cationic surfactants, nonionic surfactants, amphoteric surfactants. The term "amphoteric surfactant" as used herein includes zwitterionic surfactants. In addition to the foregoing references, discussions of the classes of surfactants are in Cosmetics & Toiletries® C&T Ingredient Resource Series, "Surfactant Encyclopedia", 2nd Edition, Rieger (ed), Allured Publishing Corporation (1996); Schwartz, et al., Surface Active Agents, Their Chemistry and Technology, published 1949; and Surface Active Agents and Detergents, Volume II, published 1958, Interscience Publishers; each incorporated herein by reference.

Surprisingly, polygalactomannan substituted compositions as variously described above are useful as thickeners and deposition aids in compositions containing a relatively high concentration (about 6-40 weight percent) of anionic surfactant, such as shampoos and two-in-one type liquid conditioning/cleansers for hair and body (bath) products.

Anionic surfactants include substances having a negatively charged hydrophobe or that carry a negative charge when the pH is elevated to neutrality or above, such as acylamino acids, and salts thereof, for example, acylglutamates, acyl peptides, sarcosinates, and taurates; carboxylic acids, and salts thereof, for example, alkanolic acids and alkanoates, ester carboxylic acids, and ether carboxylic acids; phosphoric acid ester and salts thereof; sulfonic acids and salts thereof, for example, acyl isethionates, alkylaryl sulfonates, alkyl sulfonates, and sulfosuccinates; and sulfuric acid esters, such as alkyl ether sulfates and alkyl sulfates.

Non-limiting examples of anionic surfactants include mono-basic salts of acylglutamates that are slightly acidic in aqueous solution, such as sodium acylglutamate and sodium hydrogenated tallow glutamate; salts of acyl-hydrolyzed protein, such as potassium, palmitoyl hydrolyzed milk protein, sodium cocoyl hydrolyzed soy protein, and TEA-abietoyl hydrolyzed collagen; salts of acyl sarcosinates, such as ammonium myristoyl sarcosine, sodium cocoyl sarcosinate, and TEA-lauroyl sarcosinate; salts of sodium methyl acyltaurates, such as sodium lauroyl taurate and sodium methyl cocoyl taurate; alkanoic acids and alkanoates, such as fatty acids derived from animal and vegetable glycerides that form water-soluble soaps and water-insoluble emulsifying soaps, including sodium stearate, aluminum stearate, and zinc undecylenate; ester carboxylic acids, such as dinonoxynol-9-citrate; salts of acyl lactylates such as calcium stearoyl lactylate and laureth-6 citrate; ethercarboxylic acids derived from ethyoxylated alcohols or phenols having varying lengths of polyoxyethylene chains, such as nonoxynol-8 carboxylic acid, and sodium trideceth-13 carboxylate; mono- and di-esters of phosphoric acid and their salts, such as phospholipids, dilaureth-4-phosphate, DEA-oleth-10 phosphate and triethanolamine lauryl phosphate; salts of acylisethionate, such as sodium cocoyl isethionate; alkylarylbenzene sulfonates, such as alpha-olefin sulfonate (AOS) and alkali metal, alkaline earth metal, and alkanolamine salts thereof, and sodium dodecylbenzene sulfonate; alkyl sulfonates, such as sodium $C_{12}$-$C_{14}$ olefin sulfonate, sodium cocomonoglyceride sulfonate, sodium $C_{12}$-$C_{15}$ pareth-15 sulfonate, and sodium lauryl sulfoacetate; sulfosuccinates, such as mono- and di-esters of sulfosuccinic acid, salts thereof and alkoxylated alkyl and alkylamido derivatives thereof, such as di-$C_4$-$C_{10}$ alkyl sodium sulfosuccinate, disodium laureth sulfosuccinate, disodium oleamido MEA-sulfosuccinate, and disodium $C_{12}$-$C_{15}$ pareth sulfosuccinate; alkyl ether sulfates, such as sodium and ammonium lauryl ether sulfate (having about 1 to about 12 moles ethylene oxide); alkyl sulfates, such as sodium, ammonium and triethanolamine salts of $C_{12}$-$C_{18}$ alkylsulfates, sodium $C_{12}$-$C_{14}$ olefin sulfates, sodium laureth-6 carboxylate, sodium $C_{12}$-$C_{18}$ pareth sulfate, and the like.

Cationic surfactants can have a hydrophobe that carries a positive charge or that is uncharged at pH values close to neutrality or lower, such as alkylamines, alkyl imidazolines, ethoxylated amines, and quaternary ammonium compounds. Cationic surfactants used in cosmetics are preferably N-derivatives and the neutralizing anion may be inorganic or organic. Among the cationic surfactant materials useful herein are quaternary ammonium compounds corresponding to the general formula: $(R^{10}R^{11}R^{12}R^{13}N^+)E^-$, wherein each of $R^{10}$, $R^{11}$, $R^{12}$, and $R^{13}$ are independently selected from an aliphatic group having from 1 to about 22 carbon atoms, or an aromatic, alkoxy, polyoxyalkylene, alkylamido, hydroxyalkyl, aryl or alkylaryl group having 1 to about 22 carbon atoms in the alkyl chain; and E is a salt-forming anion such as those selected from halogen, (e.g. chloride, bromide), acetate, citrate, lactate, glycolate, phosphate, nitrate, sulfate, and alkylsulfate. The aliphatic groups can contain, in addition to carbon and hydrogen atoms, ether linkages, ester linkages, and other groups such as amino groups. The longer chain aliphatic groups, e.g., those of about 12 carbons, or higher, can be saturated or unsaturated.

Alkylamines can be salts of primary, secondary and tertiary fatty $C_{12}$-$C_{22}$ alkylamines, substituted or unsubstituted, and substances sometimes referred to as "amidoamines". Non-limiting examples of alkylamines and salts thereof include dimethyl cocamine, dimethyl palmitamine, dioctylamine, dimethyl stearamine, dimethyl soyamine, soyamine, myristyl amine, tridecyl amine, ethyl stearylamine, N-tallowpropane diamine, ethoxylated stearylamine, dihydroxy ethyl stearylamine, arachidylbehenylamine, dimethyl lauramine, stearylamine hydrochloride, soyamine chloride, stearylamine formate, N-tallowpropane diamine dichloride, and amodimethicone (INCI name for a silicone polymer and blocked with amino functional groups, such as aminoethylamino propylsiloxane). Non-limiting examples of amidoamines and salts thereof include stearamido propyl dimethyl amine, stearamidopropyl dimethylamine citrate, palmitamidopropyl diethylamine, and cocamidopropyl dimethylamine lactate. Other cationic surfactants include distearyldimonium chloride, dicetyldimonium chloride, guar hydroxypropyltrimonium chloride, and the like. At low pH, amine oxides may protonate and behave similarly to N-alkyl amines.

Non-limiting examples of alkyl imidazolines include alkyl hydroxyethyl imidazoline, such as stearyl hydroxyethyl imidazoline, coco hydroxyethyl imidazoline, ethyl hydroxymethyl oleyl oxazoline, and the like. Non-limiting examples of ethyoxylated amines include PEG-cocopolyamine, PEG-15 tallow amine, quaternium-52, and the like.

Quaternary ammonium compounds can be selected from monomeric or polymeric materials containing at least one nitrogen atom that is linked covalently to four alkyl and/or aryl substituents, and the nitrogen atom remains positively charged regardless of the environmental pH. Quaternary ammonium compounds comprise a large number of substances that are used extensively as surfactants, conditioners, antistatic agents, and antimicrobial agents and include, alkylbenzyldimethyl ammonium salts, alkyl betaines, heterocyclic ammonium salts, and tetraalkylammonium salts. Long-chain (fatty) alkylbenzyldimethyl ammonium salts are preferred as conditioners, as antistatic agents, and as fabric softeners, discussed in more detail below. Other quaternary ammonium compounds include quaternary ammonium silicones. While various quaternary ammonium compounds are listed for a specific purpose, one of ordinary skill will recognize that the quaternary ammonium compounds described here and throughout the specification can serve more than one function.

Non-limiting examples of alkylbenzyldimethylammonium salts include stearalkonium chloride, benzalkonium chloride, quaternium-63, olealkonium chloride, didecyldimonium chloride, and the like. Alkyl betaine compounds include alkylamidopropyl betaine, alkylamidopropyl hydroxysultaine, and sodium alkylamido propyl hydroxyphostaine. Non-limiting examples of alkyl betaine compounds include oleyl betaine, coco-betaine, cocoamidopropyl betaine, coco-hydroxy sultaine, coco/oleamidopropyl betaine, coco-sultaine, cocoamidopropylhydroxy sultaine, and sodium lauramidopropyl hydroxyphostaine. Heterocyclic ammonium salts include alkylethyl morpholinium ethosulfate, isostearyl ethylimidonium ethosulfate, and alkylpyridinium chlorides, and are generally used as emulsifying agents. Non-limiting examples of heterocyclic ammonium salts include cetylpyridinium chloride, isostearylethylimidonium ethosulfate, and the like. Non-limiting examples of tetraalkylammonium salts include cocamidopropyl ethyldimonium ethosulfate, hydroxyethyl cetyldimonium chloride, quaternium-18, and cocodimonium hyroxypropyl hydrolyzed protein, such as hair keratin, and the like.

The polygalactomannan substituted compositions as variously described above are surprisingly compatible with cationic surfactants and other cationic compounds suitable as antistatic agents, such as those employed in hair care and fabric care products. The term "antistatic agents" as used herein refers to ingredients that alter the electrical properties of cosmetic raw materials or of human body surfaces (skin, hair, etc.) and textiles, for example, by reducing their tendency to acquire an electrical charge and thus, can condition hair, skin and fabrics. The cationic compatibility of the polygalactomannan substituted compositions as variously described above makes them suitable for incorporation into formulations containing antistatic agents typically employed in hair care compositions, such as shampoos, post-shampoo conditioning rinses, hair sprays, hair dressings and the like. The antistatic agent can be employed in amounts up to about 30 weight percent of the final composition, but is not limited thereto.

Antistatic agents include, but are not limited to, quaternary ammonium compounds, protein derivatives, synthetic quaternary ammonium polymers, amines, protonated amine oxides, betaines, and the like, which may act as antistatic agents in specific formulations and under controlled pH conditions in addition to any surfactant properties imparted by such materials. In addition to antistatic agents previously discussed, non-limiting examples of quaternary ammonium compounds useful as antistatic agents are acetamidopropyl trimonium chloride, behenamidopropyl dimethylamine, behenamidopropyl ethyldimonium ethosulfate, behentrimonium chloride, cetethyl morpholinium ethosulfate, cetrimonium chloride, cocoamidopropyl ethyldimonium ethosulfate, dicetyldimonium chloride, dimethicone hydroxypropyl trimonium chloride, hydroxyethyl behenamidopropyl dimonium chloride, quaternium-26, quaternium-27, quaternium-53, quaternium-63, quaternium-70, quaternium-72, quaternium-76 hydrolyzed collagen, PPG-9 diethylmonium chloride, PPG-25 diethylmonium chloride, PPG-40 diethylmonium chloride, stearalkonium chloride, stearamidopropyl ethyl dimonium ethosulfate, steardimonium hydroxypropyl hydrolyzed wheat protein, steardimonium hydroxypropyl hydrolyzed collagen, wheat germamidopropalkonium chloride, wheat germamidopropyl ethyldimonium ethosulfate, and the like.

Synthetic quaternary ammonium polymers include but are not limited to film-forming polymers and conditioning polymers. Non-limiting examples of synthetic quaternary ammonium polymers include polymers and copolymers of dimethyl diallyl ammonium chloride, such as polyquaternium-4, polyquaternium-6, polyquaternium-7, polyquaternium-22, polyquaternium-10, polyquaternium-11 polyquaternium-15, polyquaternium-16, polyquaternium-24, polyquaternium-28, polyquaternium-32, polyquaternium-33, polyquaternium-35, polyquaternium-37, polyquaternium-39, polyquaternium-44, polyquaternium-55, polyquaternium-56, polyquaternium-67, polyquaternium-68, polyquaternium-69, polyquaternium-70, polyquaternium-71, polyquaternium-72, polyquaternium-73, polyquaternium-74, polyquaternium-75, polyquaternium-76, polyquaternium-83, polyquaternium-84, polyquaternium-85, polyquaternium-86, polyquaternium-87, polyquaternium-88, polyquaternium-89, polyquaternium-91, polyquaternium-98, PEG-2-cocomonium chloride, quaternium-52, and the like.

The term "hair setting composition" encompasses products comprising at least one polymer of the present invention as a hair setting agent, which are applied to the hair (wet or dry) before, during or after configuring the hair into the shape (curly or straight) desired, without limitation as to product form.

The polygalactomannan substituted compositions as variously described above are surprisingly useful in hair setting and hair styling compositions as the sole film-forming, rheology modifying, conditioning fixative agent. The polygalactomannan substituted compositions as variously described above are also useful in combination with commercially available auxiliary hair fixative polymers, such as nonionic, cationic, and amphoteric hair setting polymers, cationic conditioning polymers, and combinations thereof. Conventional polymeric hair fixative and hair styling polymers, well known in the art, include natural gums and resins and neutral or anionic polymers of synthetic origin. Listings of commercially available hair fixative and conditioning fixative polymers can be readily found in the INCI Dictionary, in supplier websites, and in the trade literature. See, for example, the Polymer Encyclopedia published in Cosmetics & Toiletries®, 117(12), December 2002 (Allured Publishing Corporation, Carol Stream, Ill.), the relevant disclosures of which are incorporated herein by reference.

Suitable commercially available nonionic polymers (i.e., neutral) used as hair styling or fixative polymers include, without limitation thereto, polyvinylpyrrolidone (PVP), polyvinylpyrrolidone/vinylacetate copolymer (PVP/VA), and the like. Commercially available cationic fixative polymers include, without limitation thereto, polymers having the INCI name, polyquaternium, such as polyquaternium-4, a diallyldimonium chloride/hydroxyethylcellulose copolymer (such as CELQUAT® H-100, Akzo Nobel); polyquaternium-11, a quaternized vinyl pyrrolidone/dimethylaminoethyl methacrylate copolymer (such as GAFQUAT® 734, 755, 755N, ISP); polyquaternium-16, a quaternized vinyl pyrrolidone/vinylimidazolium chloride copolymer (such as LUVIQUAT® FC-370, BASF); polyquaternium-28, a vinylpyrrolidone/methacrylamidopropyltrimethylammonium chloride copolymer (such as GAFQUAT® HS-100, ISP); polyquaternium-46, a quaternized vinylcaprolactam/vinylpyrrolidone/methylvinylimidazolium methosulfate copolymer; polyquaternium-55, a quaternized vinylpyrrolidone/dimethylaminopropylmethylacrylamide/lauryldimethylpropylmethacrylamidoammonium chloride copolymer (such as STYLEZE™ W, ISP), and the like; and amino-substituted polymers which are cationic under acidic pH conditions, such as vinylcaprolactam/PVP/dimethylaminoethylmethacrylate copolymer (such as GAFFIX® VC-713, ISP); PVP/dimethylaminoethylmethacrylate copolymer (such as Copolymer 845, ISP), PVP/DMAPA acrylates copolymer (such as STYLEZE™ CC-10, ISP), the pyrrolidone carboxylic acid salt of chitosan, having the INCI name, Chitosan salts (i.e. Chitosan PCA-KYTAMER® PC, Amerchol), and the like.

Suitable amphoteric fixative polymers include, without limitation thereto, octylacryamide/acrylates/butylaminoethylmethacrylate copolymer (such as the AMPHOMER® polymers, Akzo Nobel), acrylates/lauryl acrylate/stearyl acrylate/ethylamine oxide methacrylate copolymers (such as the DIAFORMER® polymers, Clariant Corp.), and the like.

Suitable commercial conditioning polymers include polymeric quaternary ammonium salts such as, without being limited thereto, polyquaternium-7, a polymeric quaternary ammonium salt of acrylamide and dimethyl diallylammonium chloride monomers (such as MACKERNIUM™-007, McIntyre Group, Ltd.); polyquaternium-10, a polymeric quaternary ammonium salt of hydroxyethylcellulose reacted with a trimethylammonium substituted epoxide (such as the UCARE® Polymers JR, LK, LR, SR series, Amerchol and CELQUAT® SC series, Akzo Nobel); polyquaternium-39, a polymeric quaternary ammonium salt of acrylic acid, diallyl dimethylammonium chloride and acrylamide (such as the MERQUAT® and MERQUAT® Plus polymers, Ondeo Nalco); quaternized derivatives of natural gums, e.g., guar hydroxypropyltrimonium chloride (such as the N-HANCE® and Supercol® polymers, Ashland Inc.), and the like.

A number of quaternary ammonium compounds are used for fabric conditioning and fabric care, generally referred to as fabric softening agents, and are typically employed in amounts of up to about 20 weight percent of the total weight of the formulation, but are not limited thereto. Fabric softening agents useful in combination with the polygalactomannan substituted compositions as variously described above generally include long-chain alkylated quaternary ammonium compounds such as dialkyldimethyl quaternary ammonium compounds, imidazoline quaternary compounds, amidoamine quaternary compounds, dialkyl ester quat derivatives of dihydroxypropyl ammonium compounds; dialkyl ester quat derivatives of methyltriethanol ammonium compounds, ester amide amine compounds, and diester quat derivatives of dimethyldiethanol ammonium chloride, as described in the review article by Whalley, "Fabric Conditioning Agents", HAPPI, pp. 55-58 (February 1995), incorporated herein by reference.

In addition to the previously discussed antistatic agents, non-limiting examples of dialkyldimethyl quaternary ammonium compounds, include N,N-dioleyl-N,N-dimethylammonium chloride, N,N-ditallowyl-N,N-dimethylammonium ethosulfate, N,N-di(hydrogenated-tallowyl)-N,N-dimethylammonium chloride, and the like. Non-limiting examples of imidazoline quaternary compounds include 1-N-methyl-3-N-tallowamidoethylimidazolium chloride, 3-methyl-1-tallowylamidoethyl-2-tallowylimidazolinium methylsulfate, available from Witco Chemical Company under the tradename VARISOFT® 475, and the like. Non-limiting examples of amidoamine quaternary compounds include N-alkyl-N-methyl-N,N-bis(2-tallowamidoethyl)ammonium salts where the alkyl group can be methyl, ethyl, hydroxyethyl, and the like. Non-limiting examples of dialkyl ester quat derivatives of dihydroxypropyl ammonium compounds include 1,2-ditallowoyloxy-3-N,N,N-trimethylammoniopropane chloride, 1,2-dicanoloyloxy-3-N,N,N-trimethylammoniopropane chloride, and the like.

In addition, other types of long chain (e.g. natural oil and fatty acid-derived) alkylated quaternary ammonium compounds are suitable fabric softening agents, including, but not limited, to N,N-di(alkyloxyethyl)-N,N-dimethylammonium salts such as N,N-di(tallowyloxyethyl)-N,N-dimethylammonium chloride, N,N-di(canolyloxyethyl)-N,N-dimethylammonium chloride, and the like; N,N-di(alkyloxyethyl)-N-methyl-N-(2-hydroxyethyl)ammonium salts such as N,N-di(tallowyloxyethyl)-N-methyl-N-(2-hydroxyethyl) ammonium chloride, N,N-di(canolyloxyethyl)-N-methyl-N-(2-hydroxyethyl)ammonium chloride, and the like; N,N-di (2-alkyloxy-2-oxoethyl)-N,N-dimethylammonium salts, such as N,N-di(2-tallowyloxy-2-oxoethyl)-N,N-dimethylammonium chloride, N,N-di(2-canolyloxy-2-oxoethyl)-N, N-dimethylammonium chloride, and the like; N,N-di(2-alkyloxyethylcarbonyloxyethyl)-N,N-dimethylammonium salts, such as N,N-di(2-tallowyloxyethylcarbonyloxyethyl)-N,N-dimethylammonium chloride, N,N-di(2-canolyloxyethylcarbonyloxyethyl)-N,N-dimethylammonium chloride, and the like; N-(2-alkanoyloxy-2-ethyl)-N-(2-alkyloxy-2-oxoethyl)-N,N-dimethyl ammonium salts, such as N-(2-tallowoyloxy-2-ethyl)-N-(2-tallowyloxy-2-oxoethyl)-N,N- dimethyl ammonium chloride, N-(2-canoyloxy-2-ethyl)-N-(2-canolyloxy-2-oxoethyl)-N,N-dimethyl ammonium chloride, and the like; N,N,N-tri(alkyloxyethyl)-N-methyl ammonium salts, such as N,N,N-tri(tallowyloxyethyl)-N-methylammonium chloride, N,N,N-tri(canolyloxyethyl)-N-methylammonium chloride, and the like; N-(2-alkyloxy-2-oxoethyl)-N-alkyl-N,N-dimethyl ammonium salts, such as N-(2-tallowyloxy-2-oxoethyl)-N-tallowyl-N,N-dimethyl ammonium chloride, N-(2-canolyloxy-2-oxoethyl)-N-canolyl-N,N-dimethyl ammonium chloride, and the like.

Preferably, the long-chain alkyl groups are derived from tallow, canola oil, or from palm oil, however, other alkyl groups derived from soybean oil and coconut oil, for example, are also suitable, as are lauryl, oleyl, ricinoleyl, stearyl, palmityl, and like fatty alkyl groups. The quaternary ammonium salt compounds can have any anionic group as a counter-ion, for example, chloride, bromide, methosulfate (i.e. methylsulfate), acetate, formate, sulfate, nitrate, and the like.

Examples of preferred quaternary ammonium fabric softening compounds include N-methyl-N,N-bis(tallowamidoethyl)-N-(2-hydroxyethyl)ammonium methylsulfate and N-methyl-N,N-bis(hydrogenated-tallowamidoethyl)-N-(2-hydroxyethyl) ammonium methylsulfate, each of which materials are available from Witco Chemical Company under the trade names VARISOFT® 222 and VARISOFT® 110, respectively; dialkyl esterquat derivatives of methyltriethanol ammonium salts such as the DEHYQUART® AU series of bis(acyloxyethyl)hydroxyethylmethylammonium methosulfate esterquats available from Cognis, such as DEHYQUART® AU35, AU46, AU56, and the like; and N,N-di(tallowoyloxyethyl)-N,N-dimethylammonium chloride, where the tallow chains are at least partially unsaturated. Other preferred fabric softening agents include the well-known dialkyldimethyl ammonium salts such as N,N-ditallowyl-N,N-dimethyl ammonium methylsulfate, N,N-di(hydrogenated-tallowyl)-N,N-dimethyl ammonium chloride, N,N-distearyl-N,N-dimethyl ammonium chloride, N,N-dibehenyl-N,N-dimethylammonium chloride, N,N-di(hydrogenated tallow)-N,N-dimethyl ammonium chloride (trade name ADOGEN® 442), N,N-ditallowyl-N,N-dimethyl ammonium chloride (trade name ADOGEN® 470, PRAEPAGEN® 3445), N,N-distearyl-N,N-dimethyl ammonium chloride (trade name AROSURF® TA-100), all available from Witco Chemical Company; N,N-dibehenyl-N,N-dimethyl ammonium chloride, sold under the trade name KEMAMINE® Q-2802C by Humko Chemical Division of Witco Chemical Corporation; and N,N-dimethyl-N-stearyl-N-benzylammonium chloride sold under the trade names VARISOFT® SDC by Witco Chemical Company and AMMONYX® 490 by Onyx Chemical Company.

Any of the foregoing fabric softening agents, and mixtures thereof, can be utilized in combination with the polygalactomannan substituted compositions as variously described above, particularly in laundry and fabric care products. For ester-containing fabric softening agents, the pH of the compositions can influence the stability of the fabric softening agents, especially in prolonged storage conditions. The pH, as defined in the present context, is measured in the neat compositions at about 20° C. Preferably, the pH of the composition is less than about 6. For optimum hydrolytic stability of these compositions, the pH is preferably in the range of from about 2 to about 5, more preferably about 2.5 to about 3.5.

Non-limiting examples of protein derivatives include cocodimonium hydroxypropyl hydrolyzed casein, cocodimonium hydroxypropyl hydrolyzed collagen, cocodimonium hydroxypropyl hydrolyzed hair keratin, cocodimonium hydroxypropyl hydrolyzed rice protein, cocodimonium hydroxypropyl hydrolyzed silk, cocodimonium hydroxypropyl hydrolyzed soy protein, cocodimonium hydroxypropyl hydrolyzed wheat protein, cocodimonium hydroxypropyl hydrolyzed silk amino acids, hydroxypropyl trimonium hydrolyzed collagen, hydroxypropyl trimonium hydrolyzed keratin, hydroxypropyl trimonium hydrolyzed silk, hydroxypropyl trimonium hydrolyzed rice bran, hydroxypropyl trimonium hydrolyzed soy protein, hydroxypropyl trimonium hydrolyzed vegetable protein, hydroxypropyl trimonium hydrolyzed wheat protein, hydrolyzed wheat protein, hydrolyzed sweet almond protein, hydrolyzed rice protein, hydrolyzed soy protein, hydrolyzed milk protein, hydrolyzed vegetable protein, hydrolyzed keratin, hydrolyzed collagen, hydrolyzed wheat gluten, potassium cocoyl hydrolyzed collagen, hydroxypropyl trimonium hydrolyzed collagen, cocodimonium hydroxypropyl hydrolyzed milk protein, lauryldimonium hydroxypropyl hydrolyzed wheat protein, lauryldimonium hydroxypropyl hydrolyzed collagen, keratin amino acids, collagen amino acids, soyethyldimonium ethosulfate, soyethyl morpholinium ethosulfate, and the like.

Nonionic surfactants are generally uncharged amphiphiles and usually are alkoxylated to varying degrees. Classes of nonionic surfactants include alcohols, alkanolamides, amine oxides, esters, and ethers. Nonionic alcohols are usually hydroxy derivatives of long-chain $C_8$-$C_{18}$ alkane hydrocarbons, such as cetearyl alcohol, hydrogenated tallow alcohol, lanolin alcohols, alkanolamides, and the like. Alkanolamides contain at least one alkoxyl or one polyoxyethylene grouping and include alkanol-derived amides, such as acylamide DEA, N-alkyl pyrrolidone, palmamide MEA, peanutamide MIPA, and the like and ethoxylated amides, such as PEG-50 tallow amide. Amine oxides include alkylamine oxides, such as lauramine oxide; and acylamidopropyl morpholine oxides, such as cocamidopropylamine oxide; and the like. Esters include ethoxylated carboxylic acids, such as PEG-8 dilaurate, PEG-8 laurate, and the like; ethoxylated glycerides, such as PEG-4 castor oil, PEG-120 glyceryl stearate, triolein PEG-6 esters, and the like; glycol esters and derivatives thereof, such as glycol stearate SE, propylene glycol ricinoleate, and the like; monoglycerides, such as glyceryl myristate, glyceryl palmitate lactate, and the like; polyglyceryl esters, such as polyglyceryl-6-distearate, polyglyceryl-4 oleyl ether, and the like, polyhydric alcohol esters and ethers, such as methyl gluceth-20 sesquistearate, sucrose distearate; and the like; sorbitan/sorbitol esters, such as polysorbate-60, sorbitan sequiisostearate, and the like; and triesters of phosphoric acid, such as trideceth-3 phosphate, trioleth-8 phosphate, and the like. Ethers include ethoxylated alcohols, such as ceteareth-10, nonoxynol-9, and the like; ethoxylated lanolin, such as PEG-20 lanolin, PPG-12-PEG-65 lanolin oil, and the like; ethoxylated polysiloxanes, such as dimethicone copolyol, and the like; propoxylated POE ethers, such as meroxapol 314, poloxamer 122, PPG-5-ceteth-20, and the like; and alkyl polyglycosides, such as lauryl glucose, and the like.

Nonionic surfactants can be used as emulsifiers, suspending agents, solubilizers, foam boosters, and in some cases, as hydrotropes. Non-limiting examples of generally preferred nonionic surfactants include linear or branched alcohol ethoxylates, $C_8$-$C_{12}$ alkylphenol alkoxylates, such as octylphenol ethoxylates, polyoxyethylene polyoxypropylene block copolymers, and the like; $C_8$-$C_{22}$ fatty acid esters of polyoxyethylene glycol mono- and di-glycerides; sorbitan esters and ethoxylated sorbitan esters; $C_8$-$C_{22}$ fatty acid glycol esters; ethoxylated hydrogenated castor oils; block copolymers of ethylene oxide and propylene oxide; and the like. Non-limiting examples of surfactant foam boosters or hydrotropes include alkanolamides, such as acetamide MEA, monoethanolamide, diethanolamide, cocamide DEA, isopropanolamide, and the like; amine oxides, such as hydrogenated tallowamine oxide; short chain alkyl aryl sulfonates, such as sodium toluene sulfonate; sulfosuccinates, such as disodium stearyl sulfosuccinate; and the like.

Amphoteric and zwitterionic surfactants are those compounds that have the capacity of behaving either as an acid or a base, by carrying a positive charge in strongly acidic media, carrying a negative charge in strongly basic media, and forming zwitterionic species at intermediate pH. The major classes of amphoteric surfactants are acyl/dialkyl ethylenediamines and derivatives thereof, such as disodium cocoamphocarboxymethylhydroxy-propyl sulfate, disodium cocamphodipropionate, sodium cocoamphoacetate, sodium lauroampho PG-acetatephosphate, sodium tallowamphopropionate, sodium undecylenoamphopropionate, and the like; and N-alkylamino acids, such as aminopropyl laurylglutamide, dihydroxyethyl soya glycinate, lauraminopropionic acid, and the like.

Some suitable zwitterionic surfactants include those broadly described as derivatives of aliphatic quaternary ammonium, phosphonium, and sulfonium compounds, wherein which the aliphatic radicals can be straight chain or branched, and wherein one of the aliphatic substituents contains about 8 to about 18 carbon atoms and another substituent contains an anionic water-solubilizing group, such as carboxy, sulfonate, sulfate, phosphate, phosphonate, and the like. Classes of zwitterionics include alkylamino sulfonates, alkyl betaines and alkylamido betaines, such as stearamidopropyldimethylamine, diethylaminoethylstearamide, dimethylstearamine, dimethylsoyamine, soyamine, myristylamine, tridecylamine, ethylstearylamine, N-tallowpropane diamine, ethoxylated (5 moles ethylene oxide) stearylamine, dihydroxy ethyl stearylamine, arachidylbehenylamine, and the like. Some suitable betaine surfactants include but are not limited to alkyl betaines, alkyl amidopropyl betaines, alkyl sulphobetaines, alkyl glycinates, alkyl carboxyglycinates, alkyl amphopropionates, alkyl amidopropyl hydroxysultaines, acyl taurates, and acyl glutamates, wherein the alkyl and acyl groups have from 8 to 18 carbon atoms. Non-limiting examples of preferred amphoteric surfactants include cocamidopropyl betaine, sodium cocoamphoacetate, cocamidopropyl hydroxysultaine, and sodium cocoamphopropionate, which are particularly suitable as mild-type cleansers for skin and hair.

Exemplary emulsifiers include but are not limited to $C_{12}$-$C_{18}$ fatty alcohols; alkoxylated $C_{12}$-$C_{18}$ fatty alcohols; $C_{12}$-$C_{18}$ fatty acids; and alkoxylated $C_{12}$-$C_{18}$ fatty acids, the alkoxylates each having from 5 to 40 units of ethylene oxide, propylene oxide, and combinations of ethylene oxide/propylene oxide; $C_8$-$C_{22}$ alkyl mono- and oligoglycosides; ethoxylated sterols; partial esters of polyglycerols; esters and partial esters of polyols having 2 to 6 carbon atoms and saturated and unsaturated fatty acids having 12 to 30 carbon atoms; partial esters of polyglycerols; and organosiloxanes; and combinations thereof.

The fatty alcohols, acids and alkoxylated fatty alcohols and fatty acids are as described in the emollient description above. In one aspect of the invention the fatty alcohols and fatty acids each are ethoxylated with 10 to 30 units of ethylene oxide.

The $C_8$-$C_{22}$ alkyl mono- and oligoglycoside emulsifiers are prepared by reacting glucose or an oligosaccharide with primary fatty alcohols having 8 to 22 carbon atoms. Products which are obtainable under the trademark Plantacare® comprise a glucosidically bonded $C_8$-$C_{16}$ alkyl group on an oligoglucoside residue whose average degree of oligomerization is 1 to 2. Exemplary alkyl glucosides and oligoglycosides are selected from octyl glucoside, decyl glucoside, lauryl glucoside, palmityl glucoside, isostearyl glucoside, stearyl glucoside, arachidyl glucoside and behenyl glucoside, and mixtures thereof.

Exemplary ethoxylated sterols include ethoxylated vegetable oil sterols such as, for example, soya sterols. The degree of ethoxylation is greater than about 5 in one aspect, and at least about 10 in another aspect. Suitable ethoxylated sterols are PEG-10 Soy Sterol, PEG-16 Soy Sterol and PEG-25 Soy Sterol.

The partial esters of polyglycerols have 2 to 10 glycerol units and are esterified with 1 to 4 saturated or unsaturated, linear or branched, optionally hydroxylated $C_8$-$C_{30}$ fatty acid residues. Representative partial esters of polyglycerols include diglycerol monocaprylate, diglycerol monocaprate, diglycerol monolaurate, triglycerol monocaprylate, triglycerol monocaprate, triglycerol monolaurate, tetraglycerol monocaprylate, tetraglycerol monocaprate, tetraglycerol monolaurate, pentaglycerol monocaprylate, pentaglycerol monocaprate, pentaglycerol monolaurate, hexaglycerol monocaprylate, hexaglycerol monocaprate, hexaglycerol monolaurate, hexaglycerol monomyristate, hexaglycerol monostearate, decaglycerol monocaprylate, decaglycerol monocaprate, decaglycerol monolaurate, decaglycerol monomyristate, decaglycerol monoisostearate, decaglycerol monostearate, decaglycerol monooleate, decaglycerol monohydroxystearate, decaglycerol dicaprylate, decaglycerol dicaprate, decaglycerol dilaurate, decaglycerol dimyristate, decaglycerol diisostearate, decaglycerol distearate, decaglycerol dioleate, decaglycerol dihydroxystearate, decaglycerol tricaprylate, decaglycerol tricaprate, decaglycerol trilaurate, decaglycerol trimyristate, decaglycerol triisostearate, decaglycerol tristearate, decaglycerol trioleate, decaglycerol trihydroxystearate, and mixtures thereof.

The saturated $C_{12}$-$C_{30}$ fatty alcohol emulsifiers are as described in the emollient description set forth above. In one aspect of the invention, the fatty alcohol emulsifier is selected from but not limited to cetyl alcohol, stearyl alcohol, arachidyl alcohol, behenyl alcohol and lanolin alcohol or mixtures of these alcohols, and as are obtainable in the hydrogenation of unsaturated vegetable oil and animal fatty acids.

Emulsifiers based on the esters and partial esters of polyols having 2 to 6 carbon atoms and linear saturated and unsaturated fatty acids having 12 to 30 carbon atoms are, for example, the monoesters and diesters of glycerol or ethylene glycol or the monoesters of propylene glycol with saturated and unsaturated $C_{12}$-$C_{30}$ fatty acids.

The partially esterified polyglycerol emulsifiers include 2 to about 10 glycerol units and esterified with 1 to 5 saturated or unsaturated, linear or branched, optionally hydroxylated $C_8$-$C_{30}$ fatty acid residues.

In one aspect of the invention, the emulsifier can be present in an amount ranging from about 0.1 wt. % to about 12 wt. %, from about 0.5 wt. % to about 15 wt. % in another aspect, and from about 1.0 wt. % to about 10 wt. % in a further aspect, based on the total weight of the personal care, home care, health care, and institutional care composition in which they are included.

Suitable emollients include but are not limited to an emollient selected from silicone fluids (e.g., volatile silicone oils and non-volatile silicone oils described below); mineral oils; petrolatums; vegetable oils; fish oils; fatty alcohols; fatty acids; fatty acid and fatty alcohol esters; alkoxylated fatty alcohols; alkoxylated fatty acid esters; benzoate esters; Guerbet esters; alkyl ether derivatives of polyethylene glycols, such as, for example methoxypolyethylene glycol (MPEG); and polyalkylene glycols; lanolin and lanolin derivatives; and the like.

Mineral oils and petrolatums include cosmetic, USP and NF grades and are commercially available from Penreco under the Drakeol® and Penreco® trade names. Mineral oil includes hexadecane and paraffin oil.

Suitable fatty alcohol emollients include but are not limited to fatty alcohols containing 8 to 30 carbon atoms. Exemplary fatty alcohols include capryl alcohol, pelargonic alcohol, capric alcohol, lauryl alcohol, myristyl alcohol, cetyl alcohol, isocetyl alcohol, stearyl alcohol, isostearyl alcohol, cetearyl alcohol, oleyl alcohol, ricinoleyl alcohol, arachidyl alcohol, icocenyl alcohol, behenyl alcohol, and mixtures thereof.

Suitable fatty acid emollients include but are not limited to fatty acids containing 10 to 30 carbon atoms. Exemplary fatty acids are selected from capric acid, lauric acid, myristic acid, palmitic acid, stearic acid, oleic acid, linoleic acid, arachidic acid, behenic acid, and mixtures thereof.

Exemplary of the fatty acid and fatty alcohol ester emollients include but are not limited to hexyl laurate, decyl oleate, isopropyl stearate, isopropyl isostearate, butyl stearate, octyl stearate, cetyl stearate, myristyl myristate, octyldodecyl stearoylstearate, octylhydroxystearate, diisopropyl adipate, isopropyl myristate, isopropyl palmitate, ethyl hexyl palmitate, isodecyl oleate, isodecyl neopentanoate, diisopropyl sebacate, isostearyl lactate, lauryl lactate, diethyl hexyl maleate, PPG-14 butyl ether and PPG-2 myristyl ether propionate, cetearyl octanoate, and mixtures thereof.

Alkoxylated fatty alcohol emollients are ethers formed from the reaction of a fatty alcohol with an alkylene oxide, generally ethylene oxide or propylene oxide. Suitable ethoxylated fatty alcohols are adducts of fatty alcohols and polyethylene oxide. In one embodiment of the invention, the ethoxylated fatty alcohols can be represented by the formula R'—(OCH$_2$CH$_2$)$_{n'}$—OH, wherein R' represents the aliphatic residue of the parent fatty alcohol and n represents the number of molecules of ethylene oxide. In another embodiment of the invention, R' is derived from a fatty alcohol containing 8 to 30 carbon atoms. In one aspect, n' is an integer ranging from 2 to 50, 3 to 25 in another aspect, and 3 to 10 in a further aspect. In a still further aspect, R' is derived from a fatty alcohol emollient set forth above. Exemplary ethoxylated fatty alcohols are but are not limited to capryl alcohol ethoxylate, lauryl alcohol ethoxylate, myristyl alcohol ethoxylate, cetyl alcohol ethoxylate, stearyl alcohol ethoxylate, cetearyl alcohol ethoxylate oleyl alcohol ethoxylate, and, behenyl alcohol ethoxylate, wherein the number of ethylene oxide units in each of the foregoing ethoxylates can range from 2 and above in one aspect, and from 2 to about 150 in another aspect. It is to be recognized that the propoxylated adducts of the foregoing fatty alcohols and mixed ethoxylated/propoxylated adducts of the foregoing fatty alcohols are also contemplated within the scope of the invention. The ethylene oxide and propylene oxide units of the ethoxylated/propoxylated fatty alcohols can be arranged in random or in blocky order.

More specific examples of ethoxylated alcohols are but are not limited to Beheneth 5-30 (the 5-30 meaning the range of repeating ethylene oxide units), Ceteareth 2-100, Ceteth 1-45, Cetoleth 24-25, Choleth 10-24, Coceth 3-10, C9-11 pareth 3-8, C11-15 pareth 5-40, C11-21 Pareth 3-10, C12-13 pareth 3-15, Deceth 4-6, Dodoxynol 5-12, Glycereth 7-26, Isoceteth 10-30, Isodeceth 4-6, Isolaureth 3-6, isosteareth 3-50, Laneth 5-75, Laureth 1-40, Nonoxynol 1-120, Nonylnonoxynol 5-150, Octoxynol 3-70, Oleth 2-50, PEG 4-350, Steareth 2-100, and Trideceth 2-10.

Specific examples of propoxylated alcohols are but are not limited to PPG-10 Cetyl Ether, PPG-20 Cetyl Ether, PPG-28 Cetyl Ether, PPG-30 Cetyl Ether, PPG-50 Cetyl Ether, PPG-2 Lanolin Alcohol Ether, PPG-5 Lanolin Alcohol Ether, PPG-10 Lanolin Alcohol Ether, PPG-20 Lanolin Alcohol Ether, PPG-30 Lanolin Alcohol Ether, PPG-4 Lauryl Ether, PPG-7 Lauryl Ether, PPG-10 Oleyl Ether, PPG-20 Oleyl Ether, PPG-23 Oleyl Ether, PPG-30 Oleyl Ether, PPG-37 Oleyl Ether, PPG-50 Oleyl Ether, PPG-11 Stearyl Ether, PPG-15 Stearyl Ether, PPG-2 Lanolin Ether, PPG-5 Lanolin Ether, PPG-10 Lanolin Ether, PPG-20 Lanolin Ether, PPG-30 Lanolin Ether, and PPG-1 Myristyl Ether.

Specific examples of ethoxylated/propoxylated alcohols are but are not limited to PPG-1 Beheneth-15, PPG-12 Capryleth-18, PPG-2-Ceteareth-9, PPG-4-Ceteareth-12, PPG-10-Ceteareth-20, PPG-1-Ceteth-1, PPG-1-Ceteth-5, PPG-1-Ceteth-10, PPG-1-Ceteth-20, PPG-2-Ceteth-1, PPG-2-Ceteth-5, PPG-2-Ceteth-10, PPG-2-Ceteth-20, PPG-4-Ceteth-1, PPG-4-Ceteth-5, PPG-4-Ceteth-10, PPG-4-Ceteth-20, PPG-5-Ceteth-20, PPG-8-Ceteth-1, PPG-8-Ceteth-2, PPG-8-Ceteth-5, PPG-8-Ceteth-10, PPG-8-Ceteth-20, PPG-2 C12-13 Pareth-8, PPG-2 C12-15 Pareth-6, PPG-4 C13-15 Pareth-15, PPG-5 C9-15 Pareth-6, PPG-6 C9-11 Pareth-5, PPG-6 C12-15 Pareth-12, PPG-6 C12-18 Pareth-11, PPG-3 C12-14 Sec-Pareth-7, PPG-4 C12-14 Sec-Pareth-5, PPG-5 C12-14 Sec-Pareth-7, PPG-5 C12-14 Sec-Pareth-9, PPG-1-Deceth-6, PPG-2-Deceth-3, PPG-2-Deceth-5, PPG-2-Deceth-7, PPG-2-Deceth-10, PPG-2-Deceth-12, PPG-2-Deceth-15, PPG-2-Deceth-20, PPG-2-Deceth-30, PPG-2-Deceth-40, PPG-2-Deceth-50, PPG-2-Deceth-60, PPG-4-Deceth-4, PPG-4-Deceth-6, PPG-6-Deceth-4, PPG-6-Deceth-9, PPG-8-Deceth-6, PPG-14-Deceth-6, PPG-6-Decyltetradeceth-12, PPG-6-Decyltetradeceth-20, PPG-6-Decyltetradeceth-30, PPG-13-Decyltetradeceth-24, PPG-20-Decyltetradeceth-10, PPG-2-Isodeceth-4, PPG-2-Isodeceth-6, PPG-2-Isodeceth-8, PPG-2-Isodeceth-9, PPG-2-Isodeceth-10, PPG-2-Isodeceth-12, PPG-2-Isodeceth-18, PPG-2-Isodeceth-25, PPG-4-Isodeceth-10, PPG-12-Laneth-50, PPG-2-Laureth-5, PPG-2-Laureth-8, PPG-2-Laureth-12, PPG-3-Laureth-8, PPG-3-Laureth-9, PPG-3-Laureth-10, PPG-3-Laureth-12, PPG-4 Laureth-2, PPG-4 Laureth-5, PPG-4 Laureth-7, PPG-4-Laureth-15, PPG-5-Laureth-5, PPG-6-Laureth-3, PPG-25-Laureth-25, PPG-7 Lauryl Ether, PPG-3-Myreth-3, PPG-3-Myreth-11, PPG-20-PEG-20 Hydrogenated Lanolin, PPG-2-PEG-11 Hydrogenated Lauryl Alcohol Ether, PPG-12-PEG-50 Lanolin, PPG-12-PEG-65 Lanolin Oil, PPG-40-PEG-60 Lanolin Oil, PPG-1-PEG-9 Lauryl Glycol Ether, PPG-3-PEG-6 Oleyl Ether, PPG-23-Steareth-34, PPG-30 Steareth-4, PPG-34-Steareth-3, PPG-38 Steareth-6, PPG-1 Trideceth-6, PPG-4 Trideceth-6, and PPG-6 Trideceth-8.

Alkoxylated fatty acid emollients are formed when a fatty acid is reacted with an alkylene oxide or with a pre-formed polymeric ether. The resulting product may be a monoester, diester, or mixture thereof. Suitable ethoxylated fatty acid ester emollients suitable for use are products of the addition of ethylene oxide to fatty acids. The product is a polyethylene oxide ester of a fatty acid. In one aspect, the ethoxylated fatty acid esters can be represented by the formula R''—C(O)O(CH$_2$CH$_2$O)$_{n''}$—H, wherein R'' represents the aliphatic residue of a fatty acid and n represents the number of molecules of ethylene oxide. In another aspect, n" is an integer ranging from 2 to 50, 3 to 25 in another aspect, and 3 to 10 in a further aspect. In still another aspect of the invention, R" is derived from a fatty acid containing 8 to 24 carbon atoms. In a still further aspect, R" is derived from a fatty acid emollient set forth above. It is to be recognized that propoxylated and ethoxylated/propoxylated products of the foregoing fatty acids are also contemplated within the scope of the invention. Exemplary alkoxylated fatty acid esters include but are not limited to capric acid ethoxylate, lauric acid ethoxylate, myristic acid ethoxylate, stearic acid ethoxylate, oleic acid ethoxylate, coconut fatty acid ethoxylate, and polyethylene glycol 400 propoxylated monolaurate, wherein the number of ethylene oxide units in each of the foregoing ethoxylates can range from 2 and above in one aspect, and from 2 to about 50 in another aspect. More specific examples of ethoxylated fatty acids are PEG-8 distearate (the 8 meaning the number of repeating ethylene oxide units), PEG-8 behenate, PEG-8 caprate, PEG-8 caprylate, PEG-8 caprylate/caprate, PEG cocoates (PEG without a number designation meaning that the number of ethylene oxide units ranges from 2 to 50), PEG-15 dicocoate, PEG-2 diisononanoate, PEG-8 diisostearate, PEG-dilaurates, PEG-dioleates PEG-distearates, PEG Ditallates, PEG-isostearates, PEG-jojoba acids, PEG-laurates, PEG-linolenates, PEG-myristates, PEG-oleates, PEG-palmitates, PEG-ricinoleates, PEG-stearates, PEG-tallates, and the like.

Guerbet ester emollients are formed from the esterification reaction of a Guerbet alcohol with a carboxylic acid. Guerbet ester emollients are commercially available from the Noveon Consumer Specialties Division of Lubrizol Advanced Materials, Inc. under product designations G-20, G-36, G-38, and G-66.

Lanolin and lanolin derivatives are selected from lanolin, lanolin wax, lanolin oil, lanolin alcohols, lanolin fatty acids, alkoxylated lanolin, isopropyl lanolate, acetylated lanolin alcohols, and combinations thereof. Lanolin and lanolin derivatives are commercially available from the Noveon Consumer Specialties Division of Lubrizol Advanced Materials, Inc. under the trade names Lanolin LP 108 USP, Lanolin USP AAA, Acetulan™, Ceralan™, Lanocerin™ Lanogel™ (product designations 21 and 41), Lanogene™, Modulan™, Ohlan™, Solulan™ (product designations 16, 75, L-575, 98, and C-24), Vilvanolin™ (product designations C, CAB, L-101, and P).

The emollient(s) can be utilized in an amount ranging from about 0.5 wt. % to about 30 wt. % by weight of the total personal care composition in one aspect 0.1 wt. % to 25 wt. % in another aspect, and 5 wt. % to 20 wt. % in a further aspect. While emollients are generally employed in personal care compositions, they can be employed in home care, health care, and institutional care compositions in the same wt. ratios as set forth for personal care compositions so long as they affect a desired physical attribute (e.g., humectant properties) in such compositions.

Suitable humectants include allantoin, pyrrolidonecarboxylic acid and its salts, hyaluronic acid and its salts, sorbic acid and its salts, urea, lysine, arginine, cystine, guanidine, and other amino acids, polyhydroxy alcohols such as glycerin, propylene glycol, hexylene glycol, hexanetriol, ethoxydiglycol, dimethicone copolyol, and sorbitol, and the esters thereof, polyethylene glycol, glycolic acid and glycolate salts (e.g. ammonium and quaternary alkyl ammonium), lactic acid and lactate salts (e.g. ammonium and quaternary alkyl ammonium), sugars and starches, sugar and starch derivatives (e.g. alkoxylated glucose), panthenols such as dl-panthenol, lactamide monoethanolamine, acetamide monoethanolamine, and the like, and mixtures thereof. In one embodiment, the humectants include the $C_3$-$C_6$ diols and triols, such as glycerin, propylene glycol, hexylene glycol, hexanetriol, and the like, and mixtures thereof. Such suitable humectants typically comprise about 0.1 wt. % to about 25 wt. %, preferably about 0.5 wt. % to about 20 wt. %, and more preferably about 1.0 wt. % to about 15 wt. % of the total weight of the personal care compositions disclosed herein.

A pH adjusting agent or neutralizer can be added to a formulation containing the polygalactomannan substituted compositions as variously described above. Thus, the pH adjusting agent can be utilized in any amount necessary to obtain a desired pH value in the final composition. Non-limiting examples of alkaline pH adjusting agents include alkali metal hydroxides, such as sodium hydroxide, and potassium hydroxide; ammonium hydroxide; organic bases, such as triethanolamine, diisopropylamine, dodecylamine, diisopropanolamine, aminomethyl propanol, cocamine, oleamine, morpholine, triamylamine, triethylamine, tromethamine (2-amino-2-hydroxymethyl)-1,3-propanediol), and tetrakis(hydroxypropyl)ethylenediamine; and alkali metal salts of inorganic acids, such as sodium borate (borax), sodium phosphate, sodium pyrophosphate, and the like, and mixtures thereof. Acidic pH adjusting agents can be organic acids, including amino acids, and inorganic mineral acids. Non-limiting examples of acidic pH adjusting agents include acetic acid, citric acid, fumaric acid, glutamic acid, glycolic acid, hydrochloric acid, lactic acid, nitric acid, phosphoric acid, sodium bisulfate, sulfuric acid, tartaric acid, and the like, and mixtures thereof.

Suitable buffering agents include but are not limited to alkali or alkali earth carbonates, phosphates, bicarbonates, citrates, borates, acetates, acid anhydrides, succinates and the like, such as sodium phosphate, citrate, borate, acetate, bicarbonate, and carbonate.

The pH adjusting agent and/or buffering agent is utilized in any amount necessary to obtain and/or maintain a desired pH value in the composition. In one aspect, a composition in accordance with an embodiment of the invention can contain at least one alkalizing (alkaline pH adjusting agent) or acidifying agent (acidic pH adjusting agent) in amounts from 0.01 to 30 wt. % of the total weight of the composition.

The polygalactomannan substituted compositions as variously described above can be used as a thickener, film former, and deposition aid for promoting the deposition of colorants on hair and skin. Colorants for hair can be temporary, semipermanent or permanent hair dyes or color restorers that pigment the hair gradually. Temporary and semipermanent hair dyes typically are rinses, gels, sprays, shampoos, sticks, and the like, and hair color restorers are typically in the form of hair dressings or emulsions. Permanent hair dyes, and longer-lasting semipermanent hair dyes, are generally two-part products, one part containing the oxidative dye intermediates and dye couplers, and the other part containing stabilized oxidizing agent, usually hydrogen peroxide at about pH 3-4, and are mixed together immediately before use. It is known that such two-part hair dyeing products are formulated with combinations of surfactant ingredients, usually nonionic surfactants or anionic surfactants, to thicken when the dye mixture is prepared. In addition to the foregoing literature, a general discussion of hair dyeing chemistry and compositions is in Brown et al., SCC Monograph, "Permanent Hair Dyes", Society of Cosmetic Chemists (1996), incorporated herein by reference. The polymers of the present invention may be incorporated in one or both of the two-parts of such hair dyeing systems, either as the thickener for the acidic stabilized oxidizing portion or in the non-oxidizing portion to be thickened upon mixing with the acidic portion.

In addition to ingredients discussed above, other ingredients commonly used for antiacne products, facial and body hair bleaches, and antiseptic products include oxidizing agents, such as hydrogen peroxide, benzoyl peroxide, and water-soluble inorganic persulfate compounds such as ammonium persulfate, potassium persulfate, and sodium persulfate.

The polygalactomannan substituted compositions as variously described above are surprisingly useful stabilizers and/or deposition aids for silicone conditioning agents which are commonly used in rinse off hair conditioner products and in shampoo products, such as the so-called "two-in-one" combination cleansing/conditioning shampoos. The conditioning agent is preferably an insoluble silicone conditioning agent. Typically, the conditioning agent will be mixed in the shampoo composition to form a separate, discontinuous phase of dispersed, insoluble particles (also referred to as droplets). The silicone hair conditioning agent phase can be a silicone fluid and can also comprise other ingredients, such as a silicone resin, to improve silicone fluid deposition efficiency or enhance the glossiness of the hair especially when high refractive index (e.g., above about 1.46) silicone conditioning agents are used. The optional silicone hair conditioning agent phase may comprise volatile silicone, nonvolatile silicone, or combinations thereof. The silicone droplets are typically suspended with an optional suspending agent. The silicone conditioning agent particles may comprise volatile silicone, non-volatile silicone, or combinations thereof. Preferred are non-volatile silicone conditioning agents. If volatile silicones are present, they will typically be incidental to their use as a solvent or carrier for commercially available forms of non-volatile silicone materials ingredients, such as silicone gums and resins. The silicone hair conditioning agents for use in the present invention have a viscosity of from about 20 to about 2,000,000 centistokes (1 centistoke equals $1 \times 10^{-6}$ m$^2$/s) in one aspect, from about 1,000 to about 1,800,000 centistokes in another aspect, from about 50,000 to about 1,500,000 in a further aspect, and from about 100,000 to about 1,500,000 centistokes in a still further aspect, as measured at 25° C.

The concentration of the silicone conditioning agent can range from about 0.01% to about 10%, by weight of the composition in which it is included. In another aspect, the amount of silicone conditioning agent ranges from about 0.1% to about 8%, from about 0.1% to about 5% in still another aspect, and from about 0.2% to about 3% by wt. in a further aspect, all based on the total weight of the composition.

In one embodiment, the dispersed silicone conditioning agent particles can have a volume average particle diameter ranging from about 5 μm to about 125 μm. For small particle application to hair, the volume average particle diameters range from about 0.01 μm to about 4 μm in one aspect, from about 0.01 μm to about 2 μm in another aspect, and from about 0.01 μm to about 0.5 μm in still another aspect. For larger particle application to hair, the volume average particle diameters typically range from about 5 μm to about 125 μm in one aspect, from about 10 μm to about 90 μm in another aspect, from about 15 μm to about 70 μm in still another aspect, and from about 20 μm to about 50 μm in a further aspect.

Background material on silicones including sections discussing silicone fluids, gums, and resins, as well as manufacture of silicones, are found in Encyclopedia of Polymer Science and Engineering, vol. 15, 2d ed., pp 204-308, John Wiley & Sons, Inc. (1989), incorporated herein by reference. Silicone fluids are generally described as alkylsiloxane polymers. Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609, which descriptions are incorporated herein by reference.

Silicone fluids include silicone oils, which are flowable silicone materials having a viscosity, as measured at 25° C. of less than 1,000,000 cSt, and typically range from about 5 cSt to about 1,000,000 cSt. Suitable silicone oils include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

Silicone oils include polyalkyl, polyaryl siloxanes, or polyalkylaryl siloxanes which conform to the following formula:

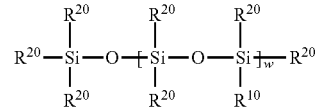

wherein $R^{20}$ is aliphatic, independently selected from alkyl, alkenyl, and aryl, $R^{20}$ can be substituted or unsubstituted, and w is an integer from 1 to about 8,000. Suitable unsubstituted $R^{20}$ groups for use in the personal cleansing compositions described herein include, but are not limited to: alkoxy, aryloxy, alkaryl, arylalkyl, arylalkenyl, alkamino, and ether-substituted, hydroxyl-substituted, and halogen-substituted aliphatic and aryl groups. Suitable $R^{20}$ groups also include cationic amines and quaternary ammonium groups.

In one embodiment of the invention, exemplary $R^{20}$ alkyl and alkenyl substituents range from $C_1$-$C_5$ alkyl and alkenyl, from $C_1$-$C_4$ in another aspect, from $C_1$-$C_2$ in a further aspect. The aliphatic portions of other alkyl-, alkenyl-, or alkynyl-containing groups (such as alkoxy, alkaryl, and alkamino) can be straight or branched chains, and range from $C_1$-$C_5$ in one aspect, from $C_1$-$C_4$ in another aspect, and from $C_1$-$C_2$ in a further aspect. As discussed above, the $R^{20}$ substituents can also contain amino functionalities (e.g. alkamino groups), which can be primary, secondary or tertiary amines or quaternary ammonium. These include mono-, di- and tri-alkylamino and alkoxyamino groups, wherein the aliphatic portion chain length is as described above.

Exemplary siloxanes are polydimethyl siloxane, polydiethylsiloxane, and polymethylphenylsiloxane. These siloxanes are available, for example, from the General Electric Company in their Viscasil R and SF 96 series, and from Dow Corning marketed under the Dow Corning 200 series. Exemplary polyalkylaryl siloxane fluids that may be used, include, for example, polymethylphenylsiloxanes. These siloxanes are available, for example, from the General Electric Company as SF 1075 methyl phenyl fluid or from Dow Corning as 556 Cosmetic Grade Fluid.

Cationic silicone fluids are also suitable for use with the polygalactomannan substituted compositions as variously described above. The cationic silicone fluids can be represented, but are not limited, to the general formula):

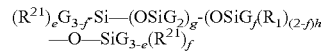

wherein G is hydrogen, phenyl, hydroxy, or $C_1$-$C_8$ alkyl, preferably methyl; e is 0 or an integer having of from 1 to 3; f is 0 or 1; g is a number from 0 to 1,999; h is an integer from 1 to 2,000, preferably from 1 to 10; the sum of g and h is a number from 1 to 2,000 in one aspect, and from 50 to 500 in another aspect of the invention; $R^{21}$ is a monovalent radical conforming to the general formula $C_qH_{2q}L$, wherein q is an integer having a value from 2 to 8 and L is selected from the following groups:

a) —$N(R^{22})CH_2CH_2N(R^{22})_2$
b) —$N(R^{22})$
c) —$N(R^{22})_3CA^-$
d) —$N(R^{22})CH_2CH_2N(R^{22})_2H_2CA^-$ wherein $R^{22}$ is independently selected from hydrogen, $C_1$-$C_{20}$ alkyl, phenyl, benzyl; and $A^-$ is a halide ion selected from chloride, bromide, fluoride, and iodide.

An exemplary cationic silicone corresponding to the previous formula defined immediately above is the polymer known as "trimethylsilylamodimethicone" of formula: $(CH_3)_3$—Si—$[O$—$Si(CH_3)_2)]_g$—$[O$—$(CH_3)Si((CH_2)_3$—NH—$(CH_2)_2$—$NH_2)]_h$—O—$Si(CH_3)_3$ Another cationic silicone useful in combination with the polygalactomannan substituted compositions as variously described above can be represented by the formula:

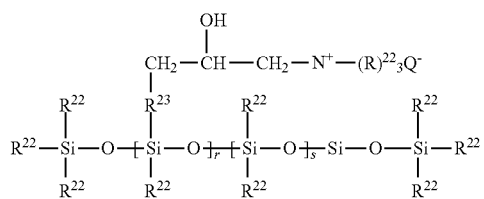

wherein where $R^{22}$ represents a radical selected from a $C_1$-$C_{18}$ alkyl and $C_1$-$C_{18}$ alkenyl radical; $R^{23}$ independently represents a radical selected from a $C_1$-$C_{18}$ alkylene radical or a $C_1$-$C_{18}$ alkyleneoxy radical; Q is a halide ion; r denotes an average statistical value from 2 to 20 in one aspect, and from 2 to 8 in another aspect; s denotes an average statistical value from 20 to 200 in one aspect, and from 20 to 50 in another aspect. In one aspect, $R^{22}$ is methyl. In another aspect, Q is chloride.

Other optional silicone fluids are the insoluble silicone gums. These gums are polysiloxane materials having a viscosity at 25° C. of greater than or equal to 1,000,000 centistokes. Silicone gums are described in U.S. Pat. No. 4,152,416; Noll and Walter, Chemistry and Technology of Silicones, New York: Academic Press 1968; and in General Electric Silicone Rubber Product Data Sheets SE 30, SE 33, SE 54 and SE 76, all of which are incorporated herein by reference. The silicone gums will typically have a mass molecule weight in excess of about 200,000 Daltons, generally between about 200,000 to about 1,000,000 Daltons, specific examples of which include polydimethylsiloxane, polydimethylsiloxane/methylvinylsiloxane copolymer, polydimethylsiloxane/diphenyl siloxane/methylvinylsiloxane) copolymer, and mixtures thereof.

Another category of nonvolatile, insoluble silicone fluid conditioning agents are the high refractive index polysiloxanes, having a refractive index of at least about 1.46 in one aspect, at least about 1.48 in another aspect, at least about 1.52 in a further aspect, and at least about 1.55 in a still further aspect. The refractive index of the polysiloxane fluid will generally be less than about 1.70, typically less than about 1.60. In this context, polysiloxane "fluid" includes oils as well as gums.

The high refractive index polysiloxane fluid includes those represented by the general formula set forth for the polyalkyl, polyaryl, and polyalkylaryl siloxanes described above, as well as cyclic polysiloxanes (cyclomethicones) represented by the formula:

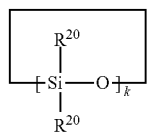

wherein the substituent $R^{20}$ is as defined above, and the number of repeat units, k, ranges from about 3 to about 7 in one aspect, and from 3 to 5 in another aspect. The high refractive index polysiloxane fluids can contain an amount of aryl containing $R^{20}$ substituents sufficient to increase the refractive index to the desired level, which is described above. Additionally, $R^{20}$ and k must be selected so that the material is non-volatile. Aryl containing substituents include those which contain alicyclic and heterocyclic five and six member aryl rings and those which contain fused five or six member rings. The aryl rings can be substituted or unsubstituted. Substituents include aliphatic substituents, and can also include alkoxy substituents, acyl substituents, ketones, halogens (e.g., Cl and Br), amines, etc. Exemplary aryl containing groups include substituted and unsubstituted arenes, such as phenyl, and phenyl derivatives such as phenyls with $C_1$-$C_5$ alkyl or alkenyl substituents, e.g., allylphenyl, methyl phenyl and ethyl phenyl, vinyl phenyls such as styrenyl, and phenyl alkynes (e.g. phenyl $C_2$-$C_4$ alkynes). Heterocyclic aryl groups include substituents derived from furan, imidazole, pyrrole, pyridine, etc. Fused aryl ring substituents include, for example, naphthalene, coumarin, and purine.

The high refractive index polysiloxane fluids will have a degree of aryl containing substituents of at least about 15% by wt. in one aspect, at least about 20% by wt. in another aspect, at least about 25% by wt. in a further aspect, at least about 35% by wt. in still further aspect, and at least about 50% by wt. in an additional aspect, based on the wt. of the polysiloxane fluid. Typically, the degree of aryl substitution will be less than about 90% by wt., more typically less than about 85% by wt., and can generally ranges from about 55% to about 80% by wt. of the polysiloxane fluid.

In another aspect, the high refractive index polysiloxane fluids have a combination of phenyl or substituted phenyl derivatives. The substituents can be selected from $C_1$-$C_4$ alkyl (e.g., methyl), hydroxy, and $C_1$-$C_4$ alkylamino (e.g., —$R^{24}NHR^{25}NH_2$ wherein each $R^{24}$ and $R^{25}$ group independently is a $C_1$-$C_3$ alkyl, alkenyl, and/or alkoxy.

When high refractive index silicones are used in the compositions of the present invention, they optionally can be used in solution with a spreading agent, such as a silicone resin or a surfactant, to reduce the surface tension by a sufficient amount to enhance spreading and thereby enhance the glossiness (subsequent to drying) of hair treated with such compositions. Silicone fluids suitable for use are disclosed in U.S. Pat. No. 2,826,551, U.S. Pat. No. 3,964,500, U.S. Pat. No. 4,364,837, British Pat. No. 849,433, and Silicon Compounds, Petrarch Systems, Inc. (1984), all of which are incorporated herein by reference. High refractive index polysiloxanes are available from Dow Corning Corporation (Midland, Mich.) Huls America (Piscataway, N.J.), and General Electric Silicones (Waterford, N.Y.).

Silicone resins can be included in the silicone conditioning agent suitable for use in combination with the polygalactomannan substituted compositions as variously described above. These resins are crosslinked polysiloxanes. The crosslinking is introduced through the incorporation of trifunctional and tetrafunctional silanes with monofunctional or difunctional (or both) silanes during manufacture of the silicone resin.

As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. In one aspect, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and terachlorosilane, with the methyl-substituted silanes being most commonly utilized. Silicone resins are offered by General Electric as GE SS4230 and SS4267.

Silicone materials and silicone resins in particular, are identified according to a shorthand nomenclature system known to those of ordinary skill in the art as "MDTQ" nomenclature. Under this system, the silicone is described according to the presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetra-functional unit $SiO_2$. Primes of the unit symbols (e.g. M', D', T', and Q') denote substituents other than methyl, and must be specifically defined for each occurrence. Typical alternate substituents include groups such as vinyl, phenyls, amines, hydroxyls, etc. The molar ratios of the various units, either in terms of subscripts to the symbol indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

Exemplary silicone resins include, but are not limited to MQ, MT, MTQ, MDT and MDTQ resins. In one aspect, methyl is the silicone resin substituent. In another aspect, the silicone resin is selected from a MQ resins, wherein the M:Q ratio is from about 0.5:1.0 to about 1.5:1.0 and the average molecular weight of the silicone resin is from about 1000 to about 10,000 Daltons.

When employed with non-volatile silicone fluids having a refractive index below 1.46, the weight ratio of the non-volatile silicone fluid to the silicone resin component, ranges from about 4:1 to about 400:1 in one aspect, from about 9:1 to about 200:1 in another aspect, from about 19:1 to about 100:1 in a further aspect, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e., the conditioning active, the sum of the fluid and resin should be included in determining the level of silicone conditioning agent in the composition.

The volatile silicones described above include cyclic and linear polydimethylsiloxanes, and the like. Cyclic volatile silicones (cyclomethicones) typically contain about 3 to about 7 silicon atoms, alternating with oxygen atoms, in a cyclic ring structure such as described above for the non-volatile cyclic silicones. However, each $R^{20}$ substituent and repeating unit, k, in the formula must be selected so that the material is non-volatile. Typically, $R^{20}$ is substituted with two alkyl groups (e.g., methyl groups). The linear volatile silicones are silicone fluids, as described above, having viscosities of not more than about 25 mPa·s. "Volatile" means that the silicone has a measurable vapor pressure, or a vapor pressure of at least 2 mm of Hg at 20° C. Non-volatile silicones have a vapor pressure of less than 2 mm Hg at 20° C. A description of cyclic and linear volatile silicones is found in Todd and Byers, "Volatile Silicone Fluids for Cosmetics", Cosmetics and Toiletries, Vol. 91(1), pp. 27-32 (1976), and in Kasprzak, "Volatile Silicones", Soap/Cosmetics/Chemical Specialties, pp. 40-43 (December 1986), each incorporated herein by reference.

Exemplary volatile cyclomethicones are D4 cyclomethicone (octamethylcyclotetrasiloxane), D5 cyclomethicone (decamethylcyclopentasiloxane), D6 cyclomethicone, and blends thereof (e.g., D4/D5 and D5/D6). Volatile cyclomethicones and cyclomethicone blends are commercially available from G.E. Silicones as SF1173, SF1202, SF1256, and SF1258, Dow Corning Corporation as Dow Corning® 244, 245, 246, 345, 1401 and 1501 Fluids. Blends of volatile cyclomethicones and volatile linear dimethicones are also contemplated.

Exemplary volatile linear dimethicones include hexamethyldisiloxane, octamethyltrisiloxane, decamethyltetrasiloxane, dodecamethylpentasiloxane and blends thereof. Volatile linear dimethicones and dimethicone blends are commercially available from Dow Corning Corporation as Dow Corning 200® Fluid (e.g., product designations 0.65 CST, 1 CST, 1.5 CST, and 2 CST) and Dow Corning® 2-1184 Fluid.

Emulsified silicones are also suitable for combination with the polygalactomannan substituted compositions as variously described above. Typically, silicone emulsions have an average silicone particle size in the composition of less than 30 μm in one aspect, less than 20 μm in another aspect, and less than 10 μm in a further aspect. In one embodiment of the invention, the average silicone particle size of the emulsified silicone in the composition is less than 2 μm, and ideally it ranges from 0.01 to 1 μm. Silicone emulsions having an average silicone particle size of <0.15 micrometers are generally termed micro-emulsions. Particle size may be measured by means of a laser light scattering technique, using a 2600D Particle Sizer from Malvern Instruments. Suitable silicone emulsions for use in the invention are also commercially available in a pre-emulsified form. Examples of suitable pre-formed emulsions include emulsions DC2-1766, DC2-1784, DC2-1788, and micro-emulsions DC2-1865 and DC2-1870, all available from Dow Corning. These are all emulsions/micro-emulsions of dimethiconol. Crosslinked silicone gums are also available in a pre-emulsified form, which is advantageous for ease of formulation. An exemplary material is available from Dow Corning as DC X2-1787, which is an emulsion of crosslinked dimethiconol gum. Another exemplary material is available from Dow Corning as DC X2-1391, which is a micro-emulsion of crosslinked dimethiconol gum. Preformed emulsions of amino functional silicone are also available from suppliers of silicone oils such as Dow Corning and General Electric. Particularly suitable are emulsions of amino functional silicone oils with non ionic and/or cationic surfactant. Specific examples include DC929 Cationic Emulsion, DC939 Cationic Emulsion, DC949 Cationic emulsion, and the non-ionic emulsions DC2-7224, DC2-8467, DC2-8177 and DC2-8154 (all available from Dow Corning). Mixtures of any of the above types of silicone may also be used. Specific examples of amino functional silicones suitable are the aminosilicone oils DC2-8220, DC2-8166, DC2-8466, and DC2-8950-114 (all available from Dow Corning), and GE 1149-75, (ex General Electric Silicones). An example of a quaternary silicone polymer useful in the present invention is the material K3474, available from Goldschmidt, Germany.

Other suitable silicone oils include the dimethicone copolyols, which are linear or branched copolymers of dimethylsiloxane (dimethicone) modified with alkylene oxide units. The alkylene oxide units can be arranged as random or block copolymers. A generally useful class of dimethicone polyols are block copolymers having terminal and/or pendent blocks of polydimethylsiloxane and blocks of polyalkylene oxide, such as blocks of polyethylene oxide, polypropylene oxide, or both. Dimethicone copolyols can be water soluble or insoluble depending on the amount of polyalkylene oxide present in the dimethicone polymer and can be anionic, cationic, or nonionic in character.

The water soluble or water dispersible silicones can also be used in combination with the polygalactomannan substituted compositions as variously described above. Such water soluble silicones contain suitable anionic functionality, cationic functionality, and/or nonionic functionality to render the silicone water soluble or water dispersible. In one embodiment, the water soluble silicones contain a polysiloxane main chain to which is grafted at least one anionic moiety. The anionic moiety can be grafted to a terminal end of the polysiloxane backbone, or be grafted as a pendant side group, or both. By anionic group is meant any hydrocarbon moiety that contains at least one anionic group or at least one group that can be ionized to an anionic group following neutralization by a base. As discussed previously, the quantity of the hydrocarbon groups of anionic character which are grafted onto the silicone chain are chosen so that the corresponding silicone derivative is water-soluble or water-dispersible after neutralization of the ionizable groups with a base. The anionic silicone derivatives can be selected from existing commercial products or can be synthesized by any means known in the art. The nonionic silicones contain alkylene oxide terminal and/or pendant side chain units (e.g., dimethicone copolyols).

Silicones with anionic groups can be synthesized by reaction between (i) a polysiloxane containing a silinic hydrogen and (ii) a compound containing olefinic unsaturation that also contains an anionic functional group. Exemplary of such a reaction is the hydrosilylation reaction between poly(dimethylsiloxanes) containing a Si—H group(s) and an olefin, $CH_2=CHR^{26}$, wherein $R^{26}$ represents a moiety containing an anionic group. The olefin can be monomeric, oligomeric or polymeric. Polysiloxane compounds that contain a pendant reactive thio (—SH) group(s) are also suitable for grafting an unsaturated anionic group containing compound to the poly(siloxane) backbone.

According to one aspect of the present invention, the anionic monomers containing ethylenic unsaturation are used alone or in combination and are selected from linear or branched, unsaturated carboxylic acids. Exemplary unsaturated carboxylic acids are acrylic acid, methacrylic acid, maleic acid, maleic anhydride, itaconic acid, fumaric acid and crotonic acid. The monomers can optionally be partially or completely neutralized by base to form an alkali, alkaline earth metal, and ammonium salt. Suitable bases include but are not limited to the alkali, alkaline earth (e.g., sodium, potassium, lithium, calcium) and ammonium hydroxides. It will be noted that, similarly, the oligomeric and polymeric graft segments formed from the forgoing monomers can be post-neutralized with a base (sodium hydroxide, aqueous ammonia, etc.) to form a salt. Examples of silicone derivatives which are suitable for use are described in patent applications numbers EP-A-0 582,152 and WO 93/23009. An exemplary class of silicone polymers are the polysiloxanes containing repeat units represented by the following structure:

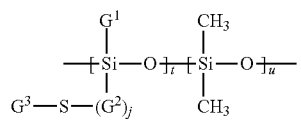

wherein $G^1$ represents hydrogen, $C_1$-$C_{10}$ alkyl and phenyl radical; $G^2$ represents $C_1$-$C_{10}$ alkylene; $G^3$ represents an anionic polymeric residue obtained from the polymerization of at least one anionic monomer containing ethylenic unsaturation; j is 0 or 1; t is an integer ranging from 1 to 50; and u is an integer from 10 to 350. In one embodiment of the invention, $G^1$ is methyl; j is 1; and $G_2$ is propylene radical; $G^3$ represents a polymeric radical obtained from the polymerization of at least one unsaturated monomer containing a carboxylic acid group (e.g., acrylic acid, methacrylic acid, itaconic acid, fumaric acid, crotonic acid, maleic acid, or aconitic acid, and the like).

The carboxylate group content in the final polymer preferably ranges from 1 mole of carboxylate per 200 g of polymer to 1 mole of carboxylate per 5000 g of polymer. The number molecular mass of the silicone polymer preferably ranges from 10,000 to 1,000,000 and still more preferably from 10,000 to 100,000. Exemplary unsaturated monomers containing carboxylic acid groups are acrylic acid and methacrylic acid. In addition, to the carboxylic acid group containing monomers, $C_1$-$C_{20}$ alkyl esters of acrylic acid and methacrylic acid can be copolymerized into the polymeric backbone. Exemplary esters include but are not limited to the ethyl and butyl esters of acrylic and methacrylic acid. A commercially available silicone-acrylate polymer is marketed by the 3M Company under the trademark Silicones "Plus" Polymer 9857C (VS80 Dry). These polymers contain a polydimethylsiloxanes (PDMS) backbone onto which is grafted (through a thiopropylene group) random repeating units of poly(meth)acrylic acid and the butyl ester of poly(meth)acrylate. These products can be obtained conventionally by radical copolymerization between thiopropyl functionalized polydimethylsiloxane and a mixture of monomers comprising (meth)acrylic acid and of butyl(meth) acrylate.

In another embodiment, the water soluble silicone copolyol can be represented silicone copolyol carboxylates represented by the formula:

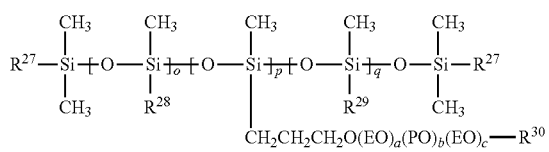

where $R^{27}$ and $R^{28}$ are independently selected from $C_1$-$C_{30}$ alkyl, $C_6$-$C_{14}$ aryl, $C_7$-$C_{15}$ aralkyl, $C_1$-$C_{15}$ alkaryl, or an alkenyl group of 1 to 40 carbons, hydroxyl, —$R^{31}$-G' or —$(CH_2)_3O(EO)_a(PO)_b(EO)_c$-G', with the proviso that both $R^{27}$ and $R^{28}$ are not methyl; $R^{29}$ is selected from $C_1$-$C_5$ alkyl or phenyl; in this formula a, b, and c are integers independently ranging from 0 to 100; EO is ethylene oxide, —$(CH_2CH_2O)$—; PO is propylene oxide, —$(CH_2CH(CH_3)O)$—; in this formula o is an integer ranging from 1 to 200, p is an integer ranging from 0 to 200, and q is an integer ranging from 0 to 1000; $R^{30}$ is hydrogen, $C_1$-$C_{30}$ alkyl, aryl, $C_7$-$C_{15}$ aralkyl, $C_7$-$C_{15}$ alkaryl, or alkenyl group of 1 to 40 carbons or —C(O)—X wherein X is $C_1$-$C_{30}$ alkyl, $C_6$-$C_{14}$ aryl, $C_7$-$C_{15}$ aralkyl, $C_1$-$C_{15}$alkaryl, or an alkenyl group of 1 to 40 carbons, or a mixture thereof; $R^{31}$ is a divalent group selected from alkylene radical of 1 to 40 carbon atoms which may be interrupted with arylene group of 6 to 18 carbons or an alkylene group containing unsaturation of 2 to 8 carbons; and G' is independently are selected from:

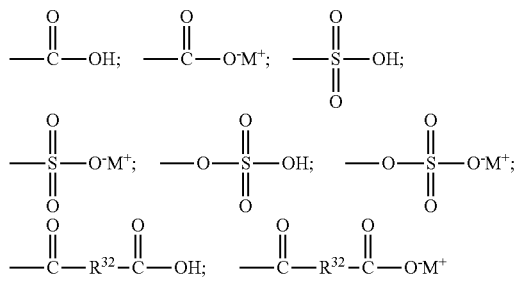

where $R^{32}$ is a divalent group selected from alkylene of 1 to 40 carbons, an unsaturated group containing 2 to 5 carbon atoms, or an arylene group of 6 to 12 carbon atoms; where M is a cation selected from Na, K, Li, $NH_4$, or an amine containing $C_1$-$C_{10}$ alkyl, $C_6$-$C_{14}$ aryl (e.g., phenyl, naphthyl), $C_2$-$C_{10}$ alkenyl, $C_1$-$C_{10}$ hydroxyalkyl, $C_7$-$C_{24}$ arylalkyl or $C_7$-$C_{24}$ alkaryl groups. Representative $R^{32}$ radicals are: —$CH_2CH_2$—, —CH═CH—, —CH═$CHCH_2$—, and phenylene.

In another embodiment, the water soluble silicones useful in the practice of the present invention can be represented an anionic silicone copolyol represented by the formula:

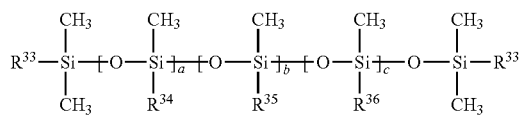

where is $R^{33}$ is methyl or hydroxyl; $R^{34}$ is selected from $C_1$-$C_8$ alkyl or phenyl; $R^{35}$ represents the radical —$(CH_2)_3O(EO)_x(PO)_y(EO)_z$—$SO_3^-M^+$; where M is a cation selected from Na, K, Li, or $NH_4$; in this formula x, y and z are integers independently ranging from 0 to 100; $R^{36}$ represents the radical —$(CH_2)_3O(EO)_x(PO)_y(EO)_z$—H; in this formula a and c are independently integers ranging from 0 to 50, and b is an integer ranging from 1 to 50; EO is ethylene oxide, e.g., $(CH_2CH_2O)$—; PO is propylene oxide, e.g., —$(CH_2CH(CH_3)O)$—.

In still another embodiment, the water soluble silicones useful in the practice of the present invention can be represented an anionic silicone copolyol represented by the formula:

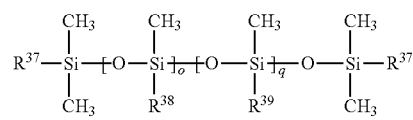

wherein $R^{37}$ and $R^{38}$ independently are —$CH_3$ or a radical represented by: —$(CH_2)_3O(EO)_a(PO)_b(EO)_c$—C(O)—$R^{40}$—C(O)OH, subject to the proviso that both $R^{37}$ and $R^{38}$ are not —$CH_3$ at the same time; $R^{40}$ is selected from the divalent radical —$CH_2CH_2$—, —CH═CH—, and phenylene; $R^{39}$ is selected from $C_1$-$C_5$ alkyl or phenyl; in this formula a, b and c are integers independently ranging from 0 to 20; EO is an ethylene oxide residue, e.g., —$(CH_2CH_2O)$—; PO is a propylene oxide residue, e.g., —$(CH_2CH(CH_3)O)$—; in this formula o is an integer ranging from 1 to 200 and q is an integer ranging from 0 to 500.

Other water soluble silicones useful in the invention are quaternized silicone copolyol polymers. These polymers have a pendant quaternary nitrogen functional group present and are represented by the formula:

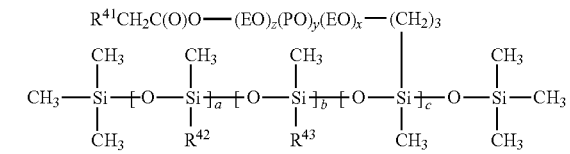

where $R^{41}$ represents a quaternary substituent —$N^+R^3R^4R^5X^-$, wherein $R^3$ and $R^4$, and $R^5$, independently, are selected from hydrogen and linear and branched $C_1$-$C_{24}$ alkyl, and $X^-$ represents an anion suitable to balance the cationic charge on the nitrogen atom; $R^{42}$ is selected from $C_1$-$C_{10}$ alkyl and phenyl; $R^{43}$ is —$(CH_2)_3O(EO)_x(PO)_y(EO)_z$—H, where EO is an ethylene oxide residue, e.g., —$(CH_2CH_2O)$—; PO is a propylene oxide residue, e.g., —$(CH_2CH(CH_3)O)$—; in this formula a is an integer from 0 to 200, b is an integer from 0 to 200, and c is an integer from 1 to 200; in this formula x, y and z are integers and are independently selected from 0 to 20. In one aspect, the anion $X^-$ represents an anion selected from chloride, bromide, iodide, sulfate, methylsulfate, sulfonate, nitrate, phosphate, and acetate.

Other suitable water soluble silicones are amine substituted silicone copolyols represented by the formula:

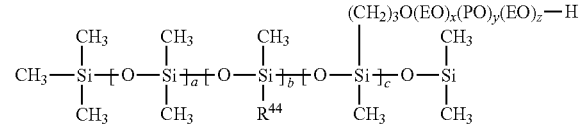

where $R^{44}$ is selected from —$NH(CH_2)_nNH_2$ or —$(CH_2)_nNH_2$, where in this formula n is an integer from 2 to 6; and x, is n integer from 0 to 20; where EO is an ethylene oxide residue, e.g., —(CH$_2$CH$_2$O)—; PO is a propylene oxide residue, e.g., —(CH$_2$CH(CH$_3$)O)—; in this formula a is an integer from 0 to 200, b is an integer from 0 to 200, and c is an integer from 1 to 200; in this formula x, y and z are integers and are independently selected from 0 to 20.

Still other water soluble silicones can be selected from nonionic silicone copolyols (dimethicone copolyols) represented by the formula:

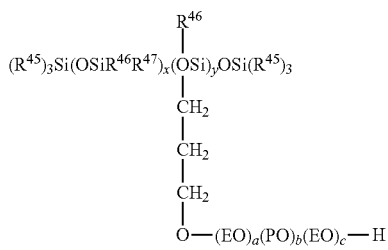

where $R^{45}$, independently, represents a radical selected from C$_1$-C$_{30}$ alkyl, C$_6$-C$_{14}$ aryl, and C$_2$-C$_{20}$ alkenyl; $R^{46}$ represents a radical selected from C$_1$-C$_{30}$ alkyl, C$_6$-C$_{14}$ aryl, and C$_2$-C$_{20}$ alkenyl; EO is an ethylene oxide residue, e.g., —(CH$_2$CH$_2$O)—; PO is a propylene oxide residue, e.g., —(CH$_2$CH(CH$_3$)O)—; in this formula a, b, and c are, independently, 0 to 100; in this formula x is 0 to 200; and y is 1 to 200.

In another embodiment, water soluble silicones can be selected from nonionic silicone copolyols represented by the formula:

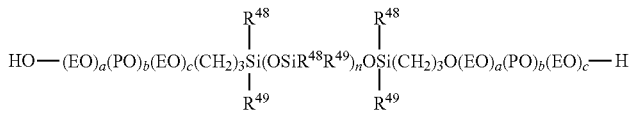

wherein $R^{48}$ and $R^{49}$, independently, represent a radical selected from C$_1$-C$_{30}$ alkyl, C$_6$-C$_{14}$ aryl, and C$_2$-C$_{20}$ alkenyl; EO is an ethylene oxide residue, e.g., —(CH$_2$CH$_2$O)—; PO is a propylene oxide residue, e.g., —(CH$_2$CH(CH$_3$)O)—; in this formula a, b, and c are independently 0 to 100; and in this formula n is 0 to 200.

In the copolyol embodiments set forth above, the EO and PO residues can be arranged in random, non-random, or blocky sequences.

Dimethicone copolyols are disclosed in U.S. Pat. Nos. 5,136,063 and 5,180,843, the disclosures of which are incorporated herein by reference. In addition, dimethicone copolyols are commercially available under the Silsoft® and Silwet® brand names from the General Electric Company (GE-OSi). Specific product designations include but are not limited to Silsoft 305, 430, 475, 810, 895, Silwet L 7604 (GE-OSi); Dow Corning® 5103 and 5329 from Dow Corning Corporation; and Abil® dimethicone copolyols, such as, for example WE 09, WS 08, EM 90 and EM 97 from Evonik Goldschmidt Corporation; and Silsense™ dimethicone copolyols, such as Silsense Copolyol-1 and Silsense Copolyol-7, available from Lubrizol Advanced Materials, Inc.

The conditioning component of the conditioner and shampoo compositions of the present invention can also comprise from about 0.05% to about 3%, by weight of the composition in one aspect, from about 0.08% to about 1.5% in another aspect, and from about 0.1% to about 1% in a further aspect, of at least one conditioning oil as the conditioning agent, either alone or in combination with other conditioning agents, such as the silicones (described above) and the other conditioning agents described below.

Suitable conditioning oils include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils typically contain about 12 to 19 carbon atoms. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2,2,4,4,6,6,8,8-dimethyl-10-methylundecane and 2,2,4,4,6,6-dimethyl-8-methylnonane, available from Permethyl Corporation. Hydrocarbon polymers such as polybutene and polydecene. A preferred hydrocarbon polymer is polybutene, such as the copolymer of isobutylene and butene. A commercially available material of this type is L-14 polybutene from BP Chemical Company.

Natural oil conditioners are also useful in accordance with an embodiment of this invention and include but are not limited to peanut, sesame, avocado, coconut, cocoa butter, almond, safflower, corn, cotton seed, sesame seed, walnut oil, castor, olive, jojoba, palm, palm kernel, argan, cedar, soybean, wheat germ, linseed, sunflower seed; *eucalyptus*, lavender, vetiver, *litsea, cubeba*, lemon, sandalwood, rosemary, chamomile, savory, nutmeg, cinnamon, hyssop, caraway, orange, geranium, cade, and bergamot oils, fish oils, glycerol tricaprocaprylate; and mixtures thereof. The natural oils can also be utilized as emollients.

Natural and synthetic wax conditioning agents can be employed in the compositions of the invention, including but are not limited to carnauba wax, candelila wax, alfa wax, paraffin wax, ozokerite wax, olive wax, rice wax, hydrogenated jojoba wax, flower wax, fruit wax (i.e. apple peel wax or orange peel wax), bees wax, modified bees wax, e.g., cerabellina wax, marine waxes, polyolefin waxes, e.g., polyethylene wax; and mixtures thereof.

Liquid polyolefin conditioning oils can be used in the compositions of the present invention. The liquid polyolefin conditioning agents are typically poly-α-olefins that have been hydrogenated. Polyolefins for use herein can be prepared by the polymerization of C$_4$ to about C$_{14}$ olefinic monomers. Non-limiting examples of olefinic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. In one aspect of the invention, hydrogenated α-olefin monomers include, but are not limited to: 1-hexene to 1-hexadecenes, 1-octene to 1-tetradecene, and mixtures thereof.

Fluorinated or perfluorinated oils are also contemplated for use in accordance with an embodiment of the present invention. Fluorinated oils include perfluoropolyethers described in European Patent 0 486 135 and the fluorohydrocarbon compounds described in WO 93/11103. The fluoridated oils may also be fluorocarbons such as fluoramines, e.g., perfluorotributylamine, fluoridated hydrocarbons, such as perfluorodecahydronaphthalene, fluoroesters, and fluoroethers.

Other suitable organic conditioners for use as the conditioning agent in the compositions of the present invention include, but are not limited to, fatty esters having at least 10 carbon atoms. These fatty esters include esters derived from fatty acids or alcohols (e.g., mono-esters, polyhydric alcohol esters, and di- and tri-carboxylic acid esters). The fatty esters hereof may include or have covalently bonded thereto other compatible functionalities, such as amides and alkoxy moieties (e.g., ethoxy or ether linkages, etc.).

Exemplary fatty esters include, but are not limited to isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the compositions of the present invention are mono-carboxylic acid esters of the general formula $R^{50}C(O)OR^{51}$, wherein $R^{50}$ and $R^{51}$ are alkyl or alkenyl radicals, and the sum of carbon atoms in $R^{50}$ and $R^{51}$ is at least 10 in one aspect, and at least 22 in another embodiment of the invention.

Still other fatty esters suitable for use in the compositions of the present invention are di- and tri-alkyl and alkenyl esters of carboxylic acids, such as esters of $C_4$-$C_8$ dicarboxylic acids (e.g., $C_1$-$C_{22}$ esters, preferably $C_{1-C6}$, of succinic acid, glutaric acid, adipic acid). Specific non-limiting examples of di- and tri-alkyl and alkenyl esters of carboxylic acids include isocetyl stearoyl stearate, diisopropyl adipate, and tristearyl citrate.

Other fatty esters suitable for use in the compositions of the present invention are those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Specific non-limiting examples of suitable synthetic fatty esters for use in the personal cleansing compositions of the present invention include: P-43 ($C_8$-$C_{10}$ triester of trimethylolpropane), MCP-684 (tetraester of 3,3 diethanol-1,5 pentadiol), MCP 121 ($C_8$-$C_{10}$ diester of adipic acid), all of which are available from ExxonMobil Chemical Company.

Other oily material conditioning agents that are useful in combination with the polygalactomannan substituted compositions as variously described above include, for example, acetylated lanolin alcohols; lanolin alcohol concentrates; esters of lanolin fatty acids such as the isopropyl esters of lanolin fatty acid; polyol fatty acids; ethoxylated alcohols, such as ethoxylate and castor oils; sterols; sterol esters; sterol ethoxylates; and like materials.

Cationic polymers are also useful as conditioning agents alone or in combination with the other conditioning agents described herein. Suitable cationic polymers can be synthetically derived or modified natural polymers such as the cationically modified polysaccharides. While several of the cationic polymers listed herein as suitable conditioning agents are duplicative of those described above for uses in other applications, those of skill in the art will recognize that many polymers serve multiple functions.

Representative cationic polymer conditioners include but are not limited to homopolymers and copolymers derived from free radically polymerizable acrylic or methacrylic ester or amide monomers. The copolymers can contain one or more units derived from acrylamides, methacrylamides, diacetone acrylamides, acrylic or methacrylic acids or their esters, vinyllactams such as vinyl pyrrolidone or vinyl caprolactam, and vinyl esters. Exemplary polymers include copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone/dialkylaminoalkyl acrylate or methacrylate, optionally quaternized, such as the products sold under the name GAFQUAT™ by International Specialty Products; the dimethyl amino ethyl methacrylate/vinyl caprolactam/vinyl pyrrolidone terpolymers, such as the product sold under the name GAFFIX™ VC 713 by International Specialty Products; the vinyl pyrrolidone/methacrylamidopropyl dimethylamine copolymer, marketed under the name STYLEZE™ CC 10 available from International Specialty Products; and the vinyl pyrrolidone/quaternized dimethyl amino propyl methacrylamide copolymers such as the product sold under the name GAFQUAT™ HS 100 by International Specialty Products.

Cationic conditioner agents can also be selected from the quaternary polymers of vinyl pyrrolidone and vinyl imidazole such as the products sold under the trade name Luviquat® (product designation FC 905, FC 550, and FC 370) by BASF. Other cationic polymer conditioners that can be used in the compositions of the invention include polyalkyleneimines such as polyethyleneimines, polymers containing vinyl pyridine or vinyl pyridinium units, condensates of polyamines and epichlorhydrins, quaternary polysaccharides, quaternary polyurethanes, and quaternary derivatives of chitin.

Other non-limiting examples of quaternary ammonium compounds useful as cationic conditioners in accordance with an embodiment of the present invention include acetamidopropyl trimonium chloride, behenamidopropyl dimethylamine, behenamidopropyl ethyldimonium ethosulfate, behentrimonium chloride, cetethyl morpholinium ethosulfate, cetrimonium chloride, cocoamidopropyl ethyldimonium ethosulfate, dicetyldimonium chloride, dimethicone hydroxypropyl trimonium chloride, hydroxyethyl behenamidopropyl dimonium chloride, quaternium-26, quaternium-27, quaternium-53, quaternium-63, quaternium-70, quaternium-72, quaternium-76 hydrolyzed collagen, PPG-9 diethylmonium chloride, PPG-25 diethylmonium chloride, PPG-40 diethylmonium chloride, stearalkonium chloride, stearamidopropyl ethyl dimonium ethosulfate, steardimonium hydroxypropyl hydrolyzed wheat protein, steardimonium hydroxypropyl hydrolyzed collagen, wheat germamidopropalkonium chloride, wheat germamidopropyl ethyldimonium ethosulfate, polymers and copolymers of dimethyl diallyl ammonium chloride, such as Polyquaternium-4, Polyquaternium-6, Polyquaternium-7, Polyquaternium-10, Polyquaternium-11, Polyquarternium-16, Polyquaternium-22, Polyquaternium-24, Polyquaternium-28, Polyquaternium-29, Polyquaternium-32, Polyquaternium-33, Polyquaternium-35, Polyquaternium-37, Polyquaternium-39, Polyquaternium-44, Polyquaternium-46, Polyquaternium-47, Polyquaternium-52, Polyquaternium-53, Polyquaternium-55, Polyquaternium-59, Polyquaternium-61, Polyquaternium-64, Polyquaternium-65, Polyquaternium-67, Polyquaternium-69, Polyquaternium-70, Polyquaternium-71, Polyquaternium-72, Polyquaternium-73, Polyquaternium-74, Polyquaternium-76, Polyquaternium-77, Polyquaternium-78, Polyquaternium-79, Polyquaternium-80, Polyquaternium-81, Polyquaternium-82, Polyquaternium-84, Polyquaternium-85, Polyquaternium-86, Polyquaternium-87, Polyquaternium-88, Polyquaternium-89, Polyquaternium-91, Polyquaternium-98, PEG-2-cocomonium chloride.

As discussed above, numerous ingredients are known in the art as conditioning agents for hair or skin. In addition to those discussed, other non-limiting examples include PCA (DL-pyrrolidone carboxylic acid) and its salts, such as lysine PCA, aluminum PCA, copper PCA, chitosan PCA, and the like, allantoin; urea; hyaluronic acid and its salts; ceramides; sorbic acid and its salts; sugars and starches and derivatives thereof; lactamide MEA; and the like.

In another embodiment of the invention, the polygalactomannan substituted compositions as variously described above can be formulated in combination with one or more auxiliary rheology modifiers and thickeners. Suitable rheology modifiers and thickeners include synthetic and semi-synthetic rheology modifiers. Exemplary synthetic rheology modifiers include acrylic based polymers and copolymers. One class of acrylic based rheology modifiers are the carboxyl functional alkali-swellable and alkali-soluble thickeners (ASTs) produced by the free-radical polymerization of acrylic acid alone or in combination with other ethylenically unsaturated monomers. The polymers can be synthesized by solvent/precipitation as well as emulsion polymerization techniques. Exemplary synthetic rheology modifiers of this class include homopolymers of acrylic acid or methacrylic acid and copolymers polymerized from one or more monomers of acrylic acid, substituted acrylic acid, and salts and $C_1$-$C_{30}$ alkyl esters of acrylic acid and substituted acrylic acid. As defined herein, the substituted acrylic acid contains a substituent positioned on the alpha and/or beta carbon atom of the molecule wherein the substituent is preferably and independently selected from $C_{1-4}$ alkyl, —CN, and —COOH. Optionally, other ethylenically unsaturated monomers such as, for example, styrene, vinyl acetate, ethylene, butadiene, acrylonitrile, as well as mixtures thereof can be copolymerized into the backbone. The foregoing polymers are optionally crosslinked by a monomer that contains two or more moieties that contain ethylenic unsaturation. In one aspect, the crosslinker is selected from a polyalkenyl polyether of a polyhydric alcohol containing at least two alkenyl ether groups per molecule. Other Exemplary crosslinkers are selected from allyl ethers of sucrose and allyl ethers of pentaerythritol, and mixtures thereof. These polymers are more fully described in U.S. Pat. No. 5,087,445; U.S. Pat. No. 4,509,949; and U.S. Pat. No. 2,798,053 herein incorporated by reference.

In one embodiment, the AST rheology modifier or thickener is a crosslinked homopolymer polymerized from acrylic acid or methacrylic acid and is generally referred to under the INCI name of Carbomer. Commercially available Carbomers include Carbopol® polymers 934, 940, 941, 956, 980 and 996 available from Lubrizol Advanced Materials, Inc. In another embodiment the AST rheology modifier is selected from a crosslinked copolymer polymerized from a first monomer selected from one or more monomers of (meth)acrylic acid, substituted acrylic acid, and salts of (meth)acrylic acid and substituted acrylic acid and a second monomer selected from one or more $C_1$-$C_5$ alkyl acrylate esters of (meth)acrylic acid. These polymers are designated under the INCI name of Acrylates Copolymer. Acrylates Copolymers are commercially available under the trade names Aculyn® 33 from Rohm and Haas and Carbopol® Aqua SF-1 from Lubrizol Advanced Materials, Inc. In a further aspect the rheology modifier is selected from a crosslinked copolymer polymerized from a first monomer selected from one or more monomers of acrylic acid, substituted acrylic acid, salts of acrylic acid and salts of substituted acrylic acid and a second monomer selected from one or more $C_{10}$-$C_{30}$ alkyl acrylate esters of acrylic acid or methacrylic acid. In one aspect, the monomers can be polymerized in the presence of a steric stabilizer such as disclosed in U.S. Pat. No. 5,288,814 which is herein incorporated by reference. Some of the forgoing polymers are designated under INCI nomenclature as Acrylates/C10-30 Alkyl Acrylate Crosspolymer and are commercially available under the trade names Carbopol® 1342 and 1382, Carbopol® Ultrez 20 and 21, Carbopol® ETD 2020 and Pemulen® TR-1 and TR-2 from Lubrizol Advanced Materials, Inc. Any vinyl or acrylic based rheology modifiers are suitable.

Another class of synthetic rheology modifiers and thickeners suitable for use in accordance with an embodiment of the present invention includes hydrophobically modified ASTs commonly referred to as hydrophobically modified alkali-swellable and alkali-soluble emulsion (HASE) polymers. Typical HASE polymers are free radical addition polymers polymerized from pH sensitive or hydrophilic monomers (e.g., acrylic acid and/or methacrylic acid), hydrophobic monomers (e.g., $C_1$-$C_{30}$ alkyl esters of acrylic acid and/or methacrylic acid, acrylonitrile, styrene), an "associative monomer", and an optional crosslinking monomer. The associative monomer comprises an ethylenically unsaturated polymerizable end group, a non-ionic hydrophilic midsection that is terminated by a hydrophobic end group. The non-ionic hydrophilic midsection comprises a polyoxyalkylene group, e.g., polyethylene oxide, polypropylene oxide, or mixtures of polyethylene oxide/polypropylene oxide segments. The terminal hydrophobic end group is typically a $C_8$-$C_{40}$ aliphatic moiety. Exemplary aliphatic moieties are selected from linear and branched alkyl substituents, linear and branched alkenyl substituents, carbocyclic substituents, aryl substituents, aralkyl substituents, arylalkyl substituents, and alkylaryl substituents. In one aspect, associative monomers can be prepared by the condensation (e.g., esterification or etherification) of a polyethoxylated and/or polypropoxylated aliphatic alcohol (typically containing a branched or unbranched $C_8$-$C_{40}$ aliphatic moiety) with an ethylenically unsaturated monomer containing a carboxylic acid group (e.g., acrylic acid, methacrylic acid), an unsaturated cyclic anhydride monomer (e.g., maleic anhydride, itaconic anhydride, citraconic anhydride), a monoethylenically unsaturated monoisocyanate (e.g., α,α-dimethyl-m-isopropenyl benzyl isocyanate) or an ethylenically unsaturated monomer containing a hydroxyl group (e.g., vinyl alcohol, allyl alcohol). Polyethoxylated and/or polypropoxylated aliphatic alcohols are ethylene oxide and/or propylene oxide adducts of a monoalcohol containing the $C_8$-$C_{40}$ aliphatic moiety. Non-limiting examples of alcohols containing a $C_8$-$C_{40}$ aliphatic moiety are capryl alcohol, iso-octyl alcohol (2-ethyl hexanol), pelargonic alcohol (1-nonanol), decyl alcohol, lauryl alcohol, myristyl alcohol, cetyl alcohol, cetyl alcohol, cetearyl alcohol (mixture of $C_{16}$-$C_{18}$ monoalcohols), stearyl alcohol, isostearyl alcohol, elaidyl alcohol, oleyl alcohol, arachidyl alcohol, behenyl alcohol, lignoceryl alcohol, ceryl alcohol, montanyl alcohol, melissyl, lacceryl alcohol, geddyl alcohol, and $C_2$-$C_{20}$ alkyl substituted phenols (e.g., nonyl phenol), and the like.

Exemplary HASE polymers are disclosed in U.S. Pat. Nos. 3,657,175; 4,384,096; 4,464,524; 4,801,671; and 5,292,843, which are herein incorporated by reference. In addition, an extensive review of HASE polymers is found in Gregory D. Shay, Chapter 25, "Alkali-Swellable and Alkali-Soluble Thickener Technology A Review", Polymers in Aqueous Media-Performance Through Association, Advances in Chemistry Series 223, J. Edward Glass (ed.), ACS, pp. 457-494, Division Polymeric Materials, Washington, D.C. (1989), the relevant disclosures of which are incorporated herein by reference. The HASE polymers are commercially available from Rohm & Haas under the trade designations Aculyn® 22 (INCI Name: Acrylates/Steareth-20 Methacrylate Copolymer), Aculyn® 44 (INCI Name: PEG-150/Decyl Alcohol/SMDI Copolymer), Aculyn 46® (INCI Name: PEG-150/Stearyl Alcohol/SMDI Copolymer), and Aculyn® 88 (INCI Name: Acrylates/Steareth-20 Methacrylate Crosspolymer).

Another class of synthetic and semi-synthetic rheology modifiers and thickeners suitable for use in accordance with an embodiment of the present invention includes cationically modified acrylic polymers and copolymers and cationically modified cellulose ethers. The acrylic polymers and copolymers and cellulose ethers are cationically modified via quaternization. For the acrylic polymers and copolymers, quaternization can occur by polymerizing a quaternized monomer into the acrylic polymer backbone or by post functionalizing the acrylic polymer with a quaternizing agent. An exemplary quaternary acrylic polymer is designated under INCI nomenclature as Polyquaternium-37 and is commercially available under the trade names Synthalen CR21 and Synthalen CN, from 3V Inc. The quaternized celluloses are prepared by post functionalizing the desired cellulosic backbone (e.g., hydroxyethyl cellulose) with a quaternizing agent such as a quaternary ammonium salt (e.g., diallyldimethyl ammonium chloride, trimethyl ammonium chloride substituted epoxide). Exemplary quaternary cellulosic polymers are designated under the INCI names Polyquaternium-4, Polyquaternium-10, and Polyquaternium-67.

In another embodiment, acid swellable associative polymers can be used with the polygalactomannan substituted compositions as variously described above. Such polymers generally have cationic and associative characteristics. These polymers are free radical addition polymers polymerized from a monomer mixture comprising an acid sensitive amino substituted hydrophilic monomer (e.g., dialkylamino alkyl(meth)acrylates or (meth)acrylamides), an associative monomer (defined hereinabove), a lower alkyl(meth)acrylate or other free radically polymerizable comonomers selected from hydroxyalkyl esters of (meth)acrylic acid, vinyl and/or allyl ethers of polyethylene glycol, vinyl and/or allyl ethers of polypropylene glycol, vinyl and/or allyl ethers of polyethylene glycol/polypropylene glycol, polyethylene glycol esters of (meth)acrylic acid, polypropylene glycol esters of (meth)acrylic acid, polyethylene glycol/polypropylene glycol esters of (meth)acrylic acid), and combinations thereof. These polymers can optionally be crosslinked. By acid sensitive is meant that the amino substituent becomes cationic at low pH values, typically ranging from about 0.5 to about 6.5. Exemplary acid swellable associative polymers are commercially available under the trade name Structure® Plus (INCI Name: Acrylates/Aminoacrylates/C10-C30 Alkyl PEG-20 Itaconate) from Akzo Nobel, and Carbopol® Aqua CC (INCI Name: Polyacrylates-1 Crosspolymer) from Lubrizol Advanced Materials, Inc. In one aspect, the acid swellable polymer is a copolymer of one or more $C_1$-$C_5$ alkyl esters of (meth)acrylic acid, $C_1$-$C_4$ dialkylamino $C_1$-$C_6$ alkyl methacrylate, PEG/PPG-30/5 alkyl ether, PEG 20-25 $C_{10}$-$C_{30}$ alkyl ether methacrylate, hydroxy $C_2$-$C_6$ alkyl methacrylate crosslinked with ethylene glycol dimethacrylate. Other useful acid swellable associative polymers are disclosed in U.S. Pat. No. 7,378,479, the disclosure of which is herein incorporated by reference.

Hydrophobically modified alkoxylated methyl glucoside, such as, for example, PEG-120 Methyl Glucose Dioleate, PEG-120 Methyl Glucose Trioleate, and PEG-20 Methyl Glucose Sesquistearate, available from Lubrizol Advanced Materials, Inc., under the trade names, Glucamate® DOE-120, Glucamate™ LT, and Glucamate™ SSE-20, respectively, are also suitable rheology modifiers.

Polysaccharides obtained from tree and shrub exudates, such as gum Arabic, gum gahatti, and gum tragacanth, as well as pectin; seaweed extracts, such as alginates and carrageenans; algae extracts, such as agar; microbial polysaccharides, such as xanthan, gellan, and wellan; cellulose ethers, such as ethylhexylethylcellulose, hydroxybutylmethylcellulose, hydroxyethylmethylcellulose, hydroxypropylmethylcellulose, methylcellulose, carboxymethylcellulose, hydroxyethylcellulose, and hydroxypropylcellulose; polygalactomannans, such as fenugreek gum, *cassia* gum, locust bean gum, tara gum, and guar gum; starches, such as corn starch, tapioca starch, rice starch, wheat starch, potato starch and sorghum starch can also be employed in the compositions herein as suitable thickeners and rheology modifiers.

Other rheology modifiers suitable for use in the personal care compositions of the invention are disclosed in U.S. Pat. No. 7,205,271 the disclosure of which is herein incorporated by reference.

The rheology modifiers set forth above, when employed, can be used alone or in combination and typically are used in an amount ranging from about 0.05 wt. % to about 5 wt. % in one aspect, from about 0.1 wt. % to about 3 wt. % in another aspect, and from about 0.2 wt. % to about 2 wt. % in further aspect, based on the total weight of the personal care compositions of the present invention.

Where applicable, any known aerosol propellant can be utilized to deliver the personal care, home care, health care and institutional care compositions containing the polygalactomannan substituted compositions as variously described above in combination with one or more of the foregoing active ingredients and/or with the one or more additives and/or adjuvants, conventionally or popularly included in personal care, health care, home care, and institutional care products discussed above. Exemplary propellants include, but are not limited to, lower boiling hydrocarbons such as $C_3$-$C_6$ straight and branched chain hydrocarbons. Exemplary hydrocarbon propellants include propane, butane, isobutene, and mixtures thereof. Other suitable propellants include ethers, such as, dimethyl ether, hydrofluorocarbons, such as, 1,1-difluoroethane and HFO-1234ze (tetrafluoropropylene), and compressed gasses, such as air and carbon dioxide. These compositions can contain from about 0.5 to about 60 wt. % of the propellant in one embodiment and from about 0.5 to about 35 wt. % in another embodiment, based on the total weight of the composition.

While overlapping weight ranges for the various components and ingredients that can be contained in the compositions of the invention have been expressed for selected embodiments and aspects of the invention, it should be readily apparent that the specific amount of each component in the disclosed personal care, home care, health care, and institutional care compositions will be selected from its disclosed range such that the amount of each component is adjusted such that the sum of all components in the composition will total 100 wt. %. The amounts employed will vary with the purpose and character of the desired product and can be readily determined by one skilled in the formulation arts and from the literature.

It is also to be recognized that the choice and amount of ingredients in personal care, home care, health care and institutional care compositions that include the polygalactomannan substituted compositions as variously described above can vary depending on the intended product and its function, as is well known to those skilled in the formulation arts. An extensive listing of ingredients and their conventional functions and product categories have been disclosed and can be readily ascertained from the literature, some of which can serve more than one function.

In accordance with another embodiment, a fracturing fluid composition can comprise, consist of, or consist essentially of: a) the polygalactomannan substituted as variously described above; and b) a component selected from an acid, salt, a friction reducer, ethylene glycol, borate salts, sodium carbonate, potassium carbonate, crosslinkers, glutaraldehyde, water-soluble gelling agents, a proppant, isopropanol, methanol, 2-butoxyethanol, conventional linear gels, borate-crosslinked fluids, organometallic-crosslinked fluids, aluminium phosphate-ester oil gels, viscosity reducing agents, enzymes, pH modifiers, and combinations thereof.

The acid can be selected from hydrochloric acid, acetic acid, citric acid, and combinations thereof; and the friction reducer can comprise a polyacrylamide. The water-soluble gelling agent can comprise a guar gum; and the proppant can comprise a particulate material. The particulate material can comprise sand; and the conventional linear gels can be selected from: 1) cellulose derivatives selected from carboxymethyl cellulose, hydroxyethyl cellulose, carboxymethyl hydroxyethyl cellulose, hydroxypropyl cellulose, methyl hydroxyl ethyl cellulose, and combinations thereof, 2) guar derivatives selected from hydroxypropyl guar, carboxymethyl hydroxypropyl guar, and combinations thereof, and 3) combinations thereof.

The borate-crosslinked fluids can comprise guar-based fluids cross-linked with boron ions; and the organometallic-crosslinked fluids can comprise a metal selected from zirconium, chromium, antimony, titanium, and combinations thereof. The viscosity reducing agents can be selected from oxidizers, enzyme breakers, and combinations thereof.

In accordance with another embodiment, a cleaning composition can comprise, consist of, or consist essentially of: a) the polygalactomannan substituted as variously described above; and b) a component selected from builders, surfactants, bleaches, enzymes, viscosity modifiers, solubilizing agents, corrosion inhibitors, dye transfer inhibitors, anti-redeposition agents, optical brighteners, fabric softeners, colorants, perfumes, and mixtures thereof.

The anti-redeposition agents can comprise carboxymethyl cellulose; and the surfactant can comprise an alkylbenzenesulfonate surfactant. The builders can be water softeners selected from the group consisting of sodium carbonate, complexation agents, soap, zeolites, and sodium triphosphate. The bleaches can be of vegetable origin; and the enzyme can be selected from the group consisting of protease, lipases and amylases.

In accordance with another embodiment, a method for laundering fabrics comprises using the cleaning composition described above as a detergent. Also, a method for cleaning surfaces comprises using the cleaning composition described above.

In accordance with another embodiment, a method for making the polygalactomannan substituted as variously described above can comprise, consist of, or consist essentially of:

(a) combining an aqueous caustic solution with polygalactomannan comprising mannose and galactose at a molar ratio of mannose to galactose of at least about 2.0:1, or 4.0:1, or 7.0:1 to thereby form a first mixture wherein at least a portion of the polygalactomannan is alkalized;

(b) adding a compound selected from the group consisting of 3-chloro-1,2-propanediol; 3-bromo-1,2-dihydroxypropanediol; 3-iodo-1,2-dihydroxypropanediol; 3-tosyl-1,2-dihydroxypropanediol; 3-chloro-2-hydroxypropyl alkyl/phenyl ether; 2,3-epoxy propylphenylether glycidol; and combinations thereof, to the first mixture thereby forming a second mixture;

(c) heating the second mixture to a temperature of from about 40° C. to about 140° C., or from about 70° C. to about 90° C., for a period of about 1 to about 4 hours, or from about 2 to about 3 hours, thereby substituting at least one dihydroxypropyl moiety onto the polygalactomannan to form a dihydroxypropyl-substituted-polygalactomannan;

(d) cooling the second mixture to a temperature of from about 10 to about 60° C., or from about 20 to about 50° C., and adjusting the pH of the second mixture to about 6.0 to 8.5, or to about 7.0 to about 8.0; and (e) recovering the dihydroxypropyl-substituted-polygalactomannan from the second mixture.

In accordance with another embodiment, the method described above can further comprise, consist of, or consist essentially of:

(f) combining the dihydroxypropyl-substituted-polygalactomannan with a second aqueous caustic solution wherein at least a portion of the dihydroxypropyl-substituted-polygalactomannan is alkalized thereby forming a third mixture;

(g) adding a cationic compound, as described above, to the third mixture thereby forming a fourth mixture;

(h) heating the fourth mixture to a temperature of from about 30 to about 100° C., or from about 40 to about 60° C., for a period of about 1 to about 4 hours, or from about 2 to about 3 hours, thereby substituting at least one cationic moiety onto the dihydroxypropyl-substituted-polygalactomannan to form a cation-and-dihydroxypropyl-substituted-polygalactomannan;

(i) cooling the fourth mixture to a temperature of from about 10 to about 50° C., or from about 20 to about 40° C., and adjusting the pH of the fourth mixture to about 6.0 to 8.5, or to about 7 to about 8; and (j) recovering the cation-and-dihydroxypropyl-substituted-polygalactomannan from the fourth mixture.

In accordance with another embodiment, the method described above can further comprise, consist of, or consist essentially of:
(k) combining the cation-and-dihydroxypropyl-substituted-polygalactomannan with a third aqueous caustic solution wherein at least a portion of the cation-and-dihydroxypropyl-substituted-polygalactomannan is alkalized thereby forming a fifth mixture;
(l) adding a hydrophobic compound to the fifth mixture thereby forming a sixth mixture;
(m) heating the sixth mixture to a temperature of from about 30° C. to about 140° C., or from about 80 to about 120° C., for a period of about 1 to about 4 hours, or from about 1 to about 2 hours, thereby substituting at least one hydrophobic moiety onto the cation-and-dihydroxypropyl-substituted-polygalactomannan to form a hydrophobic-and-cation-and-dihydroxypropyl-substituted-polygalactomannan;
(n) cooling the sixth mixture to a temperature of from about 10 to about 50° C., or from about 20 to about 30° C., and adjusting the pH of the sixth mixture to about 6.0 to 8.5, or to about 7 to 8; and
(o) recovering the hydrophobic-and-cation-and-dihydroxypropyl-substituted-polygalactomannan from the sixth mixture.

In accordance with another embodiment, the method for making the polygalactomannan substituted as variously described above in accordance with steps a)-e) can further comprise, consist of, or consist essentially of:
(f) combining the dihydroxypropyl-substituted-polygalactomannan with a second aqueous caustic solution wherein at least a portion of the dihydroxypropyl-substituted-polygalactomannan is alkalized thereby forming a third mixture;
(g) adding a hydrophobic compound to the third mixture thereby forming a fourth mixture;
(h) heating the fourth mixture to a temperature of from about 30° C. to about 140° C., or from about 80° C. to about 120° C., for a period of about 1 to about 4 hours, or from about 1 to about 2 hours, thereby substituting at least one hydrophobic moiety onto the dihydroxypropyl-substituted-polygalactomannan to form a hydrophobic-and-dihydroxypropyl-substituted-polygalactomannan;
(i) cooling the fourth mixture to a temperature of from about 10° C. to about 50° C., or from about 20° C. to about 30° C., and adjusting the pH of the fourth mixture to about 6.0 to about 8.5, or to about 7.0 to about 8.0; and
(j) recovering the hydrophobic-and-dihydroxypropyl-substituted-polygalactomannan from the fourth mixture.

In accordance with another embodiment, a method for making the polygalactomannan substituted as variously described above can comprise, consist of, or consist essentially of:
(i) combining an aqueous caustic solution with polygalactomannan comprising mannose and galactose at a molar ratio of mannose to galactose of at least about 2.0:1 or 4.0:1, or 7.0:1 to thereby form a first mixture wherein at least a portion of the polygalactomannan is alkalized;
(ii) adding a compound selected from the group consisting of 3-chloro-1,2-propanediol; 3-bromo-1,2-dihydroxypropanediol; 3-iodo-1,2-dihydroxypropanediol; 3-tosyl-1,2-dihydroxypropanediol; 3-chloro-2-hydroxypropyl phenyl/alkyl ether; 2,3-epoxy propyl phenyl ether; glycidol; and combinations thereof, to the first mixture thereby forming a second mixture;
(iii) heating the second mixture to a temperature of from about 40° C. to about 140° C., or from about 70° C. to about 90° C., for a period of about 1 to about 4 hours, or from about 2 to about 3 hours, thereby substituting at least one dihydroxypropyl moiety onto the polygalactomannan to form a dihydroxypropyl-substituted-polygalactomannan;
(iv) adding a second aqueous caustic solution to the second mixture thereby forming a third mixture, wherein at least a portion of the dihydroxypropyl-substituted-polygalactomannan is alkalized;
(v) adding a cationic compound to the third mixture thereby forming a fourth mixture; and
(vi) heating the fourth mixture to a temperature of from about 30° C. to about 100° C., or from about 40° C. to about 60° C., for a period of about 1 to about 4 hours, or from about 2 to about 3 hours, thereby substituting at least one cationic moiety onto the dihydroxypropyl-substituted-polygalactomannan to form a cation-and-dihydroxypropyl-substituted-polygalactomannan.

In accordance with another embodiment, the method for making the polygalactomannan substituted as variously described above in accordance with steps i)-vi) can further comprise, consist of, or consist essentially of:
(vii) cooling the fourth mixture to a temperature of from about 10° C. to about 50° C., or from about 20° C. to about 40° C., and adjusting the pH of the fourth mixture to about 6.0 to about 8.5, or to about 7 to about 8; and
(viii) recovering the cation-and-dihydroxypropyl-substituted-polygalactomannan from the fourth mixture.

In accordance with another embodiment, the method for making the polygalactomannan substituted as variously described above in accordance with steps i)-vi) can further comprise, consist of, or consist essentially of:
(ix) following step vi), adding a third aqueous caustic solution to the fourth mixture thereby forming a fifth mixture, wherein at least a portion of the cation-and-dihydroxypropyl-substituted-polygalactomannan is alkalized;
(x) adding a hydrophobic compound to the fifth mixture thereby forming a sixth mixture;
(xi) heating the sixth mixture to a temperature of from about 30° C. to about 140° C., or from about 80° C. to about 120° C., for a period of about 1 to about 4 hours, or from about 1 to about 2 hours, thereby substituting at least one hydrophobic moiety onto the cation-and-dihydroxypropyl-substituted-polygalactomannan to form a hydrophobic-and-cation-and-dihydroxypropyl-substituted-polygalactomannan;
(xii) cooling the sixth mixture to a temperature of from about 10 to about 50° C., or from about 20° C. to about 30° C., and adjusting the pH of the sixth mixture to about 6.0 to about 8.5, or to about 7 to about 8; and
(xiii) recovering the hydrophobic-and-cation-and-dihydroxypropyl-substituted-polygalactomannan from the sixth mixture.

The methods described above for making the substituted polygalactomannan can include employing either a normal slurry process, or a high-solid slurry process, or a half-solution process.

EXAMPLES

Preparation of Polymers

Example 1—Preparation of Dihydroxypropyl Substituted *Cassia* Gum (DHP-CG Polymer A)

Under a nitrogen atmosphere, 40 g *cassia* gum (CG), 150 g isopropanol, 65 g water and a 30 g 50% NaOH solution were mixed to form a slurry. The slurry was stirred for about one hour at room temperature thereby alkalizing the polygalactomannan of the *cassia* gum. 26 g 3-chloro-1,2-propanediol (CPD) was added to the slurry which was then heated to about 80° C. The slurry temperature was maintained at about 80° C. for about 3 hours. The slurry was then neutralized with nitric acid to around 7-8 of pH value, filtered and purified with 80%, 84%, 88% and 98% of acetone solution to form a product. The product was dried at about 60° C. in a ventilated oven for about 1 hour to form the DHP-CG Polymer A powder.

Example 2—Preparation of Dihydroxypropyl Substituted *Cassia* Gum (DHP-CG Polymer E)

Under a nitrogen atmosphere, 40 g *cassia* gum, 150 g isopropanol, 73 g water and a 14 g 50% NaOH solution were mixed to form a slurry. The slurry was stirred for about one hour at room temperature thereby alkalizing the polygalactomannan of the *cassia* gum. 12 g 3-chloro-1,2-propanediol was added to the slurry which was then heated to about 80° C. The slurry temperature was maintained at about 80° C. for about 3 hours. The slurry was then neutralized with nitric acid to around 7-8 of pH value, filtered and purified with 80%, 84%, 88% and 98% solution of acetone to form a product. The product was dried at about 60° C. in a ventilated oven for about 1 hour to form the DHP-CG Polymer E powder.

Example 3—Preparation of Cationic DHP Substituted *Cassia* Gum (Cat-DHP-CG) Polymers The Cat-DHP-CG polymers B-D and F-K were prepared in the following process:
(1) Under nitrogen, a portion of either DHP-CG polymer A or E, isopropanol, water and a 50% NaOH solution were mixed to form a slurry;
(2) The slurry was stirred for about one hour at room temperature thereby alkalizing the DHP-CG polymer;
(3) A quantity of 69% Quab® 188 (commercially available from The Dow Chemicals Inc. USA) was added to the slurry which was heated to 55° C.;
(4) The slurry temperature was maintained at 55° C. for 3 hours; and
(5) The slurry was then neutralized, filtered and purified to form the Cat-DHP-CG polymers B-D, and F-K.

Reagent quantities used in the preparation of polymers B-D, and F-K are shown in Table 1 below.

TABLE 1

Synthesis of Cat. DHP-Cassia gum Polymers B-D and F-K

| Polymer | DHP-CG Polymer | DHP-CG (g) | 69% Quab® 188 (g) | 50% NaOH (g) | Isopropanol (g) | Water (g) |
|---|---|---|---|---|---|---|
| B | A | 12 | 10 | 7 | 50 | 12.5 |
| C | A | 12 | 6 | 4.5 | 50 | 15 |
| D | A | 12 | 3 | 2.5 | 50 | 16.5 |
| F | E | 11 | 10 | 7 | 50 | 12.5 |
| G | E | 11 | 6 | 4 | 50 | 15 |
| H | E | 11 | 3 | 2.5 | 50 | 16.5 |
| I | E | 40 | 20 | 23.3 | 166 | 41.6 |
| J | A | 40 | 36 | 23.3 | 166 | 41.6 |
| K | A | 40 | 22 | 15 | 166 | 50 |

Example 4—Preparation of DHP Substituted Guar Gum (Polymer L)

Under a nitrogen atmosphere, 65 g guar gum, 220 g isopropanol, 86 g water and a 30 g 50% NaOH solution were mixed to form a slurry. The slurry was stirred for about one hour at room temperature thereby alkalizing the polygalactomannan of the guar gum. 43 g 3-chloro-1,2-propanediol (CPD) was added to the slurry which was then heated to about 80° C. The slurry temperature was maintained at about 80° C. for about 3 hours. The slurry was then neutralized with nitric acid to around 7-8 of pH value, filtered and purified with 80%, 84%, 88% and 98% of acetone solution to form a final product. The final product was dried at 60° C. in a ventilated oven for about 1 hour to form the DHP-Guar Polymer powder.

Example 5—Preparation of Cationic DHP Substituted Guar Gum (Polymers M & N)

Polymers M & N were prepared using the same process as those described in Example 3 except that the DHP-CG Polymer A or E was replaced by the DHP-Guar Polymer L obtained from Example 4. Table 2 shows the reactant quantities used for the preparation.

TABLE 2

Synthesis of Cat. DHP-Guar Polymers M and N

| Polymer | 69% QUAB® 188 (g) | DHP-guar (g) | CPD (g) | 50% NaOH (g) | Isopropanol (g) | Water (g) |
|---|---|---|---|---|---|---|
| M | 10.5 | 20 | NA | 6 | 80 | 20 |
| N | 17 | 20 | NA | 12 | 80 | 16 |

Example 6—Preparation of Hydroxypropyl Substituted *Cassia* Gum (HP-CG, Polymer O)

Under a nitrogen atmosphere, 238 g *cassia* gum, 892 g isopropanol, 346 g water and a 223 g 50% NaOH solution were mixed to form a slurry. The slurry was stirred for about one hour at room temperature thereby alkalizing the polygalactomannan of the *cassia* gum. 57.2 g propylene oxide was added to the slurry which was then heated to about 80° C. The slurry temperature was maintained at about 80° C. for about 3 hours. The slurry was then neutralized with nitric acid to around 7-8 of pH value, filtered and purified with 80%, 84%, 88% and 98% of acetone solution to form a product. The product was dried at about 60° C. in a ventilated oven for about 1 hour to form the HP-CG polymer.

Example 7—Preparation of Cationic HP Substituted Guar Gum (Polymers P & Q)

Polymers P & Q were prepared using the same process as those described in Example 3 except that the DHP-CG Polymer A or E was replaced by the HP-CG Polymer O obtained from Example 6 and 60% Quab® 188 was used. Table 3 shows the reactant quantities used for the preparation.

TABLE 3

Synthesis of Cat. HP-Cassia Gum Polymers P and Q

| Polymer | 60% QUAB® 188 (g) | 50% NaOH (g) | Isopropanol (g) | Water (g) |
|---|---|---|---|---|
| P | 36 | 23 | 166 | 42 |
| Q | 24 | 15 | 166 | 50 |

Characterization of Polymers
Method for Determination of Molecular Weight of Galactomannan Derivatives by Size Exclusion Chromatography/Multi-Angle Laser Light Scattering (SEC/MALLS) Conditions Samples of the polymers were prepared for analysis by dissolving 30 mg of polymer in 15 ml of mobile phase and stirring overnight. The analyte solutions were filtered through a 0.45-μm nylon membrane prior to analysis and chromatographed using the SEC/MALLS conditions given below. The polymer elution was detected using refractive index and multi-angle laser light scattering. Data were analyzed using Wyatt ASTRA V software.
Detector 1: Wyatt DAWN DSP
Detector 2: Wyatt Optilab rEX Refractometer @ 40° C.
Columns: TSK Gel CP columns in series
   Pre-column+G6000PWXLCP+G3000PWXLCP
Column Temperature: 40° C.
Mobile phase: 80% 0.1M NaNO3/20% Acetonitrile (v/v)
Flow rate: 0.8 ml/min
Run Time: 60 min
Sample Concentration: 0.2%
Injection volume: 50 μl
dn/dc: 0.126
NMR Method for Determination of HP and DHP MS, and Cat. DS Values of Galactomannan Derivatives Samples of galactomannan derivatives were acid hydrolyzed prior to NMR analysis.
Sample Hydrolysis:

25 mg of sample was dissolved in 1.5 gm 2M trifluoroacetic acid (TFA) in $D_2O$. The solution vial was maintained at 100° C. for 5 hours. Sample vial was cooled for 15 minutes before 0.2 gm of $D_2SO_4$ was added. Sample solution was maintained at 100° C. for one additional hour. The sample solution was allowed to cool down (about 30 mins) and transferred to a 5 mm NMR tube for analysis.
NMR Measurement:

Quantitative $^1H$ NMR spectrum was recorded using a Bruker 400 MHz NMR spectrometer. Acquisition parameters were as follows: temperature=300K, sweep width=20 ppm, pulse width=45 degrees, number of scans=64, relaxation delay=30 seconds. Processing parameters were as follows: line broadening=0.3 Hz.

Spectrum was phase and baseline corrected using standard practices. The peak of unsubstituted β-galactose doublet peak was referenced to 4.61 ppm in the anomeric region (4.51-5.60 ppm).
Region A ($I_A$)=4.51-5.60 ppm (integral area was calibrated to a value of 1.0, other integral areas were relative to this integral value);
Region B ($I_B$)=3.07-4.51 ppm;
Region C ($I_C$)=3.10-3.30 ppm (only for Cat. containing galactomannan);
Region D ($I_D$)=3.24-3.30 ppm (only for Cat. containing galactomannan);
Region E ($I_E$)=1.00-1.40 ppm (only for HP containing galactomannan);
Region G ($I_F$)=1.19-1.33 ppm (only for HP containing galactomannan).
DS/MS were calculated as follows:
For DHP galactomannan:
DHP MS=$(I_B-(I_A*6))/(I_A)$.
For Cat. DHP galactomannan:
DHP MS=$(I_B-(I_A*6)-((I_C-I_D)*1.55)-(I_D*1.22))/(I_A)$; and
Cat. DS=$((I_C-I_D)/9)/(I_A)$.
For HP galactomannan:
HP MS=$((I_E-I_F)/3)/(I_A)$.
For Cat. HP galactomannan:
HP MS=$((I_E-I_F)/3)/(I_A)$; and
Cat. DS=$((I_C-I_D)/9)/(I_A)$.

Table 4 shows the analysis results of the polymers prepared in above Examples. The molecular substitution of the *cassia* gum with dihydroxypropyl groups (DHP-MS) was determined by nuclear magnetic resonance (NMR); and the degree of substitution of the DHP-CG polymers with the Quab® 188 cation (Cat.-DS) was also determined by NMR. The unreacted mannose and galactose levels of the polymers were also determined by NMR.

TABLE 4

Characterization of Polymers

| Polymer | DHP-MS | HP-MS | Cat.-DS | Mn (Da) | Mw (Da) | Mw/Mn |
|---|---|---|---|---|---|---|
| Cassia Gum | NA | NA | NA | 306,000 | 1,060,000 | 2.89 |
| A | 0.601 | NA | NA | 385,000 | 564,000 | 1.46 |
| B | 0.551 | NA | 0.346 | 259,000 | 490,000 | 1.89 |
| C | 0.581 | NA | 0.256 | 317,000 | 503,000 | 1.59 |
| D | 0.566 | NA | 0.144 | 299,000 | 447,000 | 1.49 |
| E | 0.27 | NA | NA | 402,000 | 577,000 | 1.44 |
| F | 0.231 | NA | 0.294 | 207,000 | 305,000 | 1.47 |
| G | 0.275 | NA | 0.239 | 323,000 | 469,000 | 1.45 |
| H | 0.237 | NA | 0.123 | 320,000 | 459,000 | 1.43 |
| I | 0.180 | NA | 0.319 | 284,000 | 300,000 | 1.27 |
| J | 0.593 | NA | 0.436 | 356,000 | 362,000 | 1.02 |
| K | 0.596 | NA | 0.294 | 265,000 | 337,000 | 1.27 |
| L | 0.723 | NA | NA | 244,000 | 499,000 | 2.05 |
| M | 0.556 | NA | 0.292 | 70,000 | 84,000 | 1.2 |
| N | 1.221 | NA | 0.448 | 263,000 | 386,000 | 1.47 |
| O | NA | 0.77 | NA | 312,000 | 458,000 | 1.47 |
| P | NA | 0.240 | 0.443 | 409,000 | 573,000 | 1.40 |
| Q | NA | 0.243 | 0.249 | 313,000 | 467,000 | 1.49 |

NA—Not applicable

Testing of Polymers

Example 8—Testing Polymers A-H in Hair Care Performance

Aqueous formulations A-H were prepared containing 0.2 wt % of each of polymers A-H, respectively; and a comparative aqueous formulation (Comparison) was prepared containing 0.2 wt % of N-Hance™ BF 17 (commercially available from Ashland Inc.). The formulations also each contained the following:
  42.9 wt % Texapon® NSO (SLES, active 12% of Sodium Laureth Sulfate, commercially available from BASF);
  6.25 wt % Tego® Betain F KB 5 (CAPB, active 2% Cocoamidopropyl Betaine. Commercially available from Evonik Industries AG Personal Care);
  2 wt % NaCl;
  0.2 wt % Optiphen™ MIT Plus (MIT, active 100 ppm Methylisothiazolinone, available from Ashland Inc.); and
  48.45 wt % water.

A blank formulation (Blank) was also prepared containing none of the polymers A-H and comparative polymer but including an additional 0.2 wt % water. Properties of the formulations are shown in Table 5.

Bleached Caucasian human hair was separated into individual hair tresses weighing about 3 grams each. For each of the tests, the tress was rinsed with water and 0.2 g of the formulation per gram of tress was lathered into the hair tress for thirty seconds by stroking the tress downwardly. The tress was then rinsed for thirty seconds with water and 0.2 g of the formulation per gram of tress was applied to the tress for a second time, and lathered for thirty seconds by stroking the tress downwardly. The tress was then rinsed again for thirty seconds with water and excess water was removed by passing the tress between the index and middle fingers.

The wet comb total energy (gf-mm) was then measured using the Instron Wet Combing procedure. According to the Instron Wet Combing procedure, each hair tress was soaked for 15 minutes in distilled water. Excess water was removed by passing the tress through the index and middle fingers. The tress was untangled by combing the tress by hand. The tress was then dipped in distilled water three times to rectangle the tress. Excess water was then removed by again passing the tress through the index and middle fingers. The tress was placed on a hanger and combed with the INSTRON instrument which used an Instron strain gauge equipped to measure the total force required to comb the wet hair. Performance was evaluated by the ability of a particular formulation to reduce the required force. Each of the formulations was tested 3 separate times. The results of such testing are shown in Table 5 below and in FIG. 1.

TABLE 5

| Formulation | Brookfield viscosity (mPa·s) | pH | Appearance | Force (gf-mm) | Average | Standard Deviation |
|---|---|---|---|---|---|---|
| A | 1042 | 5.58 | Hazy | 57899.5<br>87039.4<br>74685.4 | 73208 | 14626 |
| B | 1225 | 5.54 | Clear | 30860.8<br>20138.4<br>34161.6 | 28387 | 7332 |
| C | 1230 | 5.54 | Slightly hazy | 11946.7<br>30203.3<br>16103.8 | 19418 | 9569 |
| D | 960 | 5.54 | Slightly hazy | 47229.6<br>57146.6<br>79595.3 | 61324 | 16582 |
| E | 1600 | 5.63 | Very hazy | 52599.6<br>60402.3<br>63872.1 | 58958 | 5773 |
| F | 1000 | 5.52 | Clear | 17269.0<br>19814.2<br>26036.1 | 21040 | 4510 |
| G | 1390 | 5.53 | Clear | 37724.1<br>45603.6<br>26722.6 | 36683 | 9483 |
| H | 1030 | 5.54 | Hazy | 61306.4<br>56961.5<br>34645.8 | 50971 | 14304 |
| Comparison | 2300 | 5.45 | Hazy | 29539.0<br>58778.0<br>56358.4 | 48225 | 16228 |
| Blank | 850 | 5.49 | Clear | 64561.8<br>53140.7<br>57922.9 | 61242 | 4694 |

The data in Table 5 and in FIG. 1 show that the wet comb performance of formulations A-H were each comparable to that of the commercially available N-Hance™ BF 17 cationic guar formulation (Comparison) and the blank shampoo formulation (Blank).

Example 9

Formulations B, C, F and Comparison were separately applied to hair tresses, as described above in Example 8 and the hair tresses were subjected to sensory testing for combability (course side and fine side), stickiness, slipperiness, smoothness, and coatedness. The testing was performed in accordance with the following method:

Sensory Evaluation
  Bleached hair,
  Two tresses used per sample,
  Maximum 10 tresses per time (i.e. 5 samples per time),
  Clean the hair tresses with 4.5% sodium lauryl sulfate (SLS) solution,
  Shampoo the tresses as described above (i.e. 0.1 g shampoo/g hair or other treatment),
  During shampooing (treatment), sensory evaluate the foam speed, foam structure (big bubble, creamy foam, etc.), the amount of foam and the feel during kneading,
  Rinse for 30 seconds with water at 37° C., and sensory evaluate the foam speed, foam structure (big bubble, creamy foam, etc.), the amount of foam and the feel during kneading,
  After rinse-off, sensory evaluate for wet feel (including: stickiness, smoothness, slipperiness, coatedness) and wet comb (including: combability coarse side and combability fine side),
  Place the hair tresses in the humidity chamber, at the following condition: T=23° C., RH=50% to dry overnight,
  After drying step, sensory evaluate for dry feel (including: smoothness, coatedness) and dry comb (combability coarse side, combability fine side),
  The evaluation was performed by five persons, minimum.

Figure 2:
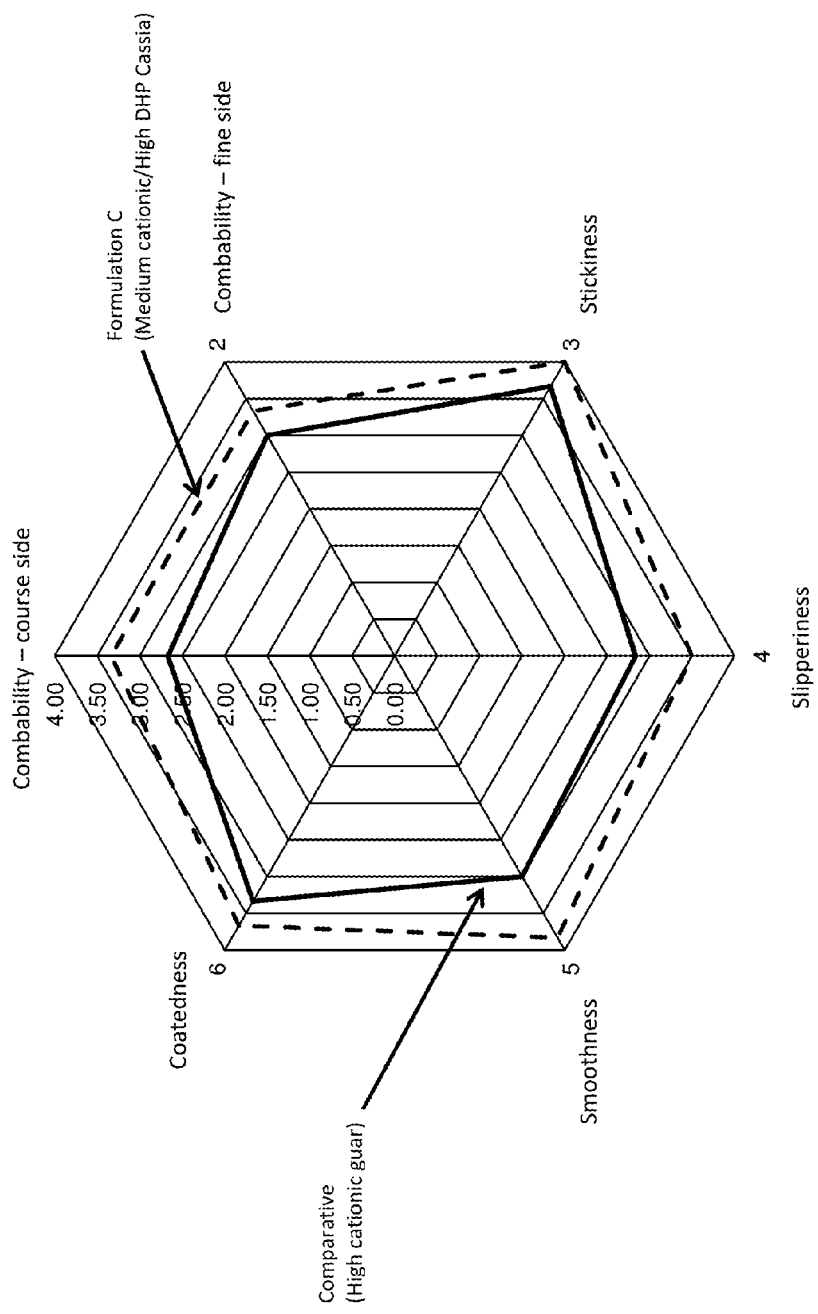
FIG. 2 is a plot showing sensory test results for hair tresses treated with aqueous formulations C and Comparison.
Figure 3:
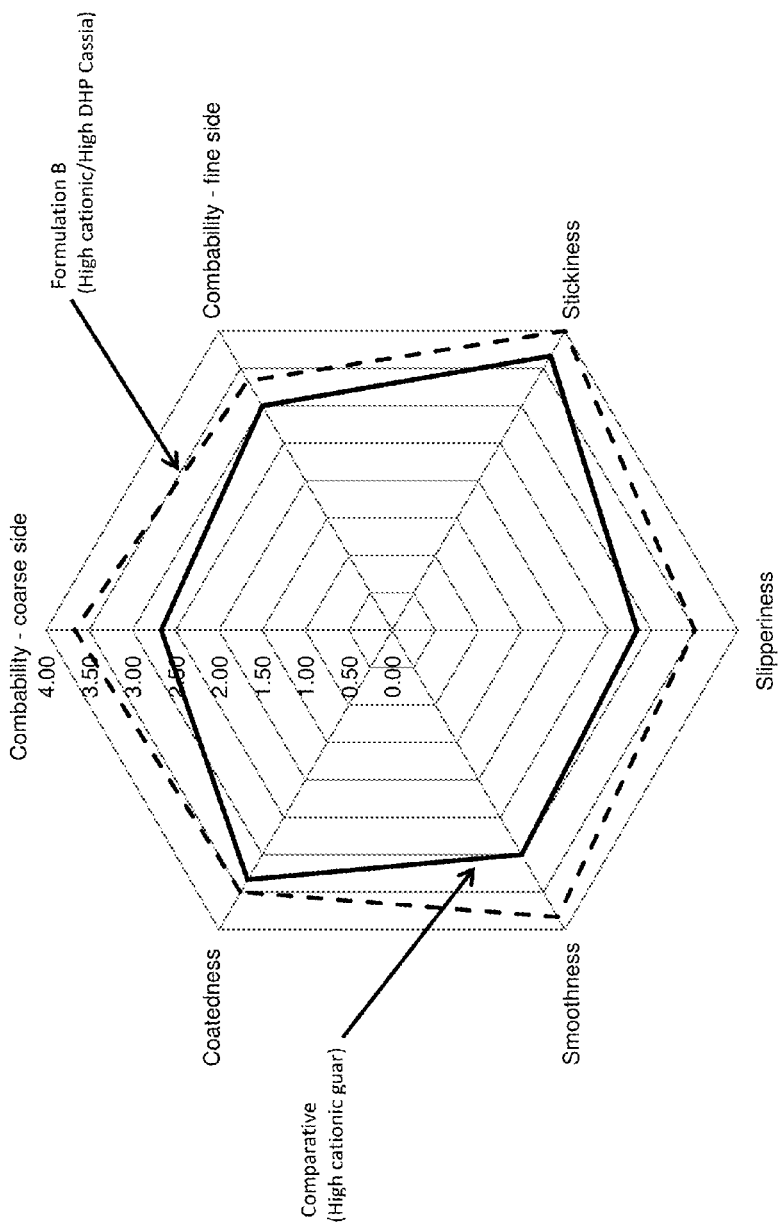
FIG. 3 is a plot showing sensory test results for hair tresses treated with aqueous formulations B and Comparison.
Figure 4:
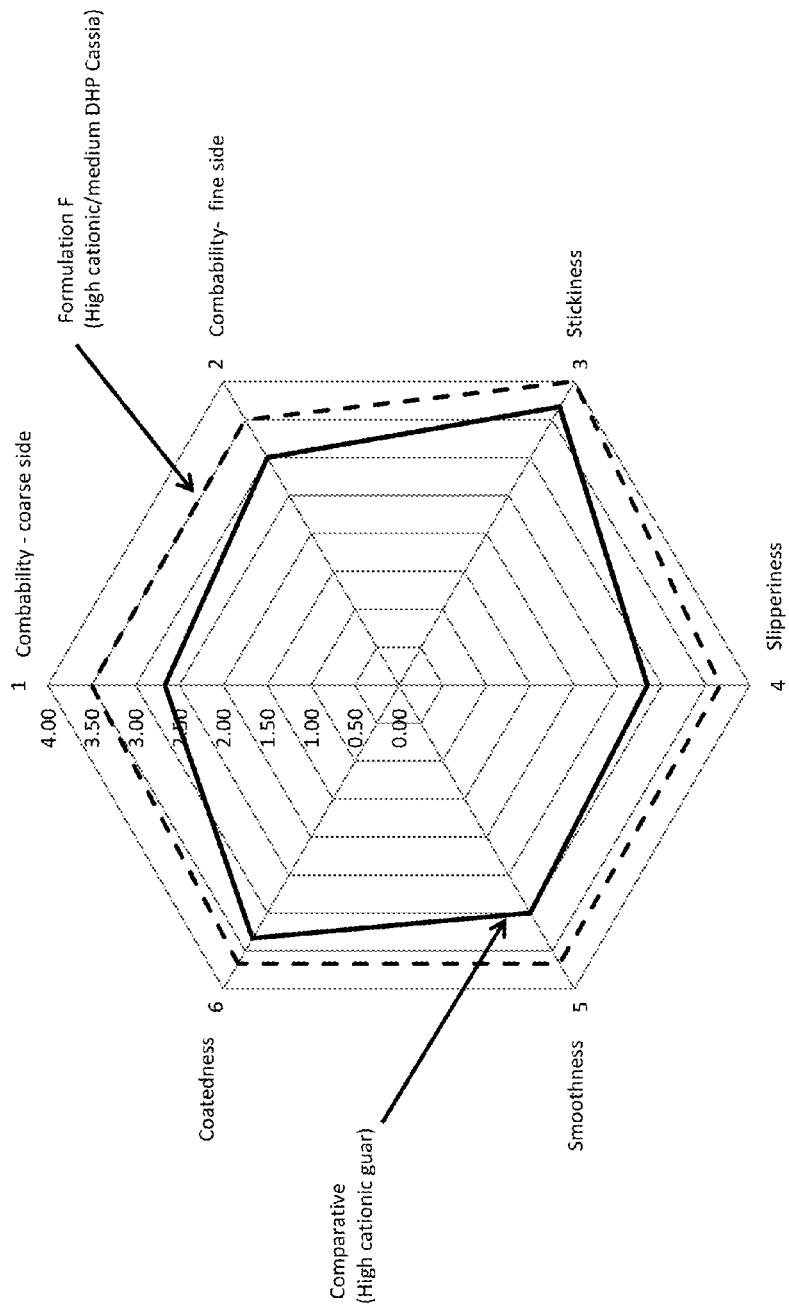
FIG. 4 is a plot showing sensory test results for hair tresses treated with aqueous formulations F and Comparison.

The results of such testing are shown in FIGS. 2-4, which show that the inventive formulations B, C and F demonstrated superior performance in sensory testing as compared to the Comparative formulation.

Example 10—Wet Comb Ability Shampoo Composition

Figure 5:
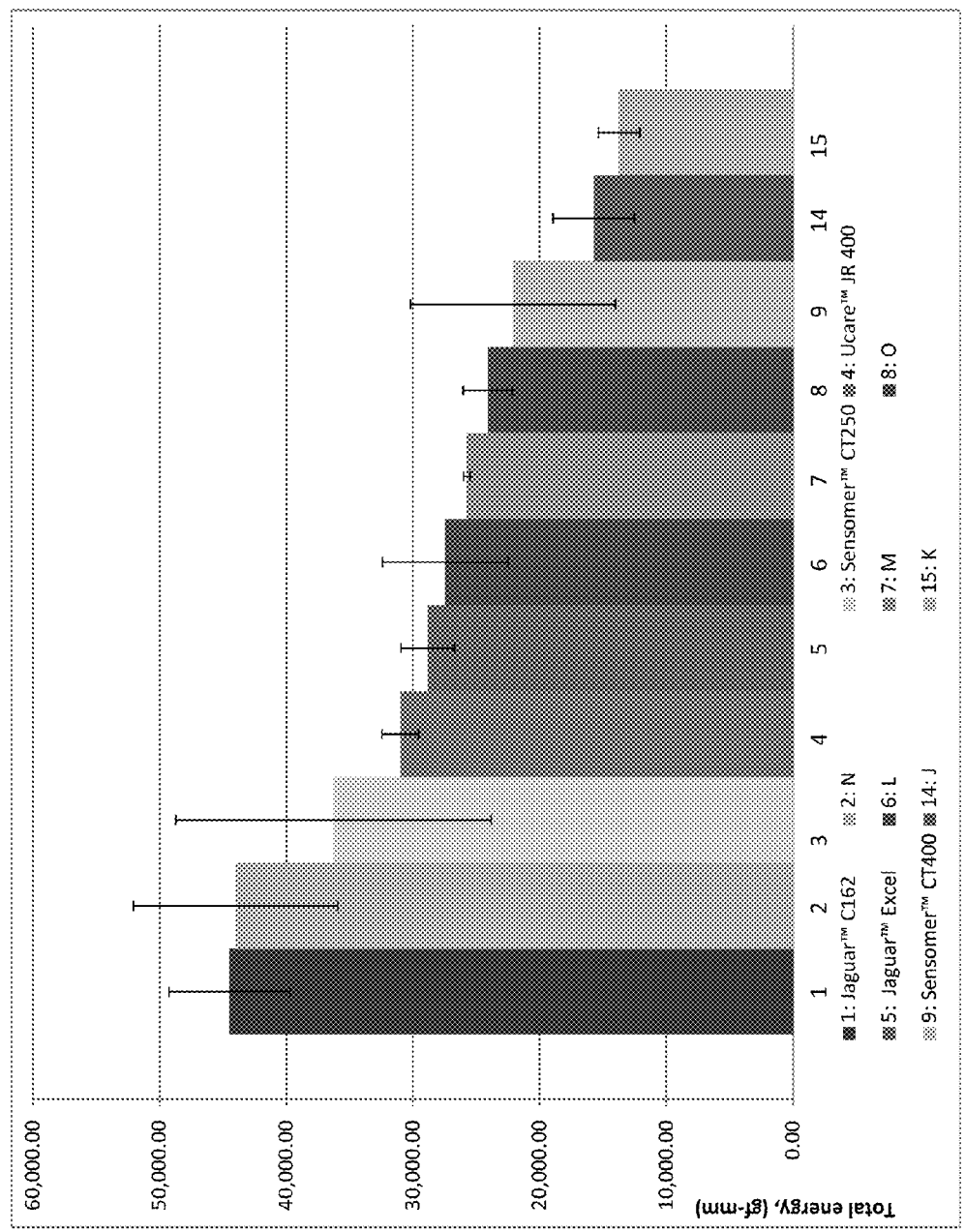
FIG. 5 a plot showing Instron Wet Comb total energy test results for hair tresses treated with DHP guar, DHP *Cassia* derivatives, commercial cationic polysaccharides and cationic HP *Cassia*.

The combing measurement of the hair tresses treated with CPD modified cationic polygalactomannans containing shampoo was done on an Instron device. Table 6 lists the shampoo formulations for testing. For every measurement 3 bleached hair tresses were used and the average was calculated. To measure durable conditioning the tress was first treated with 0.1 g/g hair shampoo, which was then rinsed off and the comb energy was measured. The tress was washed 2 more times and the comb energy was again measured. The results of wet comb energy after 1 and 3 washes are illustrated in FIG. 5 for the shampoo compositions containing different cationic DHP polygalactomannans (CATDH-PGM). The energy needed to comb the tress was listed as gf-mm.

From the results of wet comb ability for the CATDHPGM shampoo compositions, it is evident that the conditioning performance of the CATDHPGM shampoo is in all cases minimum parity to existing cationic guar shampoos and in case of *cassia* even outperforms existing cationic guars.

TABLE 6

Shampoo Formulation

| Sample Polymer | wt % | SLES (2EO) wt % | CAPB wt % | NaCl wt % | MIT wt % | Water wt % | pH |
|---|---|---|---|---|---|---|---|
| J | 0.2 | 12 | 2 | 2 | 0.2 | Ad 100 | 5.64 |
| K | 0.2 | 12 | 2 | 2 | 0.2 | Ad 100 | 5.58 |
| L | 0.2 | 12 | 2 | 2 | 0.2 | Ad 100 | 6.04 |
| M | 0.2 | 12 | 2 | 2 | 0.2 | Ad 100 | 6.03 |
| Jaguar® C162 | 0.2 | 12 | 2 | 2 | 0.2 | Ad 100 | 5.80 |
| Jaguar® Excel | 0.2 | 12 | 2 | 2 | 0.2 | Ad 100 | 5.70 |
| Ucare™ JR 400 | 0.2 | 12 | 2 | 2 | 0.2 | Ad 100 | 5.75 |
| Sensomer CT™ 250 | 0.2 | 12 | 2 | 2 | 0.2 | Ad 100 | 5.74 |
| Sensomer CT™ 400 | 0.2 | 12 | 2 | 2 | 0.2 | Ad 100 | 5.55 |
| P | 0.2 | 12 | 2 | 2 | 0.2 | Ad 100 | 5.51 |
| O | 0.2 | 12 | 2 | 2 | 0.2 | Ad 100 | 5.52 |

Jaguar® C162—Hydroxypropyl guar hydroxypropyl trimonium chloride, commercially available from Solvay Novecare.
Jaguar® Excel—Guar hydroxypropyltrimonium chloride, commercially available from Solvay Novecare.
Ucare™ JR 400—Cellulose, 2-(2-hydroxy-3-(trimethylammonium)propoxy)ethyl ether chloride, commercially available from The Dow Chemical Company.
Sensomer CT™ 250—Cassia hydroxypropyltrimonium chloride, commercially available from Lubrizol Advanced Materials, Inc.
Sensomer CT™ 400—Cassia hydroxypropyltrimonium chloride, commercially available from Lubrizol Advanced Materials, Inc.

In comparison to shampoo formulations with commercial cationic guars, the DHP modified polygalactomannans shampoo formulation delivered in minimum parity performance. In comparison to those PQ10 containing shampoo, the DHP modified polygalactomannans shampoo formulation showed no deposition enhancement.

Clarity of sShampoo Composition—

Figure 6:
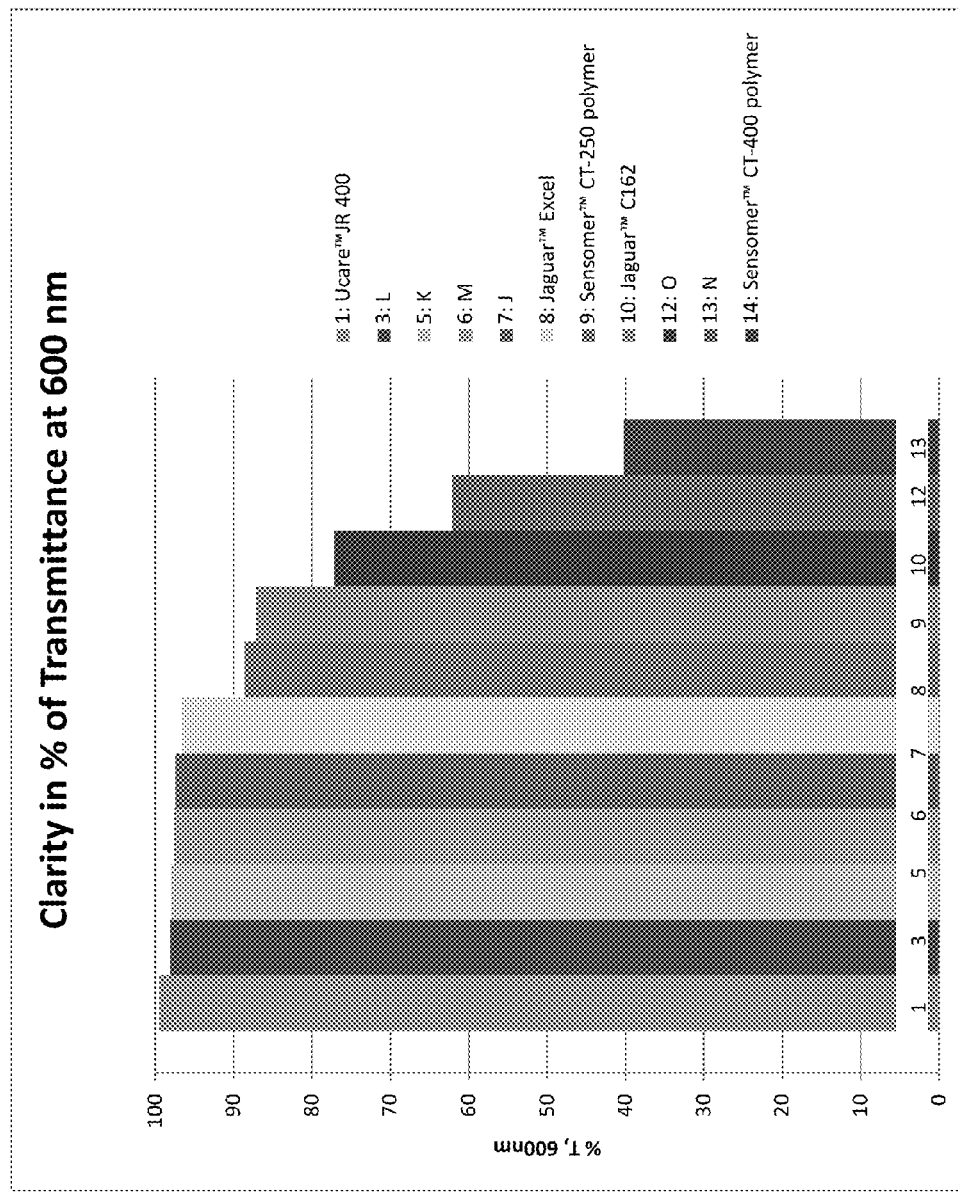
FIG. 6 is a plot showing clarity of shampoo compositions of HP and DHP modified polygalactomannans and commercial cationic polysaccharides in % of transmittance at 600 nm.

Clarity of the shampoo compositions was measured with a spectro photometer at 600 nm, which is shown in FIG. 6. Transmission higher than 95% was usually noticed as a "clear" product. Cationic celluloses like Ucare™ JR 400 formed clear shampoo systems, whereas cationic cassias like the Sensomer™ polymers formed more turbid systems. HP cassias O and N did not form a clear shampoo. DHP modified cationic polygalactomannans formed highly transparent shampoos.

Coacervate Curves—

Common conditioning shampoos are formulated with cationic polymers which are compatible in the shampoo formula, but become incompatible upon dilution with water. Coacervates are the vehicle in shampoos to foster deposition of benefit ingredients like silicone oils, oils or solids like the anti dandruff ingredient zinc pyrithione.

Figure 7:
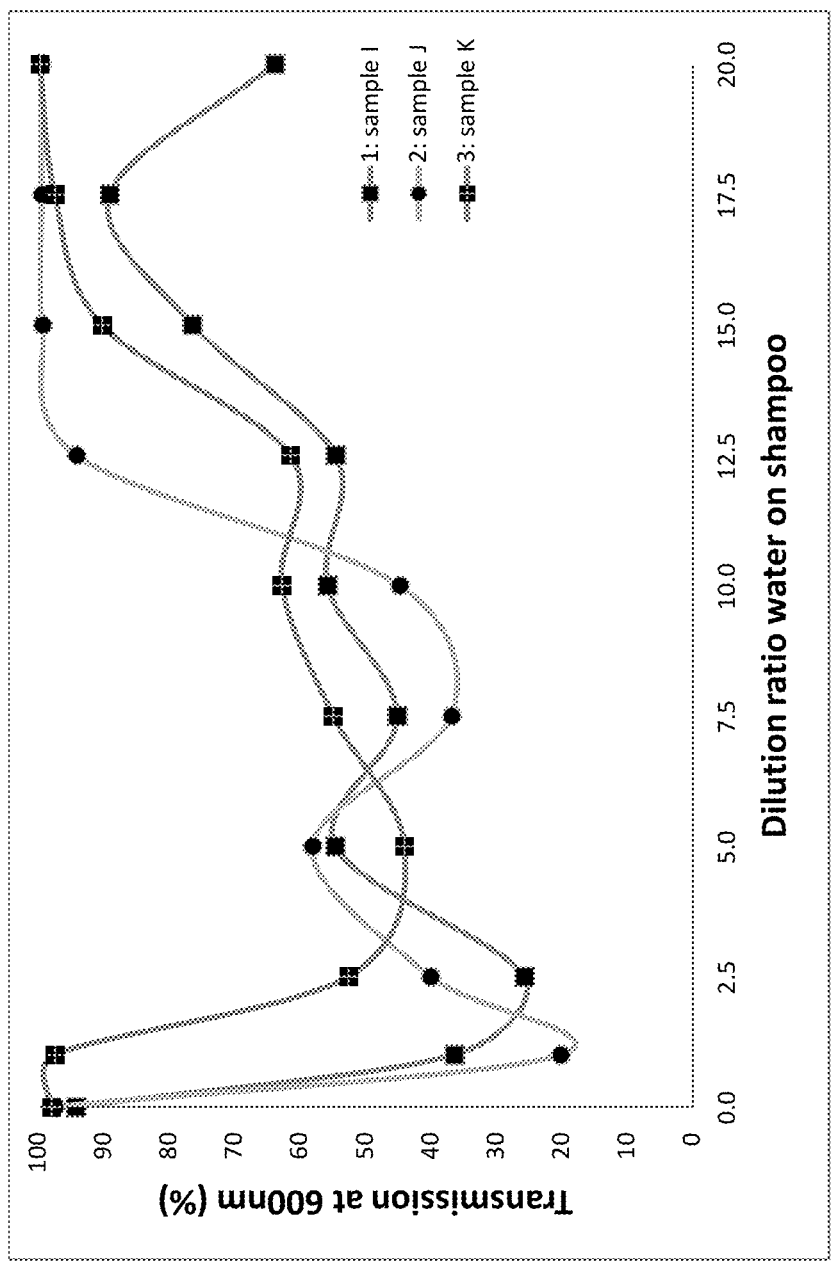
FIG. 7 is a plot showing cationic DHP *Cassia* coacervae curves.
Figure 8:
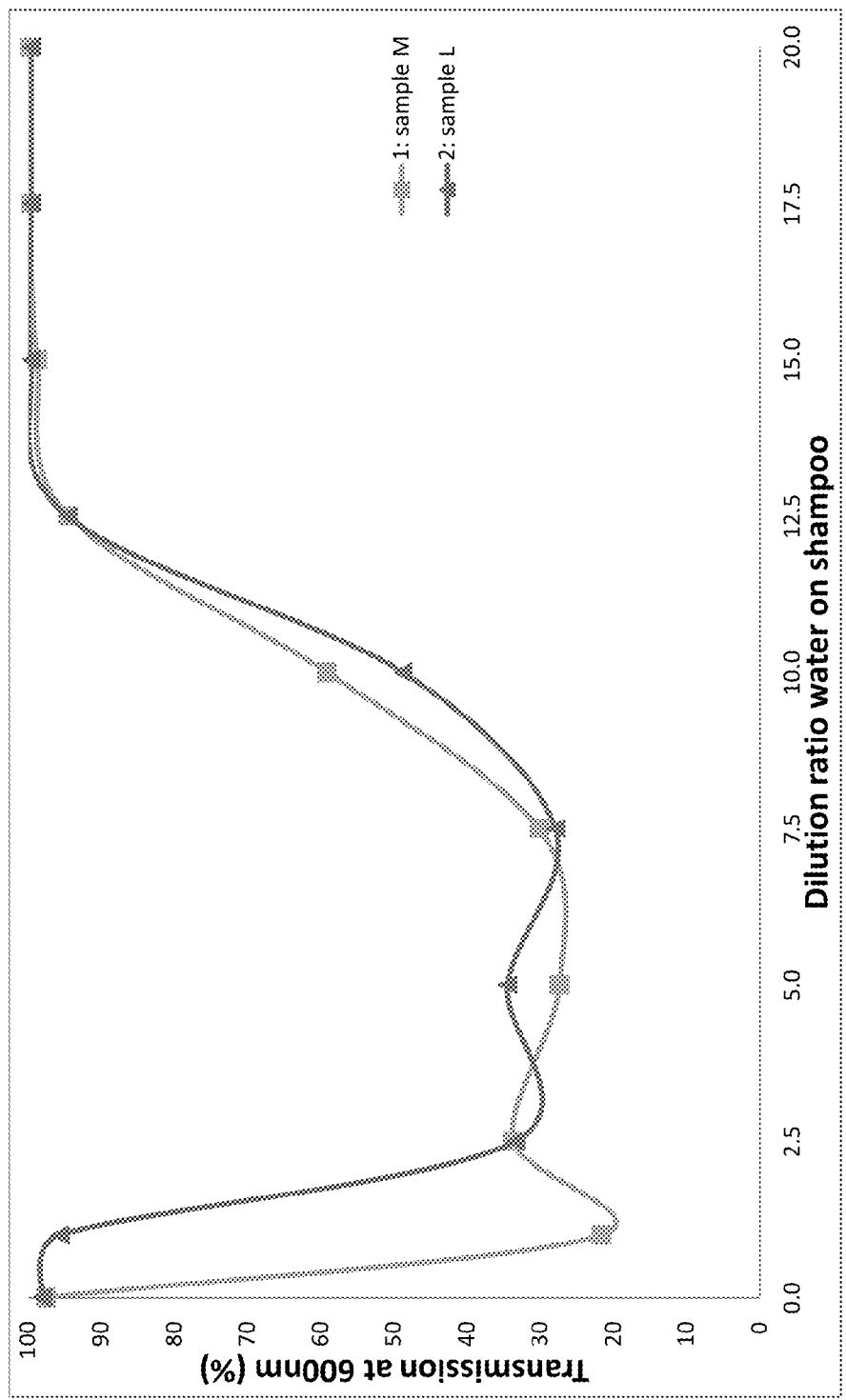
FIG. 8 is a plot showing cationic DHP *Cassia* coacervae curves.

Coacervate curves in FIGS. 7 and 8 show the capability of DHP cassia and guar to form coacervates when the shampoo system was diluted to precipitate thus the shampoo solution was becoming turbid under dilution. As higher the turbidity was as higher the potential to form coacervates.

Example 11—Silicon Deposition

Positive deposition properties were confirmed by silicon deposition studies monitored via XRF. Table 7 lists the shampoo compositions for the tested samples. Damaged hair tresses were washed with a SLES base shampoo to ensure complete removal of all dirt and oils. After that hair was washed with the test shampoo and rinsed (shampoo usage 0.1 g/1 g hair, rinse time 30 sec with 38°-40° C. water). Once hair was dry the hair was mounted on a sample holder and the silicon amount was measured via XRF. As higher the silicone amount found on the hair surface as better the deposition was.

Figure 9:
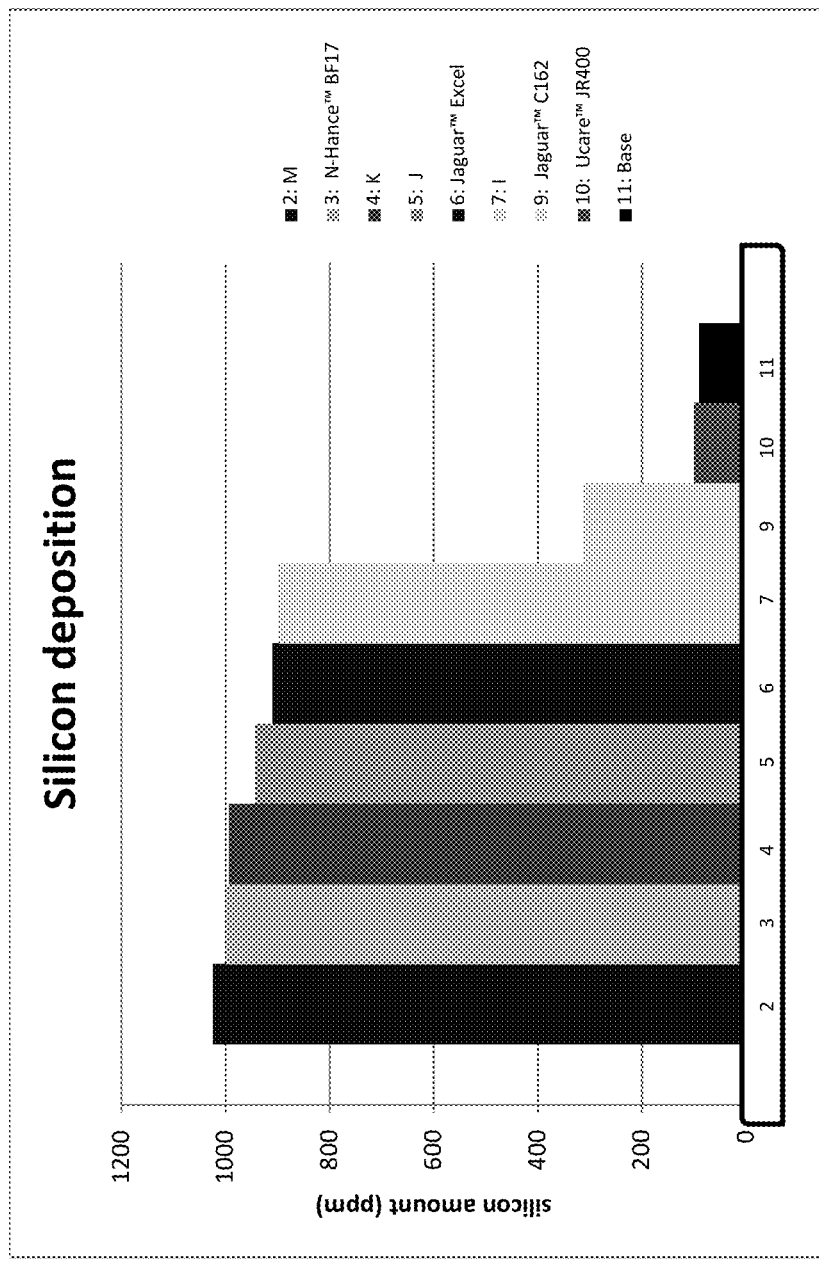
FIG. 9 is a plot showing silicon deposition.

FIG. 9 shows the comparison results. In comparison to shampoo formulations of the commercial cationic guars, the DHP modified polygalactomannans shampoo formulation delivered in minimum parity performance. In comparison to those shampoos containing UCARE™ JR 400, the DHP modified polygalactomannans shampoo formulation showed no deposition enhancement.

TABLE 7

Shampoo Formulation for Silicone Deposition Studies

| Sample Polymer | wt % | Ashland™ 980 Carbomer wt % | SLES (2EO) wt % | CAPB wt % | Xiameter® MEM-1788 wt % | NaCl wt % | MIT wt % | Water wt % | pH* |
|---|---|---|---|---|---|---|---|---|---|
| J | 0.2 | 0.4 | 12 | 2 | 1.0 | 2 | 0.2 | Ad 100 | 5.64 |
| K | 0.2 | 0.4 | 12 | 2 | 1.0 | 2 | 0.2 | Ad 100 | 5.58 |
| L | 0.2 | 0.4 | 12 | 2 | 1.0 | 2 | 0.2 | Ad 100 | 6.04 |
| M | 0.2 | 0.4 | 12 | 2 | 1.0 | 2 | 0.2 | Ad 100 | 6.03 |
| Jaguar™ C162 | 0.2 | 0.4 | 12 | 2 | 1.0 | 2 | 0.2 | Ad 100 | 5.80 |
| Jaguar™ Excel | 0.2 | 0.4 | 12 | 2 | 1.0 | 2 | 0.2 | Ad 100 | 5.70 |
| Ucare™ JR 400 | 0.2 | 0.4 | 12 | 2 | 1.0 | 2 | 0.2 | Ad 100 | 5.75 |

Ashland™ 980 Carbomer—cross-linked polymer of acrylic acid, commercially available from Ashland Inc.
Xiameter® MEM-1788—Dimethiconol TEA-dodecylbenzenesulfonate, commercially available from Dow Corning.

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

Changes may be made in the construction and the operation of the various components, elements and assemblies described herein, and changes may be made in the steps or sequence of steps of the methods described herein without departing from the spirit and the scope of the invention as defined in the following claims.

What is claimed is:

1. A composition comprising a polygalactomannan substituted with at least one dihydroxyalkyl moiety and at least one cationic moiety, wherein the dihydroxyalkyl moiety comprises $C_2$-$C_{12}$ alkyl group and is selected from the group consisting of dihydroxyethyl, dihydroxypropyl, dihydroxybutyl, dihydroxypentyl, and dihyroxyhexy, wherein the composition comprises unsubstituted mannose, substituted mannose, unsubstituted galactose and substituted galactose, and wherein the molar ratio of the combined unsubstituted mannose and substituted mannose to the combined unsubstituted galactose and substituted galactose is at least about 2.0:1.

2. The composition of claim 1, wherein the molar ratio of the unsubstituted mannose to the unsubstituted galactose is from about 2.0:1 to about 7.0:1.

3. The composition of claim 1, wherein the at least one dihydroxyalkyl moiety is substituted on the polygalactomannan in the form of an ether.

4. The composition of claim 1, wherein the average degree of molar substitution of the polygalactomannan by the at least one dihydroxyalkyl moiety is in a range of from about 0.05 to about 5.0.

5. The composition of claim 1 having a number average molecular weight ($M_n$) in a range of from about 50,000 to about 1,000,000, and a weight average molecular weight ($M_w$) in a range of from about 70,000 to about 1,200,000.

6. The composition of claim 1, wherein the dihydroxyalkyl moiety is dihydroxypropyl moiety.

7. The composition of claim 1, wherein the polygalactomannan is further substituted with at least one hydrophobic moiety.

8. The composition of claim 7, wherein the at least one hydrophobic moiety is substituted on the at least one cationic moiety.

9. The composition of claim 7, wherein the at least one hydrophobic moiety is selected from a $C_4$-$C_{22}$ alkyl radical.

10. The composition of claim 1, wherein the polygalactomannan is further substituted with at least one hydrophobic moiety.

11. The composition of claim 10, wherein the at least one hydrophobic moiety is selected from a $C_4$-$C_{22}$ alkyl radical.

12. The composition of claim 1 further comprising at least one component selected from the group consisting of surfactants, fatty acid soap, hair and skin conditioning agents, suspending aids, emollients, emulsifiers, rheology modifiers, thickening agents, vitamins, hair growth promoters, self-tanning agents, sunscreens, skin lighteners, anti-aging compounds, anti-wrinkle compounds, anti-cellulite compounds, anti-acne compounds, anti-dandruff agents, anti-inflammatory compounds, analgesics, antiperspirant agents, deodorant agents, hair fixatives, particulates, abrasives, moisturizers, antioxidants, keratolytic agents, anti-static agents, foam boosters, hydrotropes, solublizing agents, chelating agents, antimicrobial agents, antifungal agents, pH adjusting agents, chelating agents, buffering agents, botanicals, hair colorants, hair dye, oxidizing agents, reducing agents, hair and skin bleaching agents, pigments, anticaries, anti-tartar agents, anti-plaque agents, solvents, a rheology modifier, and combinations thereof.

13. A hair fixative composition comprising:
a) the composition of claim 1; and
b) a component selected from a rheology modifier, a surfactant, an auxiliary fixative, a solvent, water, a conditioner, a propellant, neutralizing agent, fragrance, fragrance solubilizer, thickener, preservative, emulsifier, emollient, humectant, colorant, wax, and mixtures thereof.

14. The hair fixative composition of claim 13, wherein the conditioner is selected from the group consisting of silicones, organic conditioning oils, natural and synthetic waxes, cationic polymers, and combinations thereof.

15. The hair fixative composition of claim 13, wherein the propellant is selected from the group consisting of propane, butane, isobutane, dimethyl ether, 1,1-difluoroethane, HFO-1234ze (tetrafluoropropylene), carbon dioxide, and mixtures thereof.

16. The composition of claim 1, wherein the polygalactomannan is isolated from the endosperm of the seeds of *Cassia tora*, *Cassia obtusifolia*, or combinations thereof.

17. A method for making a non-hydrophobically modified dihydroxypropyl- and cationic-substituted-polygalactomannan comprising:
a) combining an aqueous caustic solution with polygalactomannan comprising mannose and galactose at a molar ratio of mannose to galactose of at least about 2.0:1 to form a first mixture wherein at least a portion of the polygalactomannan is alkalized;
b) adding a compound selected from the group consisting of 3-chloro-1,2-propanediol, 3-bromo-1,2-dihydroxypropanediol, 3-iodo-1,2-dihydroxypropanediol, 3-tosyl-1,2-dihydroxypropanediol, 3-chloro-2-hydroxypropyl phenyl/alkyl ether, 2,3-epoxy propyl phenyl ether, glycidol, and combinations thereof, to the first mixture to form a second mixture;
c) heating the second mixture to a temperature of from about 40° C. to about 140° C. for a period of about 1 to about 4 hours to substitute at least one dihydroxypropyl moiety onto the polygalactomannan to form the dihydroxypropyl-substituted-polygalactomannan;
d) cooling the second mixture to a temperature of from about 10° to about 60° C. and adjusting the pH of the second mixture to about 6.0 to 8.5;
e) recovering the dihydroxypropyl-substituted-polygalactomannan from the second mixture;
f) combining the dihydroxypropyl-substituted-polygalactomannan with a second aqueous caustic solution wherein at least a portion of the dihydroxypropyl-substituted-polygalactomannan is alkalized to form a third mixture;
g) adding a cationic compound to the third mixture to form a fourth mixture;
h) heating the fourth mixture to a temperature of from about 30° C. to about 100° C. for a period of about 1 to about 4 hours to substitute at least one cationic moiety onto the dihydroxypropyl-substituted-polygalactomannan to form a cation-and-dihydroxypropyl-substituted-polygalactomannan;
i) cooling the fourth mixture to a temperature of from about 10° C. to about 50° C. and adjusting the pH of the fourth mixture to about 6.0 to 8.5; and
j) recovering the cation-and-dihydroxypropyl-substituted-polygalactomannan from the fourth mixture.

18. The method of claim 17 further comprising:
k) combining the cation-and-dihydroxypropyl-substituted-polygalactomannan with a third aqueous caustic solution wherein at least a portion of the cation-and-dihydroxypropyl-substituted-polygalactomannan is alkalized thereby forming a fifth mixture;
l) adding a hydrophobic compound to the fifth mixture to form a sixth mixture;
m) heating the sixth mixture to a temperature of from about 30° C. to about 140° C. for a period of about 1 to about 4 hours to substitute at least one hydrophobic moiety onto the cation-and-dihydroxypropyl-substituted-polygalactomannan to form a hydrophobic-and-cation-and-dihydroxypropyl-substituted-polygalactomannan;

n) cooling the sixth mixture to a temperature of from about 10° C. to about 50° C. and adjusting the pH of the sixth mixture to about 6.0 to 8.5; and o) recovering the hydrophobic-and-cation-and-dihydroxypropyl-substituted-polygalactomannan from the sixth mixture.

* * * * *